United States Patent
Bianchi et al.

(10) Patent No.: US 10,413,593 B2
(45) Date of Patent: Sep. 17, 2019

(54) CO-AGONISTS OF THE GLUCAGON AND GLP-1 RECEPTORS

(71) Applicant: MERCK SHARP & DOHME CORP., Rahway, NJ (US)

(72) Inventors: Elisabetta Bianchi, Pomezia (IT); Paul E. Carrington, South San Francisco, CA (US); Qiaolin Deng, Edison, NJ (US); Ravi Nargund, East Brunswick, NJ (US); Federica Orvieto, Pomezia (IT); Anandan Palani, Bridgewater, NJ (US); Antonello Pessi, Rome (IT); Thomas Joseph Tucker, North Wales, PA (US); Chengwei Wu, Ambler, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/519,565

(22) PCT Filed: Oct. 22, 2015

(86) PCT No.: PCT/US2015/056794
§ 371 (c)(1),
(2) Date: Apr. 17, 2017

(87) PCT Pub. No.: WO2016/065090
PCT Pub. Date: Apr. 28, 2016

(65) Prior Publication Data
US 2017/0360893 A1     Dec. 21, 2017

Related U.S. Application Data

(60) Provisional application No. 62/208,869, filed on Aug. 24, 2015, provisional application No. 62/068,157, filed on Oct. 24, 2014.

(51) Int. Cl.
*C07K 14/605* (2006.01)
*A61K 38/26* (2006.01)
*A61K 38/28* (2006.01)

(52) U.S. Cl.
CPC .............. *A61K 38/28* (2013.01); *A61K 38/26* (2013.01); *C07K 14/605* (2013.01)

(58) Field of Classification Search
None
See application file for complete search history.

(56) References Cited

U.S. PATENT DOCUMENTS

| | | | |
|---|---|---|---|
| 8,703,701 B2 | 4/2014 | Dimarchi et al. | |
| 2011/0288003 A1* | 11/2011 | DiMarchi | A61K 38/26 514/1.3 |
| 2012/0288511 A1* | 11/2012 | Dimarchi | C07K 14/605 424/178.1 |
| 2012/0295846 A1 | 11/2012 | Hagendorf et al. | |
| 2012/0329707 A1* | 12/2012 | DiMarchi | C07K 14/605 514/5.3 |
| 2012/0329708 A1 | 12/2012 | DiMarchi et al. | |
| 2014/0206607 A1 | 7/2014 | Dimarchi et al. | |
| 2014/0221283 A1 | 8/2014 | Dimarchi et al. | |
| 2016/0114000 A1 | 4/2016 | Bianchi et al. | |

FOREIGN PATENT DOCUMENTS

| | | |
|---|---|---|
| JP | 2014525901 | 8/2015 |
| WO | WO1998019698 | 5/1998 |
| WO | 2003022304 | 3/2003 |
| WO | 2003039485 A2 | 5/2003 |
| WO | WO2003103572 | 12/2003 |
| WO | 2004062685 | 7/2004 |
| WO | 2006083689 A2 | 8/2006 |
| WO | 2006096461 A2 | 9/2006 |
| WO | 2006134340 | 12/2006 |
| WO | WO2007056362 | 5/2007 |
| WO | 2008071394 A1 | 6/2008 |
| WO | 2008086395 A2 | 7/2008 |
| WO | WO2008086086 | 7/2008 |
| WO | 2008101017 | 8/2008 |
| WO | WO2008116133 A1 | 9/2008 |
| WO | WO2009058662 | 5/2009 |
| WO | WO2009058734 | 5/2009 |
| WO | 2009099763 | 8/2009 |
| WO | 2009155258 | 12/2009 |
| WO | WO2009155257 | 12/2009 |

(Continued)

OTHER PUBLICATIONS

Wang et al., Dose Response Effects of Insulin Glargine in Type 2 Diabetes, Diabetes Care 33: 1555-60 (2010)).*
Chalasani et al., "The diagnosis and management of non-alcoholic fatty liver disease: practice Guideline by the American Association for the Study of Liver Diseases, American College of Gastroenterology, and the American Gastroenterological Association," Chalasani et al., Hepatology 55:2005-2023 (2012)).*
Cornier et al., "The metabolic syndrome", Endo. Rev. 29:777-822 (2008).*
WHO Cardiovascular guidelines accessed at Mar. 16, 2015 at URL who.int/cardiovascular_diseases/guidelines/Full%20text.pdf.*

(Continued)

*Primary Examiner* — Julie Ha
*Assistant Examiner* — Kristina M Hellman
(74) *Attorney, Agent, or Firm* — Baerbel R. Brown; Catherine D. Fitch

(57) ABSTRACT

Described are peptide analogs of glucagon, which have been modified to be resistant to cleavage and inactivation by dipeptidyl peptidase IV (DPP-IV) and to increase in vivo half-life of the peptide analog while enabling the peptide analog to have relatively balanced agonist activity at the glucagon-like peptide 1 (GLP-1) receptor and the glucagon (GCG) receptor, and the use of such GLP-1 receptor/GCG receptor co-agonists for treatment of metabolic disorders such as diabetes, non-alcoholic fatty liver disease (NAFLD), non-alcoholic steatohepatitis (NASH), and obesity.

30 Claims, 4 Drawing Sheets
Specification includes a Sequence Listing.

(56) References Cited

FOREIGN PATENT DOCUMENTS

| WO | WO2010011439 | 1/2010 |
| WO | WO2010071807 | 6/2010 |
| WO | 2010096052 | 8/2010 |
| WO | WO2010096142 | 8/2010 |
| WO | WO2010148089 | 12/2010 |
| WO | 2011075393 | 6/2011 |
| WO | WO2011094337 | 8/2011 |
| WO | WO2011143208 A1 | 11/2011 |
| WO | 2011156324 A1 | 12/2011 |
| WO | WO2011163012 | 12/2011 |
| WO | WO2011163462 | 12/2011 |
| WO | WO2011163473 | 12/2011 |
| WO | WO2012088116 | 6/2012 |
| WO | WO2012088379 | 6/2012 |
| WO | 2012129013 A1 | 9/2012 |
| WO | 2012177443 | 12/2012 |
| WO | 2012177444 | 12/2012 |
| WO | WO201319212 | 12/2013 |
| WO | WO2013192130 | 12/2013 |
| WO | 2014114651 A1 | 7/2014 |

OTHER PUBLICATIONS

Metabolic Disease, Encyclopedia Britannica, pp. 1-13, (2006) accessed at URL britannica.com/science/metabolic-disease, Jan. 29, 2019.*
Arekat, Mona, R. et al., Dramatic Improvement of BMD Following Vitamin D Therapy in a Bone Marrow Transplant Recipient, Journal of Clinical Densitometry, 2002, p. 267-271, vol. 5, No. 3.
Day, Jonathan, W. et al., Charge inversion at position 68 of the glucagon and glucagon-like pepitde-1 receptors supports selectivity in hormone action, Journal of Peptide Science, 2011, p. 218-225, vol. 17.
Patterson, James, T. et al., Functional association of the N-terminal residues with the central region in glucagon-related peptides, Journal of Peptide Science, 2011, p. 659-666, vol. 17.
Baggio et al., Oxyntomodulin and Glucagon-Like Peptide-1 Differentially, Gastroenterol., 2004, pp. 546-558, 127.
Baldissera et al., Oxyntomodulin (glicentin-(33-69)): pharmacokinetics, binding to liver cell membranes effects on isolated perfused pig pancreas, and secretion from isolated perfused lower small intestine of pigs, Regul. Pept., 1988, pp. 151-166, 21.
Choudhri et al., Differential hypothalamic neuronal activation following peripheral injection of GLP-1 and oxyntomodulin in mice detected by manganese-enhanced magnetic resonance imaging, Biochem. Biophys. Res. Commun., 2006, pp. 298-306, 350.
Cohen et al., Oxyntomodulin Suppresses Appetite and Reduces Food intake in Humans, J. Clin. Endocrinol. Metab., 2003, pp. 4696-4701, 88.
Dakin et al., Oxyntomodulin ameliorates glucose intolerance in mice fed a high-fat diet, Am. J. Physiol. Endocrinol. Metab., 2008, pp. E142-E147, 294.
Dakin et al., Oxyntomodulin Inhibits Food Intake in the Rat, Endocrinology, 2001, pp. 4244-4250, 142.
Dakin et al., Peripheral Oxyntomodulin Reduces Food Intake and Body Weight Gain in Rats, Endocrinology, 2004, pp. 2687-2695, 145.

Dakin et al., Repeated ICV administration of oxyntomodulin causes a greater reduction in body weight gain than in pair-fed rats, Am. J. Physiol. Endocrinol. Metab., 2002, pp. E1173-E1177, 283.
Day, Jonathan W., A New Glucagon and GLP 1 co agonist eliminates obesity in rodents, Nature Chemical Biology, 2009, No. 10 pp. 749-757, 5.
Drucker et al., Biologic actions and therapeutic potential of the proglucagon-derived peptides, J. Nat. Clin. Pract. Endocrinol. Metab., 2005, pp. 22-31, 1.
Geneseq Online, Human Glucagon Analog Peptide, SEQ ID No. 702, 2012, XP002752726 Database Accession No. AZP78778.
Gros et al., Glucagon-like Peptide-1-(7-36) Amide Oxyntomodulin & Glucagon Interact with a common receptor in a Somatostatin secreting cell line, Endocrinol., 1993, pp. 631-638, 133.
Habegger et al., The metabolic actions of glucagon revisited, Nat. Rev. Endocrinol., 2010, pp. 689-697, 6.
Holst, Gut hormones as pharmaceuticals From enteroglucagon to GLP-1 and GLP-2, Regul. Pept., 2000, pp. 45-51, 93.
Jarrouse et al., A Pure Enteroglucagon, Oxyntomodulin (Glucagon 37), Stimulates Insulin Release in Perfused Rat Pancreas, Endocrinol., 1984, pp. 102-105, 115.
Jiang et al., Glucagon and regulation of glucose metabolism, Am. J. Physiol. Endocrinol. Metab., 2003, pp. E671-E678, 284.
Jorgensen et al., Oxyntomodulin Differentially Affects Glucagon-Like Peptide-1 Receptor Beta-Arrestin Recruitment and Signaling through G alpha s, J. Pharma. Exp. Therapeut., 2007, pp. 148-154, 322.
Lykkegaard et al., Regulatory Role of Glucose and Melanocortin 4 Receptor in AMP-Activated Protein Kinase Activity in the Hypothalamus: Association with Feeding Behavior, ADA Scientific Sessions, Abstract No. 1506 P, 2003.
Pocai et al., Glucagon-Like Peptide 1/Glucagon Receptor Dual Agonism Reverses Obesity in Mice, Diabetes, 2009, pp. 2258-2266, 58.
Salter, Metabolic Effects of Glucagon in the Wistar Rat, Am. J. Clin. Nutr., 1960, pp. 535-539, 8.
Schjoldager et al., Oxyntomodulin: a potential hormone from the distal gut. Pharmacokinetics and effects on gastric acid and insulin secretion in man, Eur. J. Clin. Invest., 1988, pp. 499-503, 18.
Sowden et al., Oxyntomodulin increases intrinsic heart rate in mice independent of the glucagon-like peptide-1 receptor, Am. J. Physiol. Regul. Integr. Comp. Physiol., 2007, pp. R962-R970, 292.
Wynne et al., Subcutaneous Oxyntomodulin Reduces Body Weight in Overweight and Obese Subjects, Diabetes, 2005, pp. 2390-2395, 54.
Zhu et al., The Role of Dipeptidyl Peptidase IV in the Cleavage of Glucagon Family Peptides, J. Biol. Chem., 2002, pp. 22418-22423, 278.
Tan, Tricia, M. et al., Coadministration of Glucagon-Like Peptide-1 During Glucagon Infusion in Humans Results in Increased Energy Expenditure and Amelioration of Hyperglycemia, Diabetes, 2013, p. 1131-1138, vol. 62.
Correa et al., A graph structural method for prediction of polymer properties, Brazilian Journal of Chemical Engineering, 2004, Issue 4, pp. 621-628, 21.
Moret et al., New stochastic strategy to analyze helix folding, Biophysical Journal, 2002, pp. 1123-1132, 82.

* cited by examiner

```
                            SEQUENCE LISTING

<160> NUMBER OF SEQ ID NOS: 35

<210> SEQ ID NO 1
<211> LENGTH: 29
<212> TYPE: PRT
<213> ORGANISM: Homo sapiens

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 2
<211> LENGTH: 30
<212> TYPE: PRT
<213> ORGANISM: Homo sapiens

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 3
<211> LENGTH: 37
<212> TYPE: PRT
<213> ORGANISM: Homo sapiens

<400> SEQUENCE: 3

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 4
<211> LENGTH: 39
<212> TYPE: PRT
<213> ORGANISM: Heloderma suspectum

<400> SEQUENCE: 4

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 5
<211> LENGTH: 33
<212> TYPE: PRT
<213> ORGANISM: Homo sapiens
```

```
<400> SEQUENCE: 5

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 6
<211> LENGTH: 29
<212> TYPE: PRT
<213> ORGANISM: Artificial sequence
<220> FEATURE:
<223> OTHER INFORMATION: Co-agonist Peptide 1
<220> FEATURE:
<221> NAME/KEY: MISC_FEATURE
<222> LOCATION: (2)..(2)
<223> OTHER INFORMATION: Xaa = D-serine
<220> FEATURE:
<221> NAME/KEY: MISC_FEATURE
<222> LOCATION: (10)..(10)
<223> OTHER INFORMATION: Lysine conjugated to C16 via a gamme-Glu
      spacer
<220> FEATURE:
<221> NAME/KEY: MISC_FEATURE
<222> LOCATION: (29)..(29)
<223> OTHER INFORMATION: C-terminal amide

<400> SEQUENCE: 6

His Xaa Gln Gly Thr Phe Thr Ser Asp Lys Ser Lys Tyr Leu Asp Ala
1               5                   10                  15

Arg Ala Ala Gln Asp Phe Val Gln Trp Leu Leu Asp Thr
            20                  25

<210> SEQ ID NO 7
<211> LENGTH: 29
<212> TYPE: PRT
<213> ORGANISM: Artificial sequence
<220> FEATURE:
<223> OTHER INFORMATION: Co-agonist peptide 2
<220> FEATURE:
<221> NAME/KEY: MISC_FEATURE
<222> LOCATION: (2)..(2)
<223> OTHER INFORMATION: Xaa = D-serine
<220> FEATURE:
<221> NAME/KEY: MISC_FEATURE
<222> LOCATION: (10)..(10)
<223> OTHER INFORMATION: Lysine conjugated to C16 via a gamma-Glu
      gamma-Glu spacer
<220> FEATURE:
<221> NAME/KEY: MISC_FEATURE
<222> LOCATION: (29)..(29)
<223> OTHER INFORMATION: C-terminal amide

<400> SEQUENCE: 7

His Xaa Gln Gly Thr Phe Thr Ser Asp Lys Ser Lys Tyr Leu Asp Val
1               5                   10                  15

Arg Arg Ala Gln Asp Phe Val Gln Trp Leu Leu Asp Thr
            20                  25

<210> SEQ ID NO 8
<211> LENGTH: 29
<212> TYPE: PRT
<213> ORGANISM: artificial sequence
<220> FEATURE:
<223> OTHER INFORMATION: Co-agonist peptide 3
<220> FEATURE:
<221> NAME/KEY: MISC_FEATURE
<222> LOCATION: (2)..(2)
<223> OTHER INFORMATION: Xaa = D-serine
```

```
<220> FEATURE:
<221> NAME/KEY: MISC_FEATURE
<222> LOCATION: (10)..(10)
<223> OTHER INFORMATION: Lysine conjugated to C16 via a gamma-Glue
      gamma-Glu spacer
<220> FEATURE:
<221> NAME/KEY: MISC_FEATURE
<222> LOCATION: (29)..(29)
<223> OTHER INFORMATION: C-terminal amide

<400> SEQUENCE: 8

His Xaa Gln Gly Thr Phe Thr Ser Asp Lys Ser Lys Tyr Leu Asp Val
1               5                   10                  15

Arg Ala Ala Gln Asp Phe Val Gln Trp Leu Leu Asp Thr
            20                  25

<210> SEQ ID NO 9
<211> LENGTH: 29
<212> TYPE: PRT
<213> ORGANISM: Artificial Sequence
<220> FEATURE:
<223> OTHER INFORMATION: Co-agonist peptide 4
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (10)..(10)
<223> OTHER INFORMATION: Lysine conjugated to C16 via gamma-Glu
      gamma-Glu spacer
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: MISC_FEATURE
<222> LOCATION: (27)..(27)
<223> OTHER INFORMATION: Xaa = noreleucine
<220> FEATURE:
<221> NAME/KEY: MISC_FEATURE
<222> LOCATION: (29)..(29)
<223> OTHER INFORMATION: C-terminal amide

<400> SEQUENCE: 9

His Xaa Val Gly Thr Phe Thr Ser Asp Lys Ser Lys Tyr Leu Asp Xaa
1               5                   10                  15

Arg Ala Ala Gln Asp Phe Val Gln Trp Leu Xaa Asp Thr
            20                  25

<210> SEQ ID NO 10
<211> LENGTH: 29
<212> TYPE: PRT
<213> ORGANISM: Artificial sequence
<220> FEATURE:
<223> OTHER INFORMATION: Co-agonist peptide 5
<220> FEATURE:
<221> NAME/KEY: MISC_FEATURE
<222> LOCATION: (2)..(2)
<223> OTHER INFORMATION: Xaa = D-Serine
<220> FEATURE:
<221> NAME/KEY: MISC_FEATURE
<222> LOCATION: (10)..(10)
<223> OTHER INFORMATION: Lysine conjugated to C16 via gamma-Glu
      gamma-Glu spacer
<220> FEATURE:
<221> NAME/KEY: MISC_FEATURE
<222> LOCATION: (29)..(29)
<223> OTHER INFORMATION: C-terminal amide

<400> SEQUENCE: 10

His Xaa Gln Gly Thr Phe Thr Ser Asp Lys Ser Lys Tyr Leu Asp Ala
```

```
                1               5                   10                  15
Arg Ala Ala Gln Asp Phe Val Gln Trp Leu Leu Asp Thr
            20                  25

<210> SEQ ID NO 11
<211> LENGTH: 29
<212> TYPE: PRT
<213> ORGANISM: Artificial sequence
<220> FEATURE:
<223> OTHER INFORMATION: Co-agonist peptide 6
<220> FEATURE:
<221> NAME/KEY: MISC_FEATURE
<222> LOCATION: (2)..(2)
<223> OTHER INFORMATION: Xaa = D-Serine
<220> FEATURE:
<221> NAME/KEY: MISC_FEATURE
<222> LOCATION: (10)..(10)
<223> OTHER INFORMATION: Lysine conjugated to C16 via gamma-Glu
      gamma-Glu spacer
<220> FEATURE:
<221> NAME/KEY: MISC_FEATURE
<222> LOCATION: (29)..(29)
<223> OTHER INFORMATION: C-terminal amide

<400> SEQUENCE: 11

His Xaa Gln Gly Thr Phe Thr Ser Asp Lys Ser Lys Tyr Leu Asp Glu
1               5                   10                  15

Arg Ala Ala Gln Asp Phe Val Gln Trp Leu Leu Asp Thr
            20                  25

<210> SEQ ID NO 12
<211> LENGTH: 29
<212> TYPE: PRT
<213> ORGANISM: Artificial sequence
<220> FEATURE:
<223> OTHER INFORMATION: Co-agonist peptide 7
<220> FEATURE:
<221> NAME/KEY: MISC_FEATURE
<222> LOCATION: (1)..(1)
<223> OTHER INFORMATION: N-terminal acetyl group
<220> FEATURE:
<221> NAME/KEY: MISC_FEATURE
<222> LOCATION: (10)..(10)
<223> OTHER INFORMATION: Lysine conjugated to C16 via gamma-Glu
      gamma-Glu spacer
<220> FEATURE:
<221> NAME/KEY: MISC_FEATURE
<222> LOCATION: (29)..(29)
<223> OTHER INFORMATION: C-terminal amide

<400> SEQUENCE: 12

His Ala Gln Gly Thr Phe Thr Ser Asp Lys Ser Lys Tyr Leu Asp Glu
1               5                   10                  15

Arg Ala Ala Gln Asp Phe Val Gln Trp Leu Leu Asp Thr
            20                  25

<210> SEQ ID NO 13
<211> LENGTH: 29
<212> TYPE: PRT
<213> ORGANISM: Artificial sequence
<220> FEATURE:
<223> OTHER INFORMATION: Co-agonist peptide 8
<220> FEATURE:
<221> NAME/KEY: MISC_FEATURE
<222> LOCATION: (2)..(2)
<223> OTHER INFORMATION: Xaa = D-Serine
<220> FEATURE:
<221> NAME/KEY: MISC_FEATURE
<222> LOCATION: (10)..(10)
<223> OTHER INFORMATION: Lysine conjugated to C16 via gamma-Glu
      gamma-Glu spacer
```

```
<220> FEATURE:
<221> NAME/KEY: MISC_FEATURE
<222> LOCATION: (29)..(29)
<223> OTHER INFORMATION: C-terminal amide

<400> SEQUENCE: 13

His Xaa Gln Gly Thr Phe Thr Ser Asp Lys Ser Lys Tyr Leu Glu Ala
1               5                   10                  15

Arg Ala Ala Gln Asp Phe Val Gln Trp Leu Leu Asp Thr
            20                  25

<210> SEQ ID NO 14
<211> LENGTH: 29
<212> TYPE: PRT
<213> ORGANISM: Artificial sequence
<220> FEATURE:
<223> OTHER INFORMATION: Co-agonist peptide 9
<220> FEATURE:
<221> NAME/KEY: MISC_FEATURE
<222> LOCATION: (2)..(2)
<223> OTHER INFORMATION: Xaa = D-Serine
<220> FEATURE:
<221> NAME/KEY: MISC_FEATURE
<222> LOCATION: (6)..(6)
<223> OTHER INFORMATION: Xaa = p-fluoro phenylalanine (pFF)
<220> FEATURE:
<221> NAME/KEY: MISC_FEATURE
<222> LOCATION: (10)..(10)
<223> OTHER INFORMATION: Lysine conjugated to C16 via gamma-Glu
     gamma-Glu spacer
<220> FEATURE:
<221> NAME/KEY: MISC_FEATURE
<222> LOCATION: (29)..(29)
<223> OTHER INFORMATION: C-terminal amide

<400> SEQUENCE: 14

His Xaa Gln Gly Thr Xaa Thr Ser Asp Lys Ser Lys Tyr Leu Asp Glu
1               5                   10                  15

Arg Ala Ala Gln Asp Phe Val Gln Trp Leu Leu Asp Thr
            20                  25

<210> SEQ ID NO 15
<211> LENGTH: 29
<212> TYPE: PRT
<213> ORGANISM: Artificial sequence
<220> FEATURE:
<223> OTHER INFORMATION: Co-agonist peptide 10
<220> FEATURE:
<221> NAME/KEY: MISC_FEATURE
<222> LOCATION: (2)..(2)
<223> OTHER INFORMATION: Xaa = D-Serine
<220> FEATURE:
<221> NAME/KEY: MISC_FEATURE
<222> LOCATION: (10)..(10)
<223> OTHER INFORMATION: Lysine conjugated to C16 via gamma-Glu
     gamma-Glu spacer
<220> FEATURE:
<221> NAME/KEY: MISC_FEATURE
<222> LOCATION: (27)..(27)
<223> OTHER INFORMATION: Xaa = methionine sulfone
<220> FEATURE:
<221> NAME/KEY: MISC_FEATURE
<222> LOCATION: (29)..(29)
<223> OTHER INFORMATION: C-terminal amide

<400> SEQUENCE: 15

His Xaa Gln Gly Thr Phe Thr Ser Asp Lys Ser Lys Tyr Leu Asp Glu
1               5                   10                  15

Arg Ala Ala Gln Asp Phe Val Gln Trp Leu Xaa Asp Thr
            20                  25
```

```
<210> SEQ ID NO 16
<211> LENGTH: 29
<212> TYPE: PRT
<213> ORGANISM: Artificial sequence
<220> FEATURE:
<223> OTHER INFORMATION: Co-agonist peptide 11
<220> FEATURE:
<221> NAME/KEY: MISC_FEATURE
<222> LOCATION: (2)..(2)
<223> OTHER INFORMATION: Xaa = D-Serine
<220> FEATURE:
<221> NAME/KEY: MISC_FEATURE
<222> LOCATION: (10)..(10)
<223> OTHER INFORMATION: Lysine conjugated to C16 via gamma-Glu
      gamma-Glu spacer
<220> FEATURE:
<221> NAME/KEY: MISC_FEATURE
<222> LOCATION: (29)..(29)
<223> OTHER INFORMATION: C-terminal amide

<400> SEQUENCE: 16

His Xaa Gln Gly Thr Phe Thr Ser Asp Lys Ser Leu Tyr Leu Asp Glu
1               5                   10                  15

Arg Ala Ala Gln Asp Phe Val Gln Trp Leu Leu Asp Thr
            20                  25

<210> SEQ ID NO 17
<211> LENGTH: 29
<212> TYPE: PRT
<213> ORGANISM: Artificial sequence
<220> FEATURE:
<223> OTHER INFORMATION: Co-agonist peptide 12
<220> FEATURE:
<221> NAME/KEY: MISC_FEATURE
<222> LOCATION: (2)..(2)
<223> OTHER INFORMATION: Xaa = D-Serine
<220> FEATURE:
<221> NAME/KEY: MISC_FEATURE
<222> LOCATION: (10)..(10)
<223> OTHER INFORMATION: Xaa = para-aminomethyl phenylalanine (pAF)
      conjugated to C16 via gamma-Glu gamma-Glu spacer
<220> FEATURE:
<221> NAME/KEY: MISC_FEATURE
<222> LOCATION: (29)..(29)
<223> OTHER INFORMATION: C-terminal amide

<400> SEQUENCE: 17

His Xaa Gln Gly Thr Phe Thr Ser Asp Xaa Ser Lys Tyr Leu Asp Ala
1               5                   10                  15

Arg Ala Ala Gln Asp Phe Val Gln Trp Leu Leu Asp Thr
            20                  25

<210> SEQ ID NO 18
<211> LENGTH: 29
<212> TYPE: PRT
<213> ORGANISM: Artificial sequence
<220> FEATURE:
<223> OTHER INFORMATION: Co-agonist peptide 13
<220> FEATURE:
<221> NAME/KEY: MISC_FEATURE
<222> LOCATION: (2)..(2)
<223> OTHER INFORMATION: Xaa = 1-amino-1-cyclobutane carboxylate
<220> FEATURE:
<221> NAME/KEY: MISC_FEATURE
<222> LOCATION: (10)..(10)
<223> OTHER INFORMATION: Lysine conjugated to C16 via gamma-Glu
      gamma-Glu spacer
<220> FEATURE:
<221> NAME/KEY: MISC_FEATURE
<222> LOCATION: (29)..(29)
<223> OTHER INFORMATION: C-terminal amide
```

-continued

<400> SEQUENCE: 18

His Xaa Gln Gly Thr Phe Thr Ser Asp Lys Ser Lys Tyr Leu Asp Glu
1               5                   10                  15

Arg Ala Ala Gln Asp Phe Val Gln Trp Leu Leu Asp Thr
            20                  25

<210> SEQ ID NO 19
<211> LENGTH: 29
<212> TYPE: PRT
<213> ORGANISM: Artificial sequence
<220> FEATURE:
<223> OTHER INFORMATION: Co-agonist peptide 14
<220> FEATURE:
<221> NAME/KEY: MISC_FEATURE
<222> LOCATION: (2)..(2)
<223> OTHER INFORMATION: Xaa = D-Serine
<220> FEATURE:
<221> NAME/KEY: MISC_FEATURE
<222> LOCATION: (6)..(6)
<223> OTHER INFORMATION: Xaa = threo-beta-phenylalanine
<220> FEATURE:
<221> NAME/KEY: MISC_FEATURE
<222> LOCATION: (10)..(10)
<223> OTHER INFORMATION: Lysine conjugated to C16 via gamma-Glu
      gamma-Glue spacer
<220> FEATURE:
<221> NAME/KEY: MISC_FEATURE
<222> LOCATION: (29)..(29)
<223> OTHER INFORMATION: C-terminal amide

<400> SEQUENCE: 19

His Xaa Gln Gly Thr Xaa Thr Ser Asp Lys Ser Lys Tyr Leu Asp Glu
1               5                   10                  15

Arg Ala Ala Gln Asp Phe Val Gln Trp Leu Leu Asp Thr
            20                  25

<210> SEQ ID NO 20
<211> LENGTH: 29
<212> TYPE: PRT
<213> ORGANISM: Artificial sequence
<220> FEATURE:
<223> OTHER INFORMATION: Co-agonist peptide 15
<220> FEATURE:
<221> NAME/KEY: MISC_FEATURE
<222> LOCATION: (1)..(1)
<223> OTHER INFORMATION: Optional N-terminal acetyl group
<220> FEATURE:
<221> NAME/KEY: MISC_FEATURE
<222> LOCATION: (2)..(2)
<223> OTHER INFORMATION: Xaa = D-Serine, L-Alanine, aib, or
      1-amino-cyclobutane carboylix acid
<220> FEATURE:
<221> NAME/KEY: MISC_FEATURE
<222> LOCATION: (6)..(6)
<223> OTHER INFORMATION: Xaa = L-Phenylalanine, p-fluoro phenylalanine,
      or threo-beta-phenylalanine
<220> FEATURE:
<221> NAME/KEY: MISC_FEATURE
<222> LOCATION: (10)..(10)
<223> OTHER INFORMATION: Lysine conjugated to C16 via gamma-Glu spacer
      or Lysine conjugated to C16 via gamma-Glu gamma-Glu spacer
<220> FEATURE:
<221> NAME/KEY: MISC_FEATURE
<222> LOCATION: (10)..(10)
<223> OTHER INFORMATION: Xaa = Lysine conjugated to C16 via gamma-Glu
      spacer, Lysine conjugated to C16 via gamma-Glu gamma-Glu spacer,
      or pAF conjugated to C16 via gamma-Glu gamma-Glu spacer
<220> FEATURE:
<221> NAME/KEY: MISC_FEATURE
<222> LOCATION: (12)..(12)
<223> OTHER INFORMATION: Xaa = L-Lysine or L-Leucine
<220> FEATURE:
<221> NAME/KEY: MISC_FEATURE

```
<222> LOCATION: (15)..(15)
<223> OTHER INFORMATION: Xaa = L-Glutamic acid, L-Leucine, or L-Aspartic
      acid
<220> FEATURE:
<221> NAME/KEY: MISC_FEATURE
<222> LOCATION: (16)..(16)
<223> OTHER INFORMATION: Xaa =aib, L-Alanine, L-Glutamic acid, or
      L-Valine
<220> FEATURE:
<221> NAME/KEY: MISC_FEATURE
<222> LOCATION: (18)..(18)
<223> OTHER INFORMATION: Xaa = L-Alanine or L-Arginine
<220> FEATURE:
<221> NAME/KEY: MISC_FEATURE
<222> LOCATION: (27)..(27)
<223> OTHER INFORMATION: Xaa = L-Leucine, methionine sulfone, or
      L-norleucine (Nle)
<220> FEATURE:
<221> NAME/KEY: MISC_FEATURE
<222> LOCATION: (29)..(29)
<223> OTHER INFORMATION: Optional C-terminal amide or ester

<400> SEQUENCE: 20

His Xaa Gln Gly Thr Xaa Thr Ser Asp Xaa Ser Xaa Tyr Leu Xaa Xaa
1               5                   10                  15

Arg Xaa Ala Gln Asp Phe Val Gln Trp Leu Xaa Asp Thr
            20                  25

<210> SEQ ID NO 21
<211> LENGTH: 29
<212> TYPE: PRT
<213> ORGANISM: Artificial sequence
<220> FEATURE:
<223> OTHER INFORMATION: Comparative peptide
<220> FEATURE:
<221> NAME/KEY: MISC_FEATURE
<222> LOCATION: (2)..(2)
<223> OTHER INFORMATION: Xaa = D-Serine
<220> FEATURE:
<221> NAME/KEY: MISC_FEATURE
<222> LOCATION: (29)..(29)
<223> OTHER INFORMATION: C-terminal amidation

<400> SEQUENCE: 21

His Xaa Gln Gly Thr Phe Thr Ser Asp Lys Ser Lys Tyr Leu Asp Glu
1               5                   10                  15

Arg Ala Ala Gln Asp Phe Val Gln Trp Leu Leu Asp Thr
            20                  25

<210> SEQ ID NO 22
<211> LENGTH: 29
<212> TYPE: PRT
<213> ORGANISM: Artificial sequence
<220> FEATURE:
<223> OTHER INFORMATION: C0-agonist peptide 16
<220> FEATURE:
<221> NAME/KEY: MISC_FEATURE
<222> LOCATION: (2)..(2)
<223> OTHER INFORMATION: Xaa = D-Serine
<220> FEATURE:
<221> NAME/KEY: MISC_FEATURE
<222> LOCATION: (10)..(10)
<223> OTHER INFORMATION: Lysine conjugated to C16 via gamma-Glu spacer
<220> FEATURE:
<221> NAME/KEY: MISC_FEATURE
<222> LOCATION: (29)..(29)
<223> OTHER INFORMATION: Optional C-terminal amide or ester

<400> SEQUENCE: 22

His Xaa Gln Gly Thr Phe Thr Ser Asp Lys Ser Lys Tyr Leu Asp Ala
1               5                   10                  15
```

Arg Ala Ala Gln Asp Phe Val Gln Trp Leu Leu Asp Thr
            20                  25

<210> SEQ ID NO 23
<211> LENGTH: 29
<212> TYPE: PRT
<213> ORGANISM: Artificial sequence
<220> FEATURE:
<223> OTHER INFORMATION: Co-agonist peptide 17
<220> FEATURE:
<221> NAME/KEY: MISC_FEATURE
<222> LOCATION: (2)..(2)
<223> OTHER INFORMATION: Xaa = D-Serine
<220> FEATURE:
<221> NAME/KEY: MISC_FEATURE
<222> LOCATION: (10)..(10)
<223> OTHER INFORMATION: Lysine conjugated to C16 via gamma-Glu
      gamma-Glu spacer
<220> FEATURE:
<221> NAME/KEY: MISC_FEATURE
<222> LOCATION: (29)..(29)
<223> OTHER INFORMATION: Optional C-terminal amide or ester

<400> SEQUENCE: 23

His Xaa Gln Gly Thr Phe Thr Ser Asp Lys Ser Lys Tyr Leu Asp Val
1               5                   10                  15

Arg Arg Ala Gln Asp Phe Val Gln Trp Leu Leu Asp Thr
            20                  25

<210> SEQ ID NO 24
<211> LENGTH: 29
<212> TYPE: PRT
<213> ORGANISM: Artificial sequence
<220> FEATURE:
<223> OTHER INFORMATION: Co-agonist peptide 18
<220> FEATURE:
<221> NAME/KEY: MISC_FEATURE
<222> LOCATION: (2)..(2)
<223> OTHER INFORMATION: Xaa = D-Serine
<220> FEATURE:
<221> NAME/KEY: MISC_FEATURE
<222> LOCATION: (10)..(10)
<223> OTHER INFORMATION: Lysine conjugated to C16 via gamma-Glu
      gamma-Glu spacer
<220> FEATURE:
<221> NAME/KEY: MISC_FEATURE
<222> LOCATION: (29)..(29)
<223> OTHER INFORMATION: Optional C-terminal amide or ester

<400> SEQUENCE: 24

His Xaa Gln Gly Thr Phe Thr Ser Asp Lys Ser Lys Tyr Leu Asp Val
1               5                   10                  15

Arg Ala Ala Gln Asp Phe Val Gln Trp Leu Leu Asp Thr
            20                  25

<210> SEQ ID NO 25
<211> LENGTH: 29
<212> TYPE: PRT
<213> ORGANISM: Artificial sequence
<220> FEATURE:
<223> OTHER INFORMATION: Co-agonist peptide 19
<220> FEATURE:
<221> NAME/KEY: MISC_FEATURE
<222> LOCATION: (2)..(2)
<223> OTHER INFORMATION: Xaa = alpha-aminoisobutyric acid (aib)
<220> FEATURE:
<221> NAME/KEY: MISC_FEATURE
<222> LOCATION: (10)..(10)
<223> OTHER INFORMATION: Lysine conjugated to C16 via gamma-Glu
      gamma-Glu spacer
<220> FEATURE:
<221> NAME/KEY: MISC_FEATURE

```
<222> LOCATION: (16)..(16)
<223> OTHER INFORMATION: Xaa = alpha-aminoisobutyric acid (aib)
<220> FEATURE:
<221> NAME/KEY: MISC_FEATURE
<222> LOCATION: (27)..(27)
<223> OTHER INFORMATION: Xaa = L-norleucine (Nle)
<220> FEATURE:
<221> NAME/KEY: MISC_FEATURE
<222> LOCATION: (29)..(29)
<223> OTHER INFORMATION: Optional C-terminal amide or ester

<400> SEQUENCE: 25

His Xaa Val Gly Thr Phe Thr Ser Asp Lys Ser Lys Tyr Leu Asp Xaa
1               5                   10                  15
Arg Ala Ala Gln Asp Phe Val Gln Trp Leu Xaa Asp Thr
            20                  25

<210> SEQ ID NO 26
<211> LENGTH: 29
<212> TYPE: PRT
<213> ORGANISM: artificial
<220> FEATURE:
<223> OTHER INFORMATION: Co-agonist peptide 20
<220> FEATURE:
<221> NAME/KEY: MISC_FEATURE
<222> LOCATION: (2)..(2)
<223> OTHER INFORMATION: Xaa = D-Serine
<220> FEATURE:
<221> NAME/KEY: MISC_FEATURE
<222> LOCATION: (10)..(10)
<223> OTHER INFORMATION: Lysine conjugated to C16 via gamma-Glu
      gamma-Glu spacer
<220> FEATURE:
<221> NAME/KEY: MISC_FEATURE
<222> LOCATION: (29)..(29)
<223> OTHER INFORMATION: Optional C-terminal amide or ester

<400> SEQUENCE: 26

His Xaa Gln Gly Thr Phe Thr Ser Asp Lys Ser Lys Tyr Leu Asp Ala
1               5                   10                  15
Arg Ala Ala Gln Asp Phe Val Gln Trp Leu Leu Asp Thr
            20                  25

<210> SEQ ID NO 27
<211> LENGTH: 29
<212> TYPE: PRT
<213> ORGANISM: Artificial sequence
<220> FEATURE:
<223> OTHER INFORMATION: Co-agonist peptide 21
<220> FEATURE:
<221> NAME/KEY: MISC_FEATURE
<222> LOCATION: (2)..(2)
<223> OTHER INFORMATION: Xaa = D-Serine
<220> FEATURE:
<221> NAME/KEY: MISC_FEATURE
<222> LOCATION: (10)..(10)
<223> OTHER INFORMATION: Lysine conjugated to C16 via gamma-Glu
      gamma-Glu spacer
<220> FEATURE:
<221> NAME/KEY: MISC_FEATURE
<222> LOCATION: (29)..(29)
<223> OTHER INFORMATION: Optional C-terminal amide or ester

<400> SEQUENCE: 27

His Xaa Gln Gly Thr Phe Thr Ser Asp Lys Ser Lys Tyr Leu Asp Glu
1               5                   10                  15
Arg Ala Ala Gln Asp Phe Val Gln Trp Leu Leu Asp Thr
            20                  25

<210> SEQ ID NO 28
```

```
<211> LENGTH: 29
<212> TYPE: PRT
<213> ORGANISM: Artificial sequence
<220> FEATURE:
<223> OTHER INFORMATION: Co-agonist peptide 22
<220> FEATURE:
<221> NAME/KEY: MISC_FEATURE
<222> LOCATION: (1)..(1)
<223> OTHER INFORMATION: N-terminal acetyl group
<220> FEATURE:
<221> NAME/KEY: MISC_FEATURE
<222> LOCATION: (10)..(10)
<223> OTHER INFORMATION: Lysine conjugated to C16 via gamma-Glu
      gamma-Glu spacer
<220> FEATURE:
<221> NAME/KEY: MISC_FEATURE
<222> LOCATION: (29)..(29)
<223> OTHER INFORMATION: Optional C-terminal amide or ester

<400> SEQUENCE: 28

His Ala Gln Gly Thr Phe Thr Ser Asp Lys Ser Lys Tyr Leu Asp Glu
1               5                   10                  15

Arg Ala Ala Gln Asp Phe Val Gln Trp Leu Leu Asp Thr
            20                  25

<210> SEQ ID NO 29
<211> LENGTH: 29
<212> TYPE: PRT
<213> ORGANISM: Artificial sequence
<220> FEATURE:
<223> OTHER INFORMATION: Co-agonist peptide 23
<220> FEATURE:
<221> NAME/KEY: MISC_FEATURE
<222> LOCATION: (2)..(2)
<223> OTHER INFORMATION: Xaa = D-Serine
<220> FEATURE:
<221> NAME/KEY: MISC_FEATURE
<222> LOCATION: (10)..(10)
<223> OTHER INFORMATION: Lysine conjugated to C16 via gamma-Glu
      gamma-Glu spacer
<220> FEATURE:
<221> NAME/KEY: MISC_FEATURE
<222> LOCATION: (29)..(29)
<223> OTHER INFORMATION: Optioanl C-terminal amide or ester

<400> SEQUENCE: 29

His Xaa Gln Gly Thr Phe Thr Ser Asp Lys Ser Lys Tyr Leu Glu Ala
1               5                   10                  15

Arg Ala Ala Gln Asp Phe Val Gln Trp Leu Leu Asp Thr
            20                  25

<210> SEQ ID NO 30
<211> LENGTH: 29
<212> TYPE: PRT
<213> ORGANISM: Artificial sequence
<220> FEATURE:
<223> OTHER INFORMATION: Co-agonist peptide 24
<220> FEATURE:
<221> NAME/KEY: MISC_FEATURE
<222> LOCATION: (2)..(2)
<223> OTHER INFORMATION: Xaa = D-Serine
<220> FEATURE:
<221> NAME/KEY: MISC_FEATURE
<222> LOCATION: (6)..(6)
<223> OTHER INFORMATION: Xaa = p-fluoro phenylalanine (pFF)
<220> FEATURE:
<221> NAME/KEY: MISC_FEATURE
<222> LOCATION: (10)..(10)
<223> OTHER INFORMATION: Lysine conjugated to C16 via gamma-Glu
      gamma-Glu spacer
<220> FEATURE:
<221> NAME/KEY: MISC_FEATURE
<222> LOCATION: (29)..(29)
```

<223> OTHER INFORMATION: Optional C-terminal amide or ester

<400> SEQUENCE: 30

His Xaa Gln Gly Thr Xaa Thr Ser Asp Lys Ser Lys Tyr Leu Asp Glu
1               5                   10                  15

Arg Ala Ala Gln Asp Phe Val Gln Trp Leu Leu Asp Thr
            20                  25

<210> SEQ ID NO 31
<211> LENGTH: 29
<212> TYPE: PRT
<213> ORGANISM: Artificial sequence
<220> FEATURE:
<223> OTHER INFORMATION: Co-agonist peptide 25
<220> FEATURE:
<221> NAME/KEY: MISC_FEATURE
<222> LOCATION: (2)..(2)
<223> OTHER INFORMATION: Xaa = D-Serine
<220> FEATURE:
<221> NAME/KEY: MISC_FEATURE
<222> LOCATION: (10)..(10)
<223> OTHER INFORMATION: Lysine conjugated to C16 via gamma--Glu
      gamma-Glu spacer
<220> FEATURE:
<221> NAME/KEY: MISC_FEATURE
<222> LOCATION: (27)..(27)
<223> OTHER INFORMATION: Xaa = methionine sulfone
<220> FEATURE:
<221> NAME/KEY: MISC_FEATURE
<222> LOCATION: (29)..(29)
<223> OTHER INFORMATION: Optional C-terminal amide or ester

<400> SEQUENCE: 31

His Xaa Gln Gly Thr Phe Thr Ser Asp Lys Ser Lys Tyr Leu Asp Glu
1               5                   10                  15

Arg Ala Ala Gln Asp Phe Val Gln Trp Leu Xaa Asp Thr
            20                  25

<210> SEQ ID NO 32
<211> LENGTH: 29
<212> TYPE: PRT
<213> ORGANISM: Artificial sequence
<220> FEATURE:
<223> OTHER INFORMATION: Co-agonist peptide 26
<220> FEATURE:
<221> NAME/KEY: MISC_FEATURE
<222> LOCATION: (2)..(2)
<223> OTHER INFORMATION: Xaa = D-Serine
<220> FEATURE:
<221> NAME/KEY: MISC_FEATURE
<222> LOCATION: (10)..(10)
<223> OTHER INFORMATION: Lysine conjugated to C16 via gamma-Glu
      gamma-Glu spacer
<220> FEATURE:
<221> NAME/KEY: MISC_FEATURE
<222> LOCATION: (29)..(29)
<223> OTHER INFORMATION: Optional C-terminal amide or ester

<400> SEQUENCE: 32

His Xaa Gln Gly Thr Phe Thr Ser Asp Lys Ser Leu Tyr Leu Asp Glu
1               5                   10                  15

Arg Ala Ala Gln Asp Phe Val Gln Trp Leu Leu Asp Thr
            20                  25

<210> SEQ ID NO 33
<211> LENGTH: 29
<212> TYPE: PRT
<213> ORGANISM: Artificial sequence
<220> FEATURE:
<223> OTHER INFORMATION: C0oagonist peptide 27

```
<220> FEATURE:
<221> NAME/KEY: MISC_FEATURE
<222> LOCATION: (2)..(2)
<223> OTHER INFORMATION: Xaa = D-Serine
<220> FEATURE:
<221> NAME/KEY: MISC_FEATURE
<222> LOCATION: (10)..(10)
<223> OTHER INFORMATION: Xaa = para-aminomethyl phenylalanine 9pAF)
      conjugaed to C16 via gamma-Glu gamma-Glu spacer
<220> FEATURE:
<221> NAME/KEY: MISC_FEATURE
<222> LOCATION: (29)..(29)
<223> OTHER INFORMATION: Optional C-terminal amide or ester

<400> SEQUENCE: 33

His Xaa Gln Gly Thr Phe Thr Ser Asp Xaa Ser Lys Tyr Leu Asp Ala
1               5                   10                  15

Arg Ala Ala Gln Asp Phe Val Gln Trp Leu Leu Asp Thr
            20                  25

<210> SEQ ID NO 34
<211> LENGTH: 29
<212> TYPE: PRT
<213> ORGANISM: Artificial sequence
<220> FEATURE:
<223> OTHER INFORMATION: Co-agonist peptide 28
<220> FEATURE:
<221> NAME/KEY: MISC_FEATURE
<222> LOCATION: (2)..(2)
<223> OTHER INFORMATION: Xaa = 1-amino-1-cyclobutane carboxylic acid
<220> FEATURE:
<221> NAME/KEY: MISC_FEATURE
<222> LOCATION: (10)..(10)
<223> OTHER INFORMATION: Lysine conjugated to C16 via gamma-Glu
      gamma-Glu spacer
<220> FEATURE:
<221> NAME/KEY: MISC_FEATURE
<222> LOCATION: (29)..(29)
<223> OTHER INFORMATION: Optional C-terminal amide or ester

<400> SEQUENCE: 34

His Xaa Gln Gly Thr Phe Thr Ser Asp Lys Ser Lys Tyr Leu Asp Glu
1               5                   10                  15

Arg Ala Ala Gln Asp Phe Val Gln Trp Leu Leu Asp Thr
            20                  25

<210> SEQ ID NO 35
<211> LENGTH: 29
<212> TYPE: PRT
<213> ORGANISM: Artificial sequence
<220> FEATURE:
<223> OTHER INFORMATION: Co-agonist peptide 29
<220> FEATURE:
<221> NAME/KEY: MISC_FEATURE
<222> LOCATION: (2)..(2)
<223> OTHER INFORMATION: Xaa = D-Serine
<220> FEATURE:
<221> NAME/KEY: MISC_FEATURE
<222> LOCATION: (6)..(6)
<223> OTHER INFORMATION: Xaa = threo-beta-phenylserine
<220> FEATURE:
<221> NAME/KEY: MISC_FEATURE
<222> LOCATION: (10)..(10)
<223> OTHER INFORMATION: Lysine conjugated to C16 via gamma-Glu
      gamma-Glu spacer
<220> FEATURE:
<221> NAME/KEY: MISC_FEATURE
<222> LOCATION: (29)..(29)
<223> OTHER INFORMATION: Optional C-terminal amide or ester

<400> SEQUENCE: 35

His Xaa Gln Gly Thr Xaa Thr Ser Asp Lys Ser Lys Tyr Leu Asp Glu
```

-continued

```
 1               5              10              15
Arg Ala Ala Gln Asp Phe Val Gln Trp Leu Leu Asp Thr
                20              25
```

CO-AGONISTS OF THE GLUCAGON AND GLP-1 RECEPTORS

CROSS REFERENCE TO RELATED APPLICATIONS

This is the U.S. National Stage of International Application No. PCT/US2015/056794 filed Oct. 22, 2015, which was published in English under PCT Article 21(2), which in turn claims the benefit of U.S. Provisional Application Ser. No. 62/208,869 filed Aug. 24, 2015, and U.S. Provisional Application Ser. No. 62/068,157 filed Oct. 24, 2014, all of which are incorporated herein by reference in their entireties.

BACKGROUND OF THE INVENTION

(1) Field of the Invention

The present invention relates to peptide analogs of glucagon, which have been modified to be resistant to cleavage and inactivation by dipeptidyl peptidase IV (DPP-IV) and to increase in vivo half-life of the peptide analog while enabling the peptide analog to have relatively balanced agonist activity at the glucagon-like peptide 1 (GLP-1) receptor and the glucagon (GCG) receptor, and the use of such GLP-1 receptor/GCG receptor co-agonists for treatment of metabolic disorders such as diabetes, non-alcoholic fatty liver disease (NAFLD), non-alcoholic steatohepatitis (NASH), and obesity.

(2) Description of Related Art

Pre-proglucagon is a 158 amino acid precursor polypeptide that is processed in different tissues to form a number of different proglucagon-derived peptides, including glucagon, glucagon-like peptide-1 (GLP-1), glucagon-like peptide-2 (GLP-2) and oxyntomodulin (OXM), that are involved in a wide variety of physiological functions, including glucose homeostasis, insulin secretion, gastric emptying, and intestinal growth, as well as the regulation of food intake. Glucagon is a 29-amino acid peptide that corresponds to amino acids 33 through 61 of pre-proglucagon, while GLP-1 is produced as a 37-amino acid peptide that corresponds to amino acids 72 through 108 of pre-proglucagon. GLP-1 (7-36) amide or GLP-1 (7-37) acid are biologically potent forms of GLP-1, that demonstrate essentially equivalent activity at the GLP-1 receptor.

During hypoglycemia, when blood glucose levels drop below normal, glucagon signals the liver to break down glycogen and release glucose, causing blood glucose levels to rise toward a normal level. Hypoglycemia is a common side effect of insulin therapy in patients with hyperglycemia (elevated blood glucose levels) due to diabetes. Thus, glucagon's most recognized role in glucose regulation is to counteract the action of insulin and maintain blood glucose levels.

GLP-1 has different biological activities compared to glucagon. Its actions include stimulation of insulin synthesis and secretion, inhibition of glucagon secretion, and inhibition of food intake. GLP-1 has been shown to reduce hyperglycemia in diabetics. Exendin-4, a peptide from lizard venom that shares about 50% amino acid identity with GLP-1, activates the GLP-1 receptor and likewise has been shown to reduce hyperglycemia in diabetics.

There is also evidence that GLP-1 and exendin-4 may reduce food intake and promote weight loss, an effect that would be beneficial not only for diabetics but also for patients suffering from obesity. Patients with obesity have a higher risk of diabetes, hypertension, hyperlipidemia, cardiovascular disease, and musculoskeletal diseases.

Glucagon is a peptide hormone structurally related to GLP-1 that is well recognized for its acute ability to increase blood glucose through stimulation of glycogenolysis and gluconeogenesis (Jiang & Zhang, Am. J. Physiol. Endocrinol. Metab. 284: E671-E678 (2003)). Of lesser appreciation are the chronic effects of glucagon pharmacology characterized by increases in thermogenesis, satiety, lipolysis, fatty acid oxidation, and ketogenesis (Habegger et al., Nat. Rev. Endocrinol. 6: 689-697 (2010)). Repeated administration of glucagon was first reported decades ago to yield improvements in rodent metabolism, accompanied with lower body weight (Salter, Am. J. Clin. Nutr. 8: 535-539 (1960)). Nonetheless, the inherent risk of hyperglycemia, especially in insulinresistant states such T2DM, has complicated the translation of these observations to human study.

The hormone oxyntomodulin (OXM, glucagon-37) is a posttranslational product of preproglucagon processing in the intestine and central nervous system (CNS) and is secreted from L-cells in the gut in response to food intake. Discovered in 1983, OXM has been implicated in the regulation of food intake and energy expenditure (Jarrouse et al., Endocrinol. 115: 102-105 (1984); Schjoldager et al., Eur. J. Clin. Invest., 18: 499-503 (1988)). Central or peripheral administration of OXM in rats causes a decrease in short term food intake with minimal effects on gastric emptying (Dakin et al. Endocrinology, 142: 4244-4250 (2001), Dakin et al. Endocrinology, 145: 2687-2695 (2004)). Repeated intracerebroventricular administration of OXM in rats results in elevated core temperatures and reduced weight gain compared to pair-fed animals, suggesting effects on both caloric intake and energy expenditure (Dakin et al. Am. J. Physiol. Endocrinol. Metab., 283: E1173-E1177 (2002)).

In related studies, peripheral administration of OXM dose-dependently inhibited both fast-induced and dark phase food intake, but unlike GLP-1, had no effect on gastric emptying. OXM also reduced levels of fasting ghrelin and increased c-fos immunoreactivity, in the arcuate nucleus (ARC). Repeated seven-day IP administration of OXM caused a reduction in the rate of body weight gain and adiposity in rats (See Dakin et al. Endocrinology, 145: 2687-2695 (2004)).

Studies of OXM action in mice have demonstrated that although OXM can activate both the glucagon (GCG) and the GLP-1 receptors, the anorectic actions of OXM require only the GLP-1 receptor, as icy OXM inhibits food intake in glucagon receptor knockout mice. However, the anorectic effects of OXM are completely absent in GLP-1 receptor knockout mice. Furthermore, exendin-4, but not OXM, regulates energy expenditure in mice. Hence, OXM appears to be a weak agonist at the GLP-1 receptor, when used in pharmacological concentrations (See Baggio et al., Gastroenterol. 127: 546-58 (2004)). OXM was also found to ameliorate glucose intolerance in mice fed a high fat diet (Dakin et al., Am. J. Physiol. Endocrinol. Metab. 294: E142-E147 (2008) and increase the intrinsic heart rate in mice independent of the GLP-1 receptor (Sowden et al., Am. J. Physiol. Regul. Integr. Comp. Physiol. 292: R962-R970 (2007). OXM has also been shown to differentially affect GLP-1 receptor beta-arrestin recruitment and signaling through Galpha (Jorgensen et al., J. Pharma. Exp. Therapeut. 322: 148-154 (2007)) and to differentially affect hypothalamic neuronal activation following peripheral injection of OXM (Choudhri et al., Biochem. Biophys. Res. Commun. 350: 298-306 (2006)).

In humans, a single 90 minute intravenous infusion of OXM in normal weight healthy subjects reduced hunger scores and food intake at a buffet meal by about 19%. Cumulative twelve-hour caloric intake was reduced by about 11% with no reports of nausea or changes in food palatability (Cohen et al., J. Clin. Endocrinol. Metab., 88: 4696-4701 (2003); Lykkegaard et al., ADA Scientific Sessions, Abstract #1506-P (2003)). More recently, pre-prandial injections of OXM over a four-week period in obese healthy volunteers (BMI about 33) led to a significant reduction of caloric intake on the first day of treatment (about 25%) that was maintained over the course of the study (35% reduction after four weeks) (Wynne et al., Diabetes 54: 2390-2395 (2005)). Robust weight loss was observed at the end of the study in treated subjects (1.9%, placebo-corrected). Plasma levels of OXM were similar to that observed in the infusion study (peak concentration about 950 pM). The absence of any tachyphylaxis and a low incidence of mild and transient nausea (about 3%) despite the relatively high doses necessitated by the poor in vivo stability of OXM (plasma t½<12 minutes) renders this hormone one of the few obesity targets with both human validation and an attractive tolerability profile.

OXM has a very short half-life and is rapidly inactivated by the cell surface dipeptidyl peptidase IV (DPP-IV) (Zhu et al., J. Biol. Chem. 278: 22418-22423 (2002). However, DPP-IV inhibitors are weight-neutral in the clinic, suggesting that supraphysiological levels of OXM (900-1000 pM) may be required to achieve weight loss in humans. OXM peptide analogs for inducing weight loss in humans have been the object of Published International Application Nos. WO03/022304, WO2004/062685, WO2006/134340, and WO2010/096052.

Recently, two independent and simultaneous papers reported the use of relatively balanced GLP-1 receptor/GCG receptor co-agonists as being of enhanced efficacy and safety relative to pure GLP1R agonists in the treatment of rodent obesity, with simultaneous improvement in glycemic control (Day et al., Nat. Chem. Biol. 5: 749-757 (2009); Pocai eta al., Diabetes 58: 2258-2266 (2009)). Of related significance is work with oxyntomodulin (OXM), an endogenous precursor to glucagon, which is secreted postprandially by L-cells of the jejuno-ileum together with GLP-1 (Holst, Regul. Pept. 93: 45-51 (2000); Drucker, Nat. Clin. Pract. Endocrinol. Metab. 1: 22-31 (2005).

Glucagon peptide analogs and derivatives modified to have various degrees of activity at the GLP-1 receptor and GCG receptor have been disclosed in Published International Application Nos. WO2008/101017, WO2009/155258, WO2011/075393, WO2012/177444, and WO2012/177443. Some of the disclosed glucagon peptide analogs were reported therein to have activity at both the GLP-1 receptor and GCG receptor; however, there remains a need for coagonist peptides that have relatively balanced activity or potency at the GLP-1 receptor and GCG receptor.

BRIEF SUMMARY OF THE INVENTION

The invention provides peptides that are agonists of the glucagon (GCG) receptor and the glucagon-like peptide 1 (GLP-1) receptor and have a relatively balanced activity or potency at both receptors. Native glucagon normally has about 1% of the activity of native GLP-1 at the GLP-1 receptor. However, the GCG receptor/GLP-1 receptor co-agonist peptides of the invention have relatively balanced activity or potency at the GCG receptor and GLP-1 receptor. In particular aspects, the GCG receptor/GLP-1 receptor co-agonist peptides have an $EC_{50}$ of about 0.02 to about 1.04 nM at the GCG receptor and an $EC_{50}$ of about 0.03 to about 1.3 nM at the GLP-1 receptor. In particular aspects, the GCG receptor/GLP-1 receptor co-agonist peptides have a ratio of $EC_{50}$ at the glucagon receptor to $EC_{50}$ at the GLP-1 receptor of about 0.88 to about 1.25, about 0.90 to about 1.25, about 0.90 to about 1.10, about 0.90 to about 1.00, or about 1.0±0.12. The peptides herein are useful for the treatment of metabolic disorders, such as but not limited to, diabetes (e.g., type 1 diabetes, Type 2 diabetes, or gestational diabetes), non-alcoholic fatty liver disease (NAFLD), non-alcoholic steatohepatitis (NASH), and/or obesity.

In a general embodiment, the GCG receptor/GLP-1 receptor co-agonist peptides of the present invention comprise the amino acid sequence of native human glucagon (SEQ ID NO:1) but in which the L-serine at position 2 is replaced with a D-serine, L-alanine, α-aminoisobutyric acid (Aib), or 1-amino-cyclobutane carboxylic acid; the tyrosine at position 10 is replaced with (i) L-lysine conjugated to a palmitoyl group by either a gamma-glutamic acid (γE) spacer or a gamma-glutamic acid-gamma-glutamic acid dipeptide (γEγE) spacer or (ii) para-aminomethyl phenylalanine conjugated to a palmitoyl group by either a gamma-glutamic acid (γE) spacer or a gamma-glutamic acid-gamma-glutamic acid dipeptide (γEγE) spacer; and may include up to six additional amino acid substitutions; wherein GCG receptor/GLP-1 receptor co-agonist peptides have a relatively balanced activity at the GCG receptor and GLP-1 receptor, and optionally a protecting group that, if present, is joined to the C-terminal carboxy group of the peptide with the proviso that the peptide does not have the amino acid sequence of SEQ ID NO:21.

In particular embodiments, the present invention provides a peptide comprising the amino acid sequence (SEQ ID NO: 20)
$HX_2QGTX_6TSDX_{10}SX_{12}YLX_{15}X_{16}RX_{18}AQDFVQWLX_{27}DT$ Wherein $X_2$ is D-serine, L-alanine, α-aminoisobutyric acid (Aib), or 1-amino-cyclobutane carboxylic acid; $X_6$ is L-phenylalanine, para-fluoro phenylalanine or threo-β-phenylserine; $X_{10}$ is L-lysine or para-aminomethyl phenylalanine; $X_{12}$ is L-lysine or L-leucine; $X_{15}$ is L-glutamic acid or L-leucine; $X_{16}$ is L-alanine, Aib, L-glutamic acid, or L-valine; $X_{18}$ is L-alanine or L-arginine; $X_{27}$ is L-leucine, methionine sulfone, or L-norleucine; the amino acid at position 10 is conjugated to a palmitoyl group by either a gamma-glutamic acid (γE) spacer or a gamma-glutamic acid-gamma-glutamic acid dipeptide (γEγE) spacer; and, the peptide optionally includes a protecting group that, if present, is joined to the C-terminal carboxy group of the peptide; with the proviso that the peptide does not have the amino acid sequence of SEQ ID NO:21.

In particular embodiments, the peptide has the amino acid sequence of SEQ ID NO:7, 8, 9, 10, 12, 13, 14, 15, 16, 17, 18, or 19.

In particular embodiments, the peptide is an co-agonist of the glucagon receptor and the GLP-1 receptor and has a ratio of $EC_{50}$ at the glucagon receptor to $EC_{50}$ at the GLP-1 receptor of about 0.88 to about 1.25, about 0.90 to about 1.25, about 0.90 to about 1.10, about 0.90 to about 1.00, or about 1.0±0.12.

In particular embodiments, the peptide is an co-agonist of the glucagon receptor and the GLP-1 receptor and has a ratio of $EC_{50}$ at the glucagon receptor to $EC_{50}$ at the GLP-1 receptor of 0.88, 0.89, 0.90, 0.91, 0.92, 0.93, 0.94, 0.95, 0.96, 0.97, 0.98, 0.99, 1.00, 1.01, 1.02, 1.03, 1.04, 1.05, 1.06, 1.07, 1.08, 1.09, or 1.10.

The present invention further provides a composition comprising a peptide having the amino acid sequence (SEQ ID NO: 20)
HX$_2$QGTX$_6$TSDX$_{10}$SX$_{12}$YLX$_{15}$X$_{16}$RX$_{18}$AQDFVQWLX$_{27}$DT Wherein X$_2$ is D-serine, L-alanine, α-aminoisobutyric acid (Aib), or 1-amino-cyclobutane carboxylic acid; X$_6$ is L-phenylalanine, para-fluoro phenylalanine or threo-β-phenylserine; X$_{10}$ is L-lysine or para-aminomethyl phenylalanine; X$_{12}$ is L-lysine or L-leucine; X$_{15}$ is L-glutamic acid or L-leucine; X$_{16}$ is L-alanine, Aib, L-glutamic acid, or L-valine; X$_{18}$ is L-alanine or L-arginine; X$_{27}$ is L-leucine, methionine sulfone, or L-norleucine; the amino acid at position 10 is conjugated to a palmitoyl group by either a gamma-glutamic acid spacer (γE) or a gamma-glutamic acid-gamma-glutamic acid dipeptide (γEγE) spacer; the peptide optionally includes a protecting group that, if present, is joined to the C-terminal carboxy group of the peptide; and, a pharmaceutically acceptable carrier; with the proviso that the peptide does not have the amino acid sequence of SEQ ID NO:21.

In particular embodiments, the peptide has the amino acid sequence of SEQ ID NO:7, 8, 9, 10, 12, 13, 14, 15, 16, 17, 18, or 19.

In particular embodiments, the peptide is an co-agonist of the glucagon receptor and the GLP-1 receptor and has a ratio of $EC_{50}$ at the glucagon receptor to $EC_{50}$ at the GLP-1 receptor of about 0.88 to about 1.25, about 0.90 to about 1.25, about 0.90 to about 1.10, about 0.90 to about 1.00, or about 1.0±0.12.

In particular embodiments, the peptide is an co-agonist of the glucagon receptor and the GLP-1 receptor and has a ratio of $EC_{50}$ at the glucagon receptor to $EC_{50}$ at the GLP-1 receptor of 0.88, 0.89, 0.90, 0.91, 0.92, 0.93, 0.94, 0.95, 0.96, 0.97, 0.98, 0.99, 1.00, 1.01, 1.02, 1.03, 1.04, 1.05, 1.06, 1.07, 1.08, 1.09, or 1.10.

The present invention further provides a pharmaceutical composition comprising a peptide having the amino acid sequence (SEQ ID NO: 20)
HX$_2$QGTX$_6$TSDX$_{10}$SX$_{12}$YLX$_{15}$X$_{16}$RX$_{18}$AQDFVQWLX$_{27}$DT Wherein X$_2$ is D-serine, L-alanine, α-aminoisobutyric acid (Aib), or 1-amino-cyclobutane carboxylic acid; X$_6$ is L-phenylalanine, para-fluoro phenylalanine or threo-β-phenylserine; X$_{10}$ is L-lysine or para-aminomethyl phenylalanine; X$_{12}$ is L-lysine or L-leucine; X$_{15}$ is L-glutamic acid or L-leucine; X$_{16}$ is L-alanine, Aib, L-glutamic acid, or L-valine; X$_{18}$ is L-alanine or L-arginine; X$_{27}$ is L-leucine, methionine sulfone, or L-norleucine; the amino acid at position 10 is conjugated to a palmitoyl group by either a gamma-glutamic acid (γE) spacer or a gamma-glutamic acid-gamma-glutamic acid dipeptide (γEγE) spacer; the peptide optionally includes a protecting group that, if present, is joined to the C-terminal carboxy group of the peptide; and, a pharmaceutically acceptable carrier; with the proviso that the peptide does not have the amino acid sequence of SEQ ID NO:21.

In particular embodiments, the peptide has the amino acid sequence of SEQ ID NO:7, 8, 9, 10, 12, 13, 14, 15, 16, 17, 18, or 19.

In particular embodiments, the peptide is an co-agonist of the glucagon receptor and the GLP-1 receptor and has a ratio of $EC_{50}$ at the glucagon receptor to $EC_{50}$ at the GLP-1 receptor of about 0.88 to about 1.25, about 0.90 to about 1.25, about 0.90 to about 1.10, about 0.90 to about 1.00, or about 1.0±0.12.

In particular embodiments, the peptide is an co-agonist of the glucagon receptor and the GLP-1 receptor and has a ratio of $EC_{50}$ at the glucagon receptor to $EC_{50}$ at the GLP-1 receptor of 0.88, 0.89, 0.90, 0.91, 0.92, 0.93, 0.94, 0.95, 0.96, 0.97, 0.98, 0.99, 1.00, 1.01, 1.02, 1.03, 1.04, 1.05, 1.06, 1.07, 1.08, 1.09, or 1.10.

The present invention further provides a peptide comprising the amino acid sequence of native human glucagon having the amino acid sequence shown in SEQ ID NO:1 but in which the L-serine at position 2 is replaced with a D-serine; the tyrosine at position 10 is replaced with (i) L-lysine conjugated to a palmitoyl group by either a gamma-glutamic acid (γE) spacer or a gamma-glutamic acid-gamma-glutamic acid dipeptide (γEγE) spacer or (ii) para-aminomethyl phenylalanine conjugated to a palmitoyl group by either a gamma-glutamic acid (γE) spacer or a gamma-glutamic acid-gamma-glutamic acid dipeptide (γEγE) spacer; and up to six additional amino acid substitutions; wherein the peptide is an co-agonist of the glucagon receptor and the GLP-1 receptor and has a ratio of $EC_{50}$ at the glucagon receptor to $EC_{50}$ at the GLP-1 receptor of about 0.88 to about 1.25, about 0.90 to about 1.25, about 0.90 to about 1.10, about 0.90 to about 1.00, or about 1.0±0.12, and wherein the peptide optionally includes a protecting group that, if present, is joined to the C-terminal carboxy group of the peptide; with the proviso that the peptide does not have the amino acid sequence of SEQ ID NO:21.

In particular aspects, the serine at position 16 is replaced with D-alanine or L-alanine, the arginine at position 18 is replaced with L-alanine, the methionine at position 27 is replaced with L-leucine, the asparagine at position 29 is replaced with L-leucine, or combinations thereof.

In particular aspects, the serine at position 16 is replaced with D-alanine or L-alanine, the arginine at position 18 is replaced with L-alanine, the methionine at position 27 is replaced with L-leucine, and the asparagine at position 29 is replaced with L-leucine.

The present invention further provides a composition comprising (i) a peptide having the amino acid sequence of native human glucagon as shown in SEQ ID NO:1 but in which the L-serine at position 2 is replaced with a D-serine; the tyrosine at position 10 is replaced with (i) L-lysine conjugated to a palmitoyl group by either a gamma-glutamic acid (γE) spacer or a gamma-glutamic acid-gamma-glutamic acid dipeptide (γEγE) spacer or (ii) para-aminomethyl phenylalanine conjugated to a palmitoyl group by either a gamma-glutamic acid (γE) spacer or a gamma-glutamic acid-gamma-glutamic acid dipeptide (γEγE) spacer; and up to six additional amino acid substitutions; wherein the peptide is an co-agonist of the glucagon receptor and the GLP-1 receptor and has a ratio of $EC_{50}$ at the glucagon receptor to $EC_{50}$ at the GLP-1 receptor of about 0.88 to about 1.25, about 0.90 to about 1.25, about 0.90 to about 1.10, about 0.90 to about 1.00, or about 1.0±0.12, and wherein the peptide optionally includes a protecting group that, if present, is joined to the C-terminal carboxy group of the peptide, and (ii) a pharmaceutically acceptable carrier; with the proviso that the peptide does not have the amino acid sequence of SEQ ID NO:21.

In particular aspects, the serine at position 16 is replaced with L-alanine, the arginine at position 18 is replaced with L-alanine, the methionine at position 27 is replaced with L-leucine, the asparagine at position 28 is replaced with L-aspartic acid, or combinations thereof.

The present invention further provides a pharmaceutical composition comprising (i) a peptide having the amino acid sequence of native human glucagon as shown in SEQ ID NO:1 but in which the L-serine at position 2 is replaced with a D-serine; the tyrosine at position 10 is replaced with (i) L-lysine conjugated to a palmitoyl group by either a gamma-glutamic acid (γE) spacer or a gamma-glutamic acid-gamma-glutamic acid dipeptide (γEγE) spacer or (ii) para-aminomethyl phenylalanine conjugated to a palmitoyl group by either a gamma-glutamic acid (γE) spacer or a gamma-glutamic acid-gamma-glutamic acid dipeptide (γEγE) spacer; and up to six additional amino acid substitutions; wherein the peptide is an co-agonist of the glucagon receptor and the GLP-1 receptor and has a ratio of $EC_{50}$ at the glucagon receptor to $EC_{50}$ at the GLP-1 receptor of about 0.88 to about 1.25, about 0.90 to about 1.25, about 0.90 to about 1.10, about 0.90 to about 1.00, or about 1.0±0.12, and wherein the peptide optionally includes a protecting group that, if present, is joined to the C-terminal carboxy group of the peptide, and (ii) a pharmaceutically acceptable carrier; with the proviso that the peptide does not have the amino acid sequence of SEQ ID NO:21.

In particular aspects, the serine at position 16 is replaced with L-alanine, the arginine at position 18 is replaced with L-alanine, the methionine at position 27 is replaced with L-leucine, the asparagine at position 28 is replaced with L-aspartic acid, or combinations thereof.

The present invention further provides a method for treating a patient for metabolic disease comprising administering the patient an effective amount of the peptide of any one of the aforementioned peptides to treat the metabolic disease in the patient.

The present invention further provides method for treating a patient for metabolic disease comprising administering the patient an effective amount of the composition of the aforementioned compositions to treat the metabolic disease in the patient.

In particular aspects, the metabolic disease is diabetes, non-alcoholic fatty liver disease (NAFLD), non-alcoholic steatohepatitis (NASH), or obesity.

In particular aspects, the diabetes is Type I diabetes, Type II diabetes, or gestational diabetes.

In particular aspects, the patient has more than one metabolic disease, for example, diabetes and NASH, NAFLD, or obesity; obesity and NASH or NAFLD; diabetes, NASH, and obesity; diabetes, NAFLD, and obesity; or diabetes and obesity.

The present invention further provides for the use of any one of the aforementioned peptides for manufacture of a medicament for the treatment of metabolic disease.

The present invention further provides for the use of any one of the aforementioned compositions for manufacture of a medicament for the treatment of metabolic disease.

In particular aspects, the metabolic disease is diabetes, non-alcoholic fatty liver disease (NAFLD), non-alcoholic steatohepatitis (NASH), or obesity.

In particular aspects, the diabetes is Type I diabetes, Type II diabetes, or gestational diabetes.

In particular aspects, the medicament is for treatment of more than one metabolic disease, for example, diabetes and NASH, NAFLD, or obesity; obesity and NASH or NAFLD; diabetes, NASH, and obesity; diabetes, NAFLD, and obesity; or diabetes and obesity.

In particular aspects of the compounds disclosed herein the C-terminal protecting group may be an amide or ester. For example, the carboxylic acid of the C-terminal amino acid is replaced with a charge-neutral group, such as an amide or ester.

Further provided is method for treating a metabolic disease in a patient or individual comprising: administering to the patient or individual an effective amount of any one of the aforementioned compositions comprising a co-agonist peptide and administering to the patient or individual an effective amount of a composition comprising an insulin or insulin analog to treat the metabolic disease in the patient or individual.

In particular aspects, the composition comprising the co-agonist peptide is administered at a time prior to the time the composition comprising the insulin or insulin analog is administered. In another aspect, the composition comprising the insulin or insulin analog is administered at a time prior to the time the composition comprising the co-agonist peptide is administered. In a further still aspect, the composition comprising the co-agonist peptide is administered at the same time as the composition comprising the insulin or insulin analog is administered.

In particular aspects, the insulin analog is insulin detemir, insulin glargine, insulin levemir, insulin glulisine, or insulin lispro.

In particular aspects, the metabolic disease is diabetes, non-alcoholic fatty liver disease (NAFLD), non-alcoholic steatohepatitis (NASH), or obesity.

In particular aspects, the diabetes is Type I diabetes, Type II diabetes, or gestational diabetes.

In particular aspects, the patient has more than one metabolic disease, for example, diabetes and NASH, NAFLD, or obesity; obesity and NASH or NAFLD; diabetes, NASH, and obesity; diabetes, NAFLD, and obesity; or diabetes and obesity.

The present invention further provides a composition comprising any one of the aforementioned peptides; an insulin or insulin analog; and, a pharmaceutically acceptable carrier.

The present invention further provides for the use of a composition comprising any one of the aforementioned peptides; an insulin or insulin analog; and, a pharmaceutically acceptable carrier for the treatment of a metabolic disease.

In particular aspects, the metabolic disease is diabetes, non-alcoholic fatty liver disease (NAFLD), non-alcoholic steatohepatitis (NASH), or obesity. In further aspects, the diabetes is Type I diabetes, Type II diabetes, or gestational diabetes.

The present invention further provides for the use of a composition comprising any one of the aforementioned peptides; an insulin or insulin analog; and, a pharmaceutically acceptable carrier for the manufacture of a medicament for the treatment of a metabolic disease.

In particular aspects, the metabolic disease is diabetes, non-alcoholic fatty liver disease (NAFLD), non-alcoholic steatohepatitis (NASH), or obesity. In further aspects, the diabetes is Type I diabetes, Type II diabetes, or gestational diabetes.

In a further embodiment, the GCG receptor/GLP-1 receptor co-agonist peptides of the present invention consist of the amino acid sequence of native human glucagon (SEQ ID NO:1) but in which the L-serine at position 2 is replaced with a D-serine, L-alanine, α-aminoisobutyric acid (Aib), or 1-amino-cyclobutane carboxylic acid; the tyrosine at position 10 is replaced with (i) L-lysine conjugated to a palmitoyl group by either a gamma-glutamic acid (γE) spacer or a gamma-glutamic acid-gamma-glutamic acid dipeptide (γEγE) spacer or (ii) para-aminomethyl phenylalanine conjugated to a palmitoyl group by either a gamma-glutamic acid (γE) spacer or a gamma-glutamic acid-gamma-glutamic acid dipeptide (γEγE) spacer; and may include up to six additional amino acid substitutions; wherein GCG receptor/GLP-1 receptor co-agonist peptides have a relatively balanced activity at the GCG receptor and GLP-1 receptor, and optionally a protecting group that, if present, is joined to the C-terminal carboxy group of the peptide with the proviso that the peptide does not have the amino acid sequence of SEQ ID NO:21.

In particular embodiments, the present invention provides a peptide consisting of the amino acid sequence $$HX_2QGTX_6TSDX_{10}SX_{12}YLX_{15}X_{16}RX_{18}AQDFVQWLX_{27}DT \quad \text{(SEQ ID NO: 20)}$$

Wherein $X_2$ is D-serine, L-alanine, α-aminoisobutyric acid (Aib), or 1-amino-cyclobutane carboxylic acid; $X_6$ is L-phenylalanine, para-fluoro phenylalanine or threo-β-phenylserine; $X_{10}$ is L-lysine or para-aminomethyl phenylalanine; $X_{12}$ is L-lysine or L-leucine; $X_{15}$ is L-glutamic acid or L-leucine; $X_{16}$ is L-alanine, Aib, L-glutamic acid, or L-valine; $X_{18}$ is L-alanine or L-arginine; $X_{27}$ is L-leucine, methionine sulfone, or L-norleucine; the amino acid at position 10 is conjugated to a palmitoyl group by either a gamma-glutamic acid (γE) spacer or a gamma-glutamic acid-gamma-glutamic acid dipeptide (γEγE) spacer; and, the peptide optionally includes a protecting group that, if present, is joined to the C-terminal carboxy group of the peptide; with the proviso that the peptide does not have the amino acid sequence of SEQ ID NO:21.

In particular embodiments, the peptide has the amino acid sequence of SEQ ID NO:7, 8, 9, 10, 12, 13, 14, 15, 16, 17, 18, or 19.

In particular embodiments, the peptide is an co-agonist of the glucagon receptor and the GLP-1 receptor and has a ratio of $EC_{50}$ at the glucagon receptor to $EC_{50}$ at the GLP-1 receptor of about 0.88 to about 1.25, about 0.90 to about 1.25, about 0.90 to about 1.10, about 0.90 to about 1.00, or about 1.0±0.12.

In particular embodiments, the peptide is an co-agonist of the glucagon receptor and the GLP-1 receptor and has a ratio of $EC_{50}$ at the glucagon receptor to $EC_{50}$ at the GLP-1 receptor of 0.88, 0.89, 0.90, 0.91, 0.92, 0.93, 0.94, 0.95, 0.96, 0.97, 0.98, 0.99, 1.00, 1.01, 1.02, 1.03, 1.04, 1.05, 1.06, 1.07, 1.08, 1.09, or 1.10.

The present invention further provides a composition consisting of a peptide having the amino acid sequence $$HX_2QGTX_6TSDX_{10}SX_{12}YLX_{15}X_{16}RX_{18}AQDFVQWLX_{27}DT \quad \text{(SEQ ID NO: 20)}$$

Wherein $X_2$ is D-serine, L-alanine, α-aminoisobutyric acid (Aib), or 1-amino-cyclobutane carboxylic acid; $X_6$ is L-phenylalanine, para-fluoro phenylalanine or threo-β-phenylserine; $X_{10}$ is L-lysine or para-aminomethyl phenylalanine; $X_{12}$ is L-lysine or L-leucine; $X_{15}$ is L-glutamic acid or L-leucine; $X_{16}$ is L-alanine, Aib, L-glutamic acid, or L-valine; $X_{18}$ is L-alanine or L-arginine; $X_{27}$ is L-leucine, methionine sulfone, or L-norleucine; the amino acid at position 10 is conjugated to a palmitoyl group by either a gamma-glutamic acid spacer (γE) or a gamma-glutamic acid-gamma-glutamic acid dipeptide (γEγE) spacer; the peptide optionally includes a protecting group that, if present, is joined to the C-terminal carboxy group of the peptide; and, a pharmaceutically acceptable carrier; with the proviso that the peptide does not have the amino acid sequence of SEQ ID NO:21.

In particular embodiments, the peptide has the amino acid sequence of SEQ ID NO:7, 8, 9, 10, 12, 13, 14, 15, 16, 17, 18, or 19.

In particular embodiments, the peptide is an co-agonist of the glucagon receptor and the GLP-1 receptor and has a ratio of $EC_{50}$ at the glucagon receptor to $EC_{50}$ at the GLP-1 receptor of about 0.88 to about 1.25, about 0.90 to about 1.25, about 0.90 to about 1.10, about 0.90 to about 1.00, or about 1.0±0.12.

In particular embodiments, the peptide is an co-agonist of the glucagon receptor and the GLP-1 receptor and has a ratio of $EC_{50}$ at the glucagon receptor to $EC_{50}$ at the GLP-1 receptor of 0.88, 0.89, 0.90, 0.91, 0.92, 0.93, 0.94, 0.95, 0.96, 0.97, 0.98, 0.99, 1.00, 1.01, 1.02, 1.03, 1.04, 1.05, 1.06, 1.07, 1.08, 1.09, or 1.10.

The present invention further provides a pharmaceutical composition consisting of a peptide having the amino acid sequence $$HX_2QGTX_6TSDX_{10}SX_{12}YLX_{15}X_{16}RX_{18}AQDFVQWLX_{27}DT \quad \text{(SEQ ID NO: 20)}$$

Wherein $X_2$ is D-serine, L-alanine, α-aminoisobutyric acid (Aib), or 1-amino-cyclobutane carboxylic acid; $X_6$ is L-phenylalanine, para-fluoro phenylalanine or threo-β-phenylserine; $X_{10}$ is L-lysine or para-aminomethyl phenylalanine; $X_{12}$ is L-lysine or L-leucine; $X_{15}$ is L-glutamic acid or L-leucine; $X_{16}$ is L-alanine, Aib, L-glutamic acid, or L-valine; $X_{18}$ is L-alanine or L-arginine; $X_{27}$ is L-leucine, methionine sulfone, or L-norleucine; the amino acid at position 10 is conjugated to a palmitoyl group by either a gamma-glutamic acid (γE) spacer or a gamma-glutamic acid-gamma-glutamic acid dipeptide (γEγE) spacer; the peptide optionally includes a protecting group that, if present, is joined to the C-terminal carboxy group of the peptide; and, a pharmaceutically acceptable carrier; with the proviso that the peptide does not have the amino acid sequence of SEQ ID NO:21.

In particular embodiments, the peptide has the amino acid sequence of SEQ ID NO:7, 8, 9, 10, 12, 13, 14, 15, 16, 17, 18, or 19.

In particular embodiments, the peptide is an co-agonist of the glucagon receptor and the GLP-1 receptor and has a ratio of $EC_{50}$ at the glucagon receptor to $EC_{50}$ at the GLP-1 receptor of about 0.88 to about 1.25, about 0.90 to about 1.25, about 0.90 to about 1.10, about 0.90 to about 1.00, or about 1.0±0.12.

In particular embodiments, the peptide is an co-agonist of the glucagon receptor and the GLP-1 receptor and has a ratio of $EC_{50}$ at the glucagon receptor to $EC_{50}$ at the GLP-1 receptor of 0.88, 0.89, 0.90, 0.91, 0.92, 0.93, 0.94, 0.95, 0.96, 0.97, 0.98, 0.99, 1.00, 1.01, 1.02, 1.03, 1.04, 1.05, 1.06, 1.07, 1.08, 1.09, or 1.10.

The present invention further provides a peptide consisting of the amino acid sequence of native human glucagon having the amino acid sequence shown in SEQ ID NO:1 but in which the L-serine at position 2 is replaced with a D-serine; the tyrosine at position 10 is replaced with (i)

L-lysine conjugated to a palmitoyl group by either a gamma-glutamic acid (γE) spacer or a gamma-glutamic acid-gamma-glutamic acid dipeptide (γEγE) spacer or (ii) para-aminomethyl phenylalanine conjugated to a palmitoyl group by either a gamma-glutamic acid (γE) spacer or a gamma-glutamic acid-gamma-glutamic acid dipeptide (γEγE) spacer; and up to six additional amino acid substitutions; wherein the peptide is an co-agonist of the glucagon receptor and the GLP-1 receptor and has a ratio of $EC_{50}$ at the glucagon receptor to $EC_{50}$ at the GLP-1 receptor of about 0.88 to about 1.25, about 0.90 to about 1.25, about 0.90 to about 1.10, about 0.90 to about 1.00, or about 1.0±0.12, and wherein the peptide optionally includes a protecting group that, if present, is joined to the C-terminal carboxy group of the peptide; with the proviso that the peptide does not have the amino acid sequence of SEQ ID NO:21.

In particular aspects, the serine at position 16 is replaced with D-alanine or L-alanine, the arginine at position 18 is replaced with L-alanine, the methionine at position 27 is replaced with L-leucine, the asparagine at position 29 is replaced with L-leucine, or combinations thereof.

In particular aspects, the serine at position 16 is replaced with D-alanine or L-alanine, the arginine at position 18 is replaced with L-alanine, the methionine at position 27 is replaced with L-leucine, and the asparagine at position 29 is replaced with L-leucine.

The present invention further provides a composition consisting of (i) a peptide consisting of the amino acid sequence of native human glucagon as shown in SEQ ID NO:1 but in which the L-serine at position 2 is replaced with a D-serine; the tyrosine at position 10 is replaced with (i) L-lysine conjugated to a palmitoyl group by either a gamma-glutamic acid (γE) spacer or a gamma-glutamic acid-gamma-glutamic acid dipeptide (γEγE) spacer or (ii) para-aminomethyl phenylalanine conjugated to a palmitoyl group by either a gamma-glutamic acid (γE) spacer or a gamma-glutamic acid-gamma-glutamic acid dipeptide (γEγE) spacer; and up to six additional amino acid substitutions; wherein the peptide is an co-agonist of the glucagon receptor and the GLP-1 receptor and has a ratio of $EC_{50}$ at the glucagon receptor to $EC_{50}$ at the GLP-1 receptor of about 0.88 to about 1.25, about 0.90 to about 1.25, about 0.90 to about 1.10, about 0.90 to about 1.00, or about 1.0±0.12, and wherein the peptide optionally includes a protecting group that, if present, is joined to the C-terminal carboxy group of the peptide, and (ii) a pharmaceutically acceptable carrier; with the proviso that the peptide does not have the amino acid sequence of SEQ ID NO:21.

In particular aspects, the serine at position 16 is replaced with L-alanine, the arginine at position 18 is replaced with L-alanine, the methionine at position 27 is replaced with L-leucine, the asparagine at position 28 is replaced with L-aspartic acid, or combinations thereof.

The present invention further provides a pharmaceutical composition consisting of (i) a peptide consisting of the amino acid sequence of native human glucagon as shown in SEQ ID NO:1 but in which the L-serine at position 2 is replaced with a D-serine; the tyrosine at position 10 is replaced with (i) L-lysine conjugated to a palmitoyl group by either a gamma-glutamic acid (γE) spacer or a gamma-glutamic acid-gamma-glutamic acid dipeptide (γEγE) spacer or (ii) para-aminomethyl phenylalanine conjugated to a palmitoyl group by either a gamma-glutamic acid (γE) spacer or a gamma-glutamic acid-gamma-glutamic acid dipeptide (γEγE) spacer; and up to six additional amino acid substitutions; wherein the peptide is an co-agonist of the glucagon receptor and the GLP-1 receptor and has a ratio of $EC_{50}$ at the glucagon receptor to $EC_{50}$ at the GLP-1 receptor of about 0.88 to about 1.25, about 0.90 to about 1.25, about 0.90 to about 1.10, about 0.90 to about 1.00, or about 1.0±0.12, and wherein the peptide optionally includes a protecting group that, if present, is joined to the C-terminal carboxy group of the peptide, and (ii) a pharmaceutically acceptable carrier; with the proviso that the peptide does not have the amino acid sequence of SEQ ID NO:21.

In particular aspects, the serine at position 16 is replaced with L-alanine, the arginine at position 18 is replaced with L-alanine, the methionine at position 27 is replaced with L-leucine, the asparagine at position 28 is replaced with L-aspartic acid, or combinations thereof.

The present invention further provides a method for treating a patient for obesity metabolic disease consisting of administering the patient an effective amount of the peptide of any one of the aforementioned peptides to treat the metabolic disease in the patient.

The present invention further provides method for treating a patient for obesity metabolic disease consisting of administering the patient an effective amount of the composition of the aforementioned compositions to treat the metabolic disease in the patient.

In particular aspects, the metabolic disease is diabetes, non-alcoholic fatty liver disease (NAFLD), non-alcoholic steatohepatitis (NASH), or obesity.

In particular aspects, the diabetes is Type I diabetes, Type II diabetes, or gestational diabetes.

In particular aspects, the patient has more than one metabolic disease, for example, diabetes and NASH, NAFLD, or obesity; obesity and NASH or NAFLD; diabetes, NASH, and obesity; diabetes, NAFLD, and obesity; or diabetes and obesity.

The present invention further provides for the use of any one of the aforementioned peptides for manufacture of a medicament for the treatment of obesity metabolic disease.

The present invention further provides for the use of any one of the aforementioned compositions for manufacture of a medicament for the treatment of obesity metabolic disease.

In particular aspects, the metabolic disease is diabetes, non-alcoholic fatty liver disease (NAFLD), non-alcoholic steatohepatitis (NASH), or obesity.

In particular aspects, the diabetes is Type I diabetes, Type II diabetes, or gestational diabetes.

In particular aspects, the medicament is for treatment of more than one metabolic disease, for example, diabetes and NASH, NAFLD, or obesity; obesity and NASH or NAFLD; diabetes, NASH, and obesity; diabetes, NAFLD, and obesity; or diabetes and obesity.

In particular aspects of the compounds disclosed herein the C-terminal protecting group may be an amide or ester. For example, the carboxylic acid of the C-terminal amino acid is replaced with a charge-neutral group, such as an amide or ester.

Further provided is method for treating a metabolic disease in a patient or individual consisting of: administering to the patient or individual an effective amount of any one of the aforementioned compositions consisting of a co-agonist peptide and administering to the patient or individual an effective amount of a composition consisting of an insulin or insulin analog to treat the metabolic disease in the patient or individual.

In particular aspects, the composition consisting of the co-agonist peptide is administered at a time prior to the time the composition consisting of the insulin or insulin analog is administered. In another aspect, the composition consisting of the insulin or insulin analog is administered at a time prior to the time the composition consisting of the co-agonist peptide is administered. In a further still aspect, the composition consisting of the co-agonist peptide is administered at the same time as the composition consisting of the insulin or insulin analog is administered.

In particular aspects, the insulin analog is insulin detemir, insulin glargine, insulin levemir, insulin glulisine, or insulin lispro.

In particular aspects, the metabolic disease is diabetes, non-alcoholic fatty liver disease (NAFLD), non-alcoholic steatohepatitis (NASH), or obesity.

In particular aspects, the diabetes is Type I diabetes, Type II diabetes, or gestational diabetes.

In particular aspects, the patient has more than one metabolic disease, for example, diabetes and NASH, NAFLD, or obesity; obesity and NASH or NAFLD; diabetes, NASH, and obesity; diabetes, NAFLD, and obesity; or diabetes and obesity.

The present invention further provides a composition consisting of any one of the aforementioned peptides; an insulin or insulin analog; and, a pharmaceutically acceptable carrier.

The present invention further provides for the use of a composition consisting of any one of the aforementioned peptides; an insulin or insulin analog; and, a pharmaceutically acceptable carrier for the treatment of a metabolic disease.

In particular aspects, the metabolic disease is diabetes, non-alcoholic fatty liver disease (NAFLD), non-alcoholic steatohepatitis (NASH), or obesity. In further aspects, the diabetes is Type I diabetes, Type II diabetes, or gestational diabetes.

The present invention further provides for the use of a composition consisting of any one of the aforementioned peptides; an insulin or insulin analog; and, a pharmaceutically acceptable carrier for the manufacture of a medicament for the treatment of a metabolic disease.

In particular aspects, the metabolic disease is diabetes, non-alcoholic fatty liver disease (NAFLD), non-alcoholic steatohepatitis (NASH), or obesity. In further aspects, the diabetes is Type I diabetes, Type II diabetes, or gestational diabetes.

Definitions

The term "about" as used herein means greater or lesser than the value or range of values stated by 10 percent, but is not intended to designate any value or range of values to only this broader definition. Each value or range of values preceded by the term "about" is also intended to encompass the embodiment of the stated absolute value or range of values.

The term "individual" is meant to include humans and companion or domesticated animals such as dogs, cats, horses, and the like. Therefore, the compositions comprising a compound or one or more co-agonist peptides as disclosed herein are also useful for treating or preventing obesity and obesity-related disorders in cats and dogs. As such, the term "mammal" includes humans and companion animals such as cats and dogs.

As used herein, the term "pharmaceutically acceptable carrier" includes any carrier suitable for administering to an individual, for example any of the standard pharmaceutical carriers, including but not limited to a phosphate buffered saline solution, water, emulsions such as an oil/water or water/oil emulsion, and various types of wetting agents. The term also encompasses any of the agents approved by a regulatory agency of the U.S. Federal government or listed in the U.S. Pharmacopeia for use in animals, including humans. In general, "pharmaceutically acceptable carrier" means a non-toxic material that does not interfere with the effectiveness of the biological activity of the active ingredient(s), approved by a regulatory agency of the Federal or a state government or listed in the U.S. Pharmacopoeia or other generally recognized pharmacopoeia for use in animals and, more particularly, in humans. The term "carrier" refers to a diluent, adjuvant, excipient, or vehicle with which the therapeutic is administered and includes, but is not limited to such sterile liquids as water and oils. The characteristics of the carrier will depend on the route of administration.

As used herein the term "pharmaceutically acceptable salt" refers to salts of compounds that retain the biological activity of the parent compound, and which are not biologically or otherwise undesirable. Many of the compounds disclosed herein are capable of forming acid and/or base salts by virtue of the presence of amino and/or carboxyl groups or groups similar thereto. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines.

Pharmaceutically acceptable salts may be prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. The term "pharmaceutically acceptable salt" further includes all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations. It will be understood that, as used herein, references to the co-agonist peptides disclosed herein are meant to also include embodiments that comprise a co-agonist peptide or peptides and one or more of the pharmaceutically acceptable salts.

As used herein, the term "treating" includes prophylaxis of the specific disorder or condition, or alleviation of the symptoms associated with a specific disorder or condition and/or preventing or eliminating said symptoms. For example, as used herein the term "treating diabetes" will refer in general to altering glucose blood levels in the direction of normal levels and may include increasing or decreasing blood glucose levels depending on a given situation.

As used herein an "effective" amount or a "therapeutically effective amount" means the total amount of each active component of the pharmaceutical composition or method that is sufficient to show a meaningful patient benefit, i.e., treatment, healing, prevention or amelioration of the relevant medical condition, or an increase in rate of treatment, healing, prevention or amelioration of such conditions. It refers to the amount of a co-agonist peptide or peptides that is nontoxic but sufficient to provide the desired effect. For example one desired effect would be the prevention or treatment of hyperglycemia, e.g., as measured by a change in blood glucose level closer to normal, or treatment of obesity by inducing weight loss and/or preventing weight gain, e.g., as measured by reduction in body weight, or preventing or reducing an increase in body weight, or normalizing body fat distribution. The amount that is "effective" will vary from subject to subject, depending on the age and general condition of the individual, mode of administration, and the like. Thus, it is not always possible to specify an exact "effective amount." However, an appropriate "effective" amount in any individual case may be determined by one of ordinary skill in the art using routine experimentation. When applied to an individual active ingredient, administered alone, the term refers to that ingredient alone. When applied to a combination, the term refers to combined amounts of the active ingredients that result in the therapeutic effect, whether administered in combination, serially, or simultaneously.

The term, "parenteral" means not through the alimentary canal but by some other route, e.g., subcutaneous, intramuscular, intraspinal, or intravenous.

As used herein, the term "peptide" encompasses a chain of 3 or more amino acids and typically less than 100 amino acids, wherein the amino acids are naturally occurring or coded or non-naturally occurring or non-coded amino acids. Non-naturally occurring amino acids refer to amino acids that do not naturally occur in vivo but which, nevertheless, can be incorporated into the peptide structures described herein. "Non-coded" as used herein refers to an amino acid that is not an L-isomer of any of the following 20 amino acids: Ala, Cys, Asp, Glu, Phe, Gly, His, He, Lys, Leu, Met, Asn, Pro, Gln, Arg, Ser, Thr, Val, Trp, Tyr. "Coded" as used herein refers to an amino acid that is an L-isomer of any of the following 20 amino acids: Ala, Cys, Asp, Glu, Phe, Gly, His, He, Lys, Leu, Met, Asn, Pro, Gln, Arg, Ser, Thr, Val, Trp, Tyr. In some embodiments, the peptides and variant peptides described herein are about the same length as SEQ ID NO: 1 (which is 29 amino acids in length), e.g. 25-35 amino acids in length. Exemplary lengths include 29, 30, 31, 32, 33, 34, 35, 36, 37, 38, 39, 40, 41, 42, 43, 44, 45, 46, 47, 48, 49, or 50 amino acids in length.

Typically, polypeptides and proteins have a polymer length that is greater than that of "peptides."

Similarly, a reference herein to "position 28" would mean the corresponding position 29 for a glucagon analog in which one amino acid has been added before the N-terminus of SEQ ID NO: 1. As used herein an "amino acid modification" refers to (i) a substitution or replacement of an amino acid of SEQ ID NO: 1 with a different amino acid (naturally-occurring or coded or non-coded or non-naturally-occurring amino acid), (ii) an addition of an amino acid (naturally-occurring or coded or non-coded or non-naturally-occurring amino acid), to SEQ ID NO: 1 or (iii) a deletion of one or more amino acids of SEQ ID NO: 1.

Amino acid "modification" refers to an insertion, deletion or substitution of one amino acid with another. In some embodiments, the amino acid substitution or replacement is a conservative amino acid substitution, e.g., a conservative substitution of the amino acid at one or more of positions 2, 5, 7, 10, 11, 12, 13, 14, 16, 17, 18, 19, 20, 21, 24, 27, 28 or 29. As used herein, the term "conservative amino acid substitution" is the replacement of one amino acid with another amino acid having similar properties, e.g., size, charge, hydrophobicity, hydrophilicity, and/or aromaticity, and includes exchanges within one of the following five groups:

I. Small aliphatic, nonpolar or slightly polar residues: Ala, Ser, Thr, Pro, Gly;
II. Polar, negative-charged residues and their amides and esters:
Asp, Asn, Glu, Gln, cysteic acid and homocysteic acid;
III. Polar, positive-charged residues:
His, Arg, Lys; Ornithine (Orn)
IV. Large, aliphatic, nonpolar residues:
Met, Leu, He, Val, Cys, Norleucine (Nle), homocysteine
V. Large, aromatic residues:
Phe, Tyr, Trp, acetyl phenylalanine In some embodiments, the amino acid substitution is not a conservative amino acid substitution, e.g., is a non-conservative amino acid substitution.

As used herein the term "charged amino acid" or "charged residue" refers to an amino acid that comprises a side chain that is negative-charged (i.e., de-protonated) or positive-charged (i.e., protonated) in aqueous solution at physiological pH. For example negative-charged amino acids include aspartic acid, glutamic acid, cysteic acid, homocysteic acid, and homoglutamic acid, whereas positive-charged amino acids include arginine, lysine and histidine. Charged amino acids include the charged amino acids among the 20 coded amino acids, as well as atypical or non-naturally occurring or non-coded amino acids.

As used herein the term "acidic amino acid" refers to an amino acid that comprises a second acidic moiety (other than the carboxylic acid of the amino acid), including for example, a carboxylic acid or sulfonic acid group.

As used herein, the term "acylated amino acid" refers to an amino acid comprising an acyl group which is non-native to a naturally-occurring amino acid, regardless of the means by which it is produced (e.g. acylation prior to incorporating the amino acid into a peptide, or acylation after incorporation into a peptide).

As used herein the term "alkylated amino acid" refers to an amino acid comprising an alkyl group which is non-native to a naturally-occurring amino acid, regardless of the means by which it is produced. Accordingly, the acylated amino acids and alkylated amino acids of the present disclosures are non-coded amino acids.

As used herein, the term "selectivity" of a molecule for a first receptor relative to a second receptor refers to the following ratio: $EC_{50}$ of the molecule at the second receptor divided by the $EC_{50}$ of the molecule at the first receptor. For example, a molecule that has an EC50 of 1 nM at a first receptor and an $EC_{50}$ of 100 nM at a second receptor has 100-fold selectivity for the first receptor relative to the second receptor.

As used herein the term "native glucagon" refers to a peptide consisting of the sequence of SEQ ID NO: 1 and the term "native GLP-1" is a generic term that designates GLP-1(7-36) amide, GLP-1 (7-37) acid or a mixture of those two compounds.

As used herein, "glucagon potency" or "potency compared to native glucagon" of a molecule refers to the inverse ratio of the $EC_{50}$ of the molecule at the glucagon receptor divided by the $EC_{50}$ of native glucagon at glucagon receptor.

As used herein, "GLP-1 potency" or "potency compared to native GLP-1" of a molecule refers to the inverse ratio of the $EC_{50}$ of the molecule at GLP-1 receptor divided by the $EC_{50}$ of native GLP-1 at GLP-1 receptor.

DETAILED DESCRIPTION OF THE INVENTION

Figure 1:
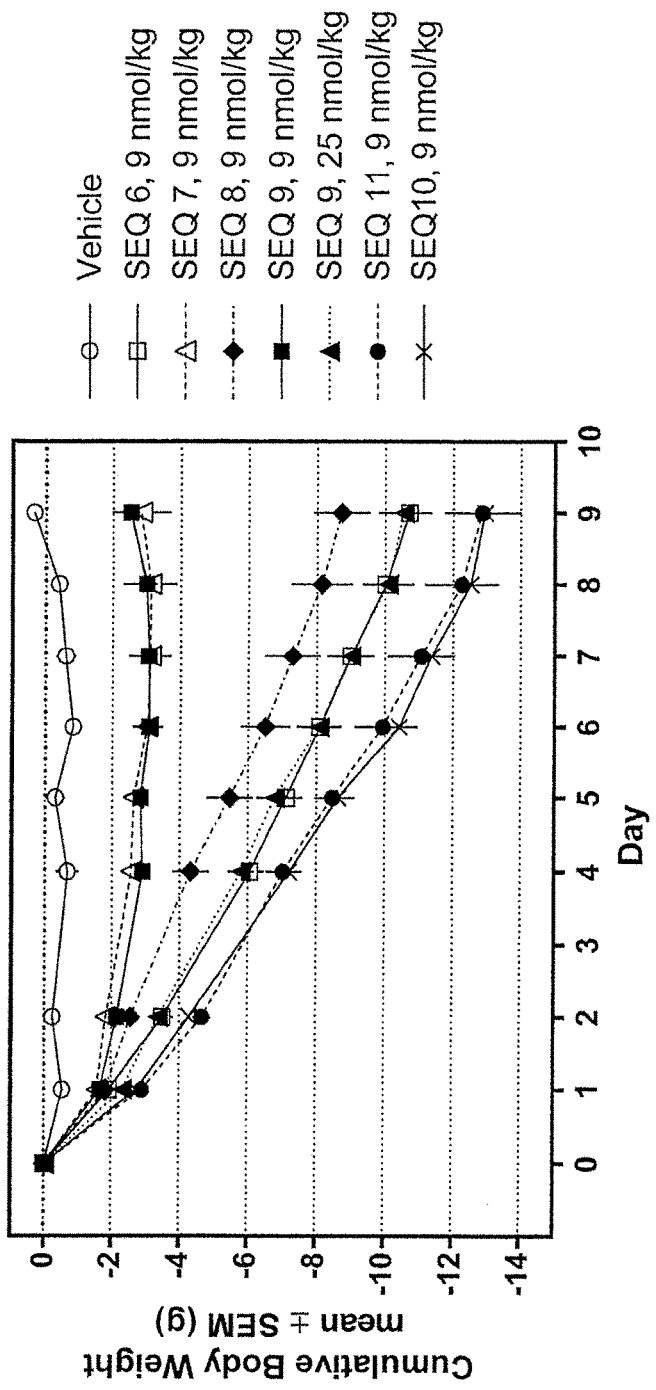
FIG. 1 represents a graph of the cumulative weight change (grams) of diet-induced obese (DIO) mice treated with a vehicle control or a daily dose of a peptide of SEQ ID NO: 6 to 11, as detailed in Example 18.

The present disclosures provide peptides and variant peptides that exhibit activity at both the GLP-1 receptor (GLP-1) and at the glucagon (GCG) receptor. In this regard, the present disclosures provide GLP-1 receptor/GCG receptor co-agonist peptides. In exemplary embodiments, the presently disclosed peptides and variant peptides exhibit relatively balanced activity or potency at the GCG receptor and the GLP-1 receptors, as compared to native human glucagon (SEQ ID NO: 1).

In exemplary embodiments, the peptides and variant peptides described herein exhibit other improvements in properties relative to native glucagon or native GLP-1, such as greater stability, greater solubility, a prolonged half-life in circulation, a delayed onset of action, an extended duration of action, a dampened peak (e.g., relatively decreased mean peak plasma concentration), and an improved resistance to proteases, such as DPP-IV.

Conjugates, fusion proteins and multimers of any of the peptide sequences disclosed herein are also contemplated.

Glucagon is a peptide hormone structurally related to GLP-1 that is well recognized for its acute ability to increase blood glucose through stimulation of glycogenolysis and gluconeogenesis. While administration of glucagon was first reported over 60 years ago to yield improvements in rodent metabolism, including lowering body weight (Salter, Am. J. Clin. Nutr. 8: 535-539 (1960)) these results have not been translated into the use of glucagon in therapies for a treatment of obesity in humans, particularly due to the inherent risk of hyperglycemia, especially in insulin-resistant type-2 diabetic patients.

The use of balanced GCG receptor/GLP-1 receptor co-agonists as being of enhanced efficacy and safety relative to pure GLP-1 receptor agonists in the treatment of rodent obesity, with simultaneous improvement in glycemic control (Day et al., Nat. Chem. Biol. 5: 749-757 (2009); Pocai et al., Diabetes 58: 2258-2266 (2009)). Oxyntomodulin (OXM) is an endogenous precursor to glucagon, which is secreted postprandially by L-cells of the jejuno-ileum together with GLP-1 and has been shown to be a balanced co-agonist at the GLP-1 receptor and glucagon receptor albeit of relatively low potency (Holst, Regul. Pept. 93: 45-51 (2000); Drucker, J. Nat. Clin. Pract. Endocrinol. Metab. 1: 22-31 (2005); Baldissera et al., Regul. Pept. 21: 151-166 (1988); Gros et al., Endocrinol. 133: 631-638 (1993); Pocai et al., op. cit.). A 4-week clinical study in obese subjects demonstrated that repeated subcutaneous administration of OXM was well tolerated and caused significant weight loss, with a concomitant reduction in food intake (Wynne et al., Diabetes 54: 2390-2395 (2005)).

While Day et al., Peptide Sci. 98: 443-450 (2012) reported the importance of GLP-1 receptor balance in preventing GCG receptor-mediated hyperglycemia in obese mice using a family of co-agonist peptides that vary in murine receptor potency for the two receptors, they do not disclose co-agonist peptides that have the balanced potency or activity of the co-agonists peptides disclosed herein.

In contrast, the GCG receptor/GLP-1 receptor co-agonist peptides of the invention have relatively balanced activity or potency at the GCG receptor and GLP-1 receptor. The present invention provides peptides comprising the amino acid sequence of native human glucagon having the amino acid sequence shown in SEQ ID NO:1 but in which the L-serine at position 2 is replaced with a D-serine; the tyrosine at position 10 is replaced with (i) L-lysine conjugated to a palmitoyl group by either a gamma-glutamic acid (γE) spacer or a gamma-glutamic acid-gamma-glutamic acid dipeptide (γEγE) spacer or (ii) para-aminomethyl phenylalanine conjugated to a palmitoyl group by either a gamma-glutamic acid (γE) spacer or a gamma-glutamic acid-gamma-glutamic acid dipeptide (γEγE) spacer; and up to six additional amino acid substitutions; wherein the peptide is an co-agonist of the glucagon receptor and the GLP-1 receptor and has a ratio of $EC_{50}$ at the glucagon receptor to $EC_{50}$ at the GLP-1 receptor of about 0.88 to about 1.25, about 0.90 to about 1.25, about 0.90 to about 1.10, about 0.90 to about 1.00, or about 1.0±0.12, and wherein the peptide optionally includes a protecting group that, if present, is joined to the C-terminal carboxy group of the peptide; with the proviso that the peptide does not have the amino acid sequence of SEQ ID NO:21. In particular aspects, the peptides have a ratio of $EC_{50}$ at the glucagon receptor to $EC_{50}$ at the GLP-1 receptor of 0.88, 0.89, 0.90, 0.91, 0.92, 0.93, 0.94, 0.95, 0.96, 0.97, 0.98, 0.99, 1.00, 1.01, 1.02, 1.03, 1.04, 1.05, 1.06, 1.07, 1.08, 1.09, or 1.10.

The present invention further provides peptides comprising the amino acid sequence (SEQ ID NO: 20)
$HX_2QGTX_6TSDX_{10}SX_{12}YLX_{15}X_{16}RX_{18}AQDFVQWLX_{27}DT$ Wherein $X_2$ is D-serine, L-alanine, α-aminoisobutyric acid (Aib), or 1-amino-cyclobutane carboxylic acid; $X_6$ is L-phenylalanine, para-fluoro phenylalanine or threo-β-phenylserine; $X_{10}$ is L-lysine or para-aminomethyl phenylalanine; $X_{12}$ is L-lysine or L-leucine; $X_{15}$ is L-glutamic acid or L-leucine; $X_{16}$ is L-alanine, Aib, L-glutamic acid, or L-valine; $X_{18}$ is L-alanine or L-arginine; $X_{27}$ is L-leucine, methionine sulfone, or L-norleucine; the amino acid at position 10 is conjugated to a palmitoyl group by either a gamma-glutamic acid (γE) spacer or a gamma-glutamic acid-gamma-glutamic acid dipeptide (γEγE) spacer; and, the peptide optionally includes a protecting group that, if present, is joined to the C-terminal carboxy group of the peptide; with the proviso that the peptides do not include a peptide having the amino acid sequence of SEQ ID NO:21. The peptides are co-agonists of the glucagon receptor and the GLP-1 receptor and have a ratio of $EC_{50}$ at the glucagon receptor to $EC_{50}$ at the GLP-1 receptor of about 0.88 to about 1.25, about 0.90 to about 1.25, about 0.90 to about 1.10, about 0.90 to about 1.00, or about 1.0±0.12. The peptides are co-agonist of the glucagon receptor and the GLP-1 receptor and have a ratio of $EC_{50}$ at the glucagon receptor to $EC_{50}$ at the GLP-1 receptor of 0.88, 0.89, 0.90, 0.91, 0.92, 0.93, 0.94, 0.95, 0.96, 0.97, 0.98, 0.99, 1.00, 1.01, 1.02, 1.03, 1.04, 1.05, 1.06, 1.07, 1.08, 1.09, or 1.10.

The present invention further provides peptides comprising or consisting of the amino acid sequence (SEQ ID NO: 20)
HX$_2$QGTX$_6$TSDX$_{10}$SX$_{12}$YLX$_{15}$X$_{16}$RX$_{18}$AQDFVQWLX$_{27}$DT Wherein $X_2$ is D-serine, L-alanine, α-aminoisobutyric acid (Aib), or 1-amino-cyclobutane carboxylic acid; $X_6$ is L-phenylalanine, para-fluoro phenylalanine or threo-β-phenylserine; $X_{10}$ is L-lysine or para-aminomethyl phenylalanine; $X_{12}$ is L-lysine or L-leucine; $X_{15}$ is L-glutamic acid or L-leucine; $X_{16}$ is L-alanine, Aib, L-glutamic acid, or L-valine; $X_{18}$ is L-alanine or L-arginine; $X_{27}$ is L-leucine, methionine sulfone, or L-norleucine; the amino acid at position 10 is conjugated to a palmitoyl group by either a gamma-glutamic acid (γE) spacer or a gamma-glutamic acid-gamma-glutamic acid dipeptide (γEγE) spacer; and, the peptide optionally includes a protecting group that, if present, is joined to the C-terminal carboxy group of the peptide; with the proviso that the peptides do not include a peptide having the amino acid sequence of SEQ ID NO:21. The peptides are co-agonists of the glucagon receptor and the GLP-1 receptor and have a ratio of $EC_{50}$ at the glucagon receptor to $EC_{50}$ at the GLP-1 receptor of about 0.88 to about 1.25, about 0.90 to about 1.25, about 0.90 to about 1.10, about 0.90 to about 1.00, or about 1.0±0.12. The peptides are co-agonist of the glucagon receptor and the GLP-1 receptor and have a ratio of $EC_{50}$ at the glucagon receptor to $EC_{50}$ at the GLP-1 receptor of 0.88, 0.89, 0.90, 0.91, 0.92, 0.93, 0.94, 0.95, 0.96, 0.97, 0.98, 0.99, 1.00, 1.01, 1.02, 1.03, 1.04, 1.05, 1.06, 1.07, 1.08, 1.09, or 1.10.

Examples of peptides of the present invention are shown in Table 1.

TABLE 1

| SEQ ID NO: | Peptide |
|---|---|
| 6 | HsQGTFTSDK(γEC$_{16}$)SKYLDARAAQDFVQWLLDT-NH$_2$ |
| 7 | HsQGTFTSDK(γEγEC$_{16}$)SKYLDVRRAQDFVQWLLDT-NH$_2$ |
| 8 | HsQGTFTSDK(γEγEC$_{16}$)SKYLDVRAAQDFVQWLLDT-NH$_2$ |
| 9 | HUVGTFTSDK(γEγEC$_{16}$)SKYLDURAAQDFVQWLλDT-NH$_2$ |

TABLE 1-continued

| SEQ ID NO: | Peptide |
|---|---|
| 10 | HsQGTFTSDK(γEγEC$_{16}$)SKYLDARAAQDFVQWLLDT-NH$_2$ |
| 12 | AcHAQGTFTSDK(γEγEC$_{16}$)SKYLDERAAQDFVQWLLDT-NH$_2$ |
| 13 | HsQGTFTSDK(γEγEC$_{16}$)SKYLEARAAQDFVQWLLDT-NH$_2$ |
| 14 | HsQGTpFFTSDK(γEγEC$_{16}$)SKYLDERAAQDFVQWLLDT-NH$_2$ |
| 15 | HsQGTFTSDK(γEγEC16)SKYLDERAAQDFVQWL2DT-NH$_2$ |
| 16 | HsQGTFTSDK(γEγEC16)SLYLDERAAQDFVQWLLDT-NH$_2$ |
| 17 | HsQGTFTSDpAF(γEγEC16)SKYLDARAAQDFVQWLLDT-NH$_2$ |
| 18 | H‡QGTFTSDK(γEγEC16)SKYLDERAAQDFVQWLLDT-NH$_2$ |
| 19 | HsQGTtβPTSDK(γEγEC16)SKYLDERAAQDFVQWLLDT-NH$_2$ | s = D-serine;
U = α-aminoisobutyric acid (Aib);
λ = norleucine (Nle);
pA = para-aminomethyl phenylalanine;
2 = methionine sulfone;
‡ = 1-amino-1-cyclobutane carboxylic acid;
tβP = threo-β-Phenylserine;
Ac = acetyl;
pFF = p-fluorophenylalanine As shown in the examples, the GCG receptor/GLP-1 receptor co-agonist peptides of the present invention have an $EC_{50}$ of about 0.02 to about 1.04 nM at the GCG receptor and an $EC_{50}$ of about 0.03 to about 1.3 nM at the GLP-1 receptor. In particular aspects, the GCG receptor/GLP-1 receptor co-agonist peptides have a ratio of $EC_{50}$ at the glucagon receptor to $EC_{50}$ at the GLP-1 receptor of about 0.88 to about 1.25, about 0.90 to about 1.25, about 0.90 to about 1.10, about 0.90 to about 1.00, or about 1.0±0.12. Thus, the present invention provides peptides with relative balanced agonist activities or potencies against GLP-1 receptor and GCG receptor and which display the optimal therapeutic profile for weight loss while mitigating the hyperglycemic risk associated with GCG receptor activation.

The present invention provides compositions comprising or consisting of one or more peptides comprising the amino acid sequence of native human glucagon having the amino acid sequence shown in SEQ ID NO:1 but in which the L-serine at position 2 is replaced with a D-serine; the tyrosine at position 10 is replaced with (i) L-lysine conjugated to a palmitoyl group by either a gamma-glutamic acid (γE) spacer or a gamma-glutamic acid-gamma-glutamic acid dipeptide (γEγE) spacer or (ii) para-aminomethyl phenylalanine conjugated to a palmitoyl group by either a gamma-glutamic acid (γE) spacer or a gamma-glutamic acid-gamma-glutamic acid dipeptide (γEγE) spacer; and up to six additional amino acid substitutions; wherein the peptide is an co-agonist of the glucagon receptor and the GLP-1 receptor and has a ratio of $EC_{50}$ at the glucagon receptor to $EC_{50}$ at the GLP-1 receptor of about 0.88 to about 1.25, about 0.90 to about 1.25, about 0.90 to about 1.10, about 0.90 to about 1.00, or about 1.0±0.12, and wherein the peptide optionally includes a protecting group that, if present, is joined to the C-terminal carboxy group of the peptide, and a pharmaceutically acceptable carrier; with the proviso that the peptide does not have the amino acid sequence of SEQ ID NO:21. In particular aspects, the peptides have a ratio of $EC_{50}$ at the glucagon receptor to $EC_{50}$ at the GLP-1 receptor of 0.88, 0.89, 0.90, 0.91, 0.92, 0.93, 0.94, 0.95, 0.96, 0.97, 0.98, 0.99, 1.00, 1.01, 1.02, 1.03, 1.04, 1.05, 1.06, 1.07, 1.08, 1.09, or 1.10.

The present invention further provides peptides comprising or consisting of the amino acid sequence $$HX_2QGTX_6TSDX_{10}SX_{12}YLX_{15}X_{16}RX_{18}AQDFVQWLX_{27}DT$$
(SEQ ID NO: 20)

Wherein $X_2$ is D-serine, L-alanine, α-aminoisobutyric acid (Aib), or 1-amino-cyclobutane carboxylic acid; $X_6$ is L-phenylalanine, para-fluoro phenylalanine or threo-β-phenylserine; $X_{10}$ is L-lysine or para-aminomethyl phenylalanine; $X_{12}$ is L-lysine or L-leucine; $X_{15}$ is L-glutamic acid or L-leucine; $X_{16}$ is L-alanine, Aib, L-glutamic acid, or L-valine; $X_{18}$ is L-alanine or L-arginine; $X_{27}$ is L-leucine, methionine sulfone, or L-norleucine; the amino acid at position 10 is conjugated to a palmitoyl group by either a gamma-glutamic acid (γE) spacer or a gamma-glutamic acid-gamma-glutamic acid dipeptide (γEγE) spacer; and, the peptide optionally includes a protecting group that, if present, is joined to the C-terminal carboxy group of the peptide; with the proviso that the peptides do not include a peptide having the amino acid sequence of SEQ ID NO:21, and a pharmaceutically acceptable carrier. The peptides are co-agonists of the glucagon receptor and the GLP-1 receptor and have a ratio of $EC_{50}$ at the glucagon receptor to $EC_{50}$ at the GLP-1 receptor of about 0.88 to about 1.25, about 0.90 to about 1.25, about 0.90 to about 1.10, about 0.90 to about 1.00, or about 1.0±0.12. The peptides are co-agonist of the glucagon receptor and the GLP-1 receptor and have a ratio of $EC_{50}$ at the glucagon receptor to $EC_{50}$ at the GLP-1 receptor of 0.88, 0.89, 0.90, 0.91, 0.92, 0.93, 0.94, 0.95, 0.96, 0.97, 0.98, 0.99, 1.00, 1.01, 1.02, 1.03, 1.04, 1.05, 1.06, 1.07, 1.08, 1.09, or 1.10.

The present invention further provides a peptide comprising the amino acid sequence of native human glucagon having the amino acid sequence shown in SEQ ID NO:1 but in which the L-serine at position 2 is replaced with a D-serine; the tyrosine at position 10 is replaced with (i) L-lysine conjugated to a palmitoyl group by either a gamma-glutamic acid (γE) spacer or a gamma-glutamic acid-gamma-glutamic acid dipeptide (γEγE) spacer or (ii) para-aminomethyl phenylalanine conjugated to a palmitoyl group by either a gamma-glutamic acid (γE) spacer or a gamma-glutamic acid-gamma-glutamic acid dipeptide (γEγE) spacer; and up to six additional amino acid substitutions; wherein the peptide is an co-agonist of the glucagon receptor and the GLP-1 receptor and has a ratio of $EC_{50}$ at the glucagon receptor to $EC_{50}$ at the GLP-1 receptor of about 0.88 to about 1.25, about 0.90 to about 1.25, about 0.90 to about 1.10, about 0.90 to about 1.00, or about 1.0±0.12, and wherein the peptide optionally includes a protecting group that, if present, is joined to the C-terminal carboxy group of the peptide; with the proviso that the peptide does not have the amino acid sequence of SEQ ID NO:21.

In particular aspects, the serine at position 16 is replaced with D-alanine or L-alanine, the arginine at position 18 is replaced with L-alanine, the methionine at position 27 is replaced with L-leucine, the asparagine at position 29 is replaced with L-leucine, or combinations thereof.

In particular aspects, the serine at position 16 is replaced with D-alanine or L-alanine, the arginine at position 18 is replaced with L-alanine, the methionine at position 27 is replaced with L-leucine, and the asparagine at position 29 is replaced with L-leucine.

The present invention further provides a composition comprising (i) a peptide having or consisting of the amino acid sequence of native human glucagon as shown in SEQ ID NO:1 but in which the L-serine at position 2 is replaced with a D-serine; the tyrosine at position 10 is replaced with (i) L-lysine conjugated to a palmitoyl group by either a gamma-glutamic acid (γE) spacer or a gamma-glutamic acid-gamma-glutamic acid dipeptide (γEγE) spacer or (ii) para-aminomethyl phenylalanine conjugated to a palmitoyl group by either a gamma-glutamic acid (γE) spacer or a gamma-glutamic acid-gamma-glutamic acid dipeptide (γEγE) spacer; and up to six additional amino acid substitutions; wherein the peptide is an co-agonist of the glucagon receptor and the GLP-1 receptor and has a ratio of $EC_{50}$ at the glucagon receptor to $EC_{50}$ at the GLP-1 receptor of about 0.88 to about 1.25, about 0.90 to about 1.25, about 0.90 to about 1.10, about 0.90 to about 1.00, or about 1.0±0.12, and wherein the peptide optionally includes a protecting group that, if present, is joined to the C-terminal carboxy group of the peptide, and (ii) a pharmaceutically acceptable carrier; with the proviso that the peptide does not have the amino acid sequence of SEQ ID NO:21.

The present invention further includes compositions comprising or consisting of one or more of the peptides shown in Table 1 and a pharmaceutically acceptable carrier.

Pharmaceutical Compositions

Further provided are pharmaceutical compositions comprising a therapeutically effective amount of one or more of the co-agonist peptides disclosed herein for the treatment of a metabolic disorder in an individual. Such disorders include, but are not limited to, obesity, metabolic syndrome or syndrome X, type II diabetes, complications of diabetes such as retinopathy, hypertension, dyslipidemias, cardiovascular disease, gallstones, osteoarthritis, and certain forms of cancers. The obesity-related disorders herein are associated with, caused by, or result from obesity.

"Obesity" is a condition in which there is an excess of body fat. The operational definition of obesity is based on the Body Mass Index (BMI), calculated as body weight per height in meters squared (kg/m2). "Obesity" refers to a condition whereby an otherwise healthy subject has a Body Mass Index (BMI) greater than or equal to 30 kg/m2, or a condition whereby a subject with at least one co-morbidity has a BMI greater than or equal to 27 kg/m2. An "obese subject" is an otherwise healthy subject with a Body Mass Index (BMI) greater than or equal to 30 kg/m2 or a subject with at least one co-morbidity with a BMI greater than or equal to 27 kg/m2. A "subject at risk for obesity" is an otherwise healthy subject with a BMI of 25 kg/m2 to less than 30 kg/m2 or a subject with at least one co-morbidity with a BMI of 25 kg/m2 to less than 27 kg/m2.

The increased risks associated with obesity occur at a lower Body Mass Index (BMI) in Asians. In Asian countries, including Japan, "obesity" refers to a condition whereby a subject with at least one obesity-induced or obesity-related co-morbidity that requires weight reduction or that would be improved by weight reduction, has a BMI greater than or equal to 25 kg/m2. In Asian countries, including Japan, an "obese subject" refers to a subject with at least one obesity-induced or obesity-related co-morbidity that requires weight reduction or that would be improved by weight reduction, with a BMI greater than or equal to 25 kg/m2. In Asian countries, a "subject at risk of obesity" is a subject with a BMI of greater than 23 kg/m2 to less than 25 kg/m2.

As used herein, the term "obesity" is meant to encompass all of the above definitions of obesity.

Obesity-induced or obesity-related co-morbidities include, but are not limited to, diabetes, non-insulin dependent diabetes mellitus—type 2, impaired glucose tolerance, impaired fasting glucose, insulin resistance syndrome, dyslipidemia, hypertension, hyperuricacidemia, gout, coronary artery disease, myocardial infarction, angina pectoris, sleep apnea syndrome, Pickwickian syndrome, non-alcoholic fatty liver disease (NAFLD), non-alcoholic steatohepatitis (NASH), fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

"Treatment" (of obesity and obesity-related disorders) refers to the administration of the compounds of the present invention to reduce or maintain the body weight of an obese subject. One outcome of treatment may be reducing the body weight of an obese subject relative to that subject's body weight immediately before the administration of the compounds of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

"Prevention" (of obesity and obesity-related disorders) refers to the administration of the compounds of the present invention to reduce or maintain the body weight of a subject at risk of obesity. One outcome of prevention may be reducing the body weight of a subject at risk of obesity relative to that subject's body weight immediately before the administration of the compounds of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

The obesity-related disorders herein are associated with, caused by, or result from obesity. Examples of obesity-related disorders include overeating and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovarian disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g., children with acute lymphoblastic leukemia. Further examples of obesity-related disorders are metabolic syndrome, also known as syndrome X, insulin resistance syndrome, sexual and reproductive dysfunction, such as infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer. The compounds of the present invention are also useful for reducing the risk of secondary outcomes of obesity, such as reducing the risk of left ventricular hypertrophy.

The term "diabetes," as used herein, includes both insulin-dependent diabetes mellitus (IDDM, also known as type I diabetes) and non-insulin-dependent diabetes mellitus (NIDDM, also known as Type II diabetes). Type I diabetes, or insulin-dependent diabetes, is the result of an absolute deficiency of insulin, the hormone which regulates glucose utilization. Type II diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type II diabetics are also obese. The compounds of the present invention are useful for treating both Type I and Type II diabetes. The compounds are especially effective for treating Type II diabetes. The compounds of the present invention are also useful for treating and/or preventing gestational diabetes mellitus.

U.S. Pat. No. 6,852,690, which is incorporated herein by reference in its entirety, discloses methods for enhancing metabolism of nutrients comprising administering to a non-diabetic patient a formulation comprising a nutritively effective amount of one or more nutrients or any combination thereof and one or more insulinotropic peptides. The co-agonist peptides disclosed herein are insulinotropic and can be administered to patients with a disturbed glucose metabolism such as insulin resistance but no overt diabetes, as well as patients who for any reason cannot receive nutrition through the alimentary canal. Such patients include surgery patients, comatose patients, patients in shock, patients with gastrointestinal disease, patients with digestive hormone disease, and the like. In particular, obese patients, atherosclerotic patients, vascular disease patients, patients with gestational diabetes, patients with liver disease such as liver cirrhosis, patients with acromegaly, patients with glucorticoid excess such as cortisol treatment or Cushings disease, patients with activated counterregulatory hormones such as would occur after trauma, accidents and surgery and the like, patients with hypertriglyceridemia and patients with chronic pancreatitis can be readily and suitably nourished according to the invention without subjecting the patient to hypo- or hyperglycemia. In particular, the administration to such a patient aims to provide a therapy to as rapidly as possible deliver the nutritional and caloric requirements to the patient while maintaining his plasma glucose below the so-called renal threshold of about 160 to 180 milligrams per deciliter of glucose in the blood. Although normal patients not having glucose levels just below the renal threshold can also be treated according to the invention as described above, patients with disturbed glucose metabolism such as hyperglycemic patients whose plasma glucose level is just above the renal threshold also find the therapy suitable for their condition. In particular, such patients who have a degree of hyperglycemia below the renal threshold at intermittent intervals can receive a combination treatment of nutrients plus insulinotropic peptides according to any of the following regimens. Normal patients not suffering from such hyperglycemia can also be treated using the peptide analogs disclosed herein.

The co-agonist peptides disclosed herein may be used in a pharmaceutical composition when combined with a pharmaceutically acceptable carrier. Such compositions comprise a therapeutically-effective amount of one or more of the co-agonist peptides disclosed herein and a pharmaceutically acceptable carrier. Such a composition may also be comprised of (in addition to the co-agonist peptides disclosed herein and a carrier) diluents, fillers, salts, buffers, stabilizers, solubilizers, and other materials well known in the art. Compositions comprising the co-agonist peptides disclosed herein can be administered, if desired, in the form of salts provided the salts are pharmaceutically acceptable. Salts may be prepared using standard procedures known to those skilled in the art of synthetic organic chemistry. The co-agonist peptides disclosed herein may be in multimers (for example, heterodimers or homodimers) or complexes with itself or other peptides. As a result, pharmaceutical compositions of the invention may comprise one or more co-agonist peptides disclosed herein in such multimeric or complexed form.

The pharmacological composition can comprise one or more co-agonist peptides disclosed herein; one or more co-agonist peptides disclosed herein and one or more other agents for treating a metabolic disorder; or the pharmacological composition comprising the one or more co-agonist peptides disclosed herein can be used concurrently with a pharmacological composition comprising an agent for treating a metabolic disorder. Such disorders include, but are not limited to, obesity, metabolic syndrome or syndrome X, type II diabetes, complications of diabetes, hypertension, dyslipidemias, cardiovascular disease, gallstones, osteoarthritis, and certain forms of cancers.

When the pharmacological composition comprises another agent for treating a metabolic disorder or the treatment includes a second pharmacological composition comprising an agent for treating a metabolic disorder, the agent includes, but are not limited to, cannabinoid (CB1) receptor antagonists, glucagon like peptide 1 (GLP-1) receptor agonists, glucagon receptor antagonists, lipase inhibitors, leptin, tetrahydrolipstatin, 2-4-dinitrophenol, acarbose, sibutramine, phentamine, fat absorption blockers, simvastatin, mevastatin, ezetimibe, atorvastatin, sitagliptin, metformin, orlistat, Qnexa, topiramate, naltrexone, bupriopion, phentermine, losartan, losartan with hydrochlorothiazide, and the like.

Examples of other active ingredients that may be administered separately or in the same pharmaceutical composition in combination with a co-agonist peptide as described herein include, but are not limited to:

(1) other dipeptidyl peptidase-IV (DPP-4) inhibitors (e.g., sitagliptin, alogliptin, linagliptin, vildagliptin, saxagliptin and omarigliptin);

(2) insulin sensitizers, including (i) PPARy agonists, such as the glitazones (e.g. pioglitazone, AMG 131, MBX2044, mitoglitazone, lobeglitazone, IDR-105, rosiglitazone, and balaglitazone), and other PPAR ligands, including (1) PPARα/γ dual agonists (e.g., ZYH2, ZYH1, GFT505, chiglitazar, muraglitazar, aleglitazar, sodelglitazar, and naveglitazar); (2) PPARα agonists such as fenofibric acid derivatives (e.g., gemfibrozil, clofibrate, ciprofibrate, fenofibrate, bezafibrate), (3) selective PPARγ modulators (SPPARγM's), (e.g., such as those disclosed in WO 02/060388, WO 02/08188, WO 2004/019869, WO 2004/020409, WO 2004/020408, and WO 2004/066963); and (4) PPARγ partial agonists; (ii) biguanides, such as metformin and its pharmaceutically acceptable salts, in particular, metformin hydrochloride, and extended-release formulations thereof, such as Glumetza™, Fortamet™, and GlucophageXR™; and (iii) protein tyrosine phosphatase-1B (PTP-1B) inhibitors (e.g., ISIS-113715 and TTP814);

(3) insulin or insulin analogs (e.g., insulin detemir, insulin glulisine, insulin degludec, insulin glargine, insulin lispro and inhalable formulations of each);

(4) leptin and leptin derivatives and agonists;

(5) amylin and amylin analogs (e.g., pramlintide);

(6) sulfonylurea and non-sulfonylurea insulin secretagogues (e.g., tolbutamide, glyburide, glipizide, glimepiride, mitiglinide, meglitinides, nateglinide and repaglinide);

(7) α-glucosidase inhibitors (e.g., acarbose, voglibose and miglitol);

(8) glucagon receptor antagonists (e.g., such as those disclosed in WO 98/04528, WO 99/01423, WO 00/39088, and WO 00/69810);

(9) incretin mimetics, such as GLP-1, GLP-1 analogs, derivatives, and mimetics; and GLP-1 receptor agonists (e.g., dulaglutide, semaglutide, albiglutide, exenatide, liraglutide, lixisenatide, taspoglutide, CJC-1131, and BIM-51077, including intranasal, transdermal, and once-weekly formulations thereof);

(10) LDL cholesterol lowering agents such as (i) HMG-CoA reductase inhibitors (e.g., simvastatin, lovastatin, pravastatin, crivastatin, fluvastatin, atorvastatin, pitavastatin and rosuvastatin), (ii) bile acid sequestering agents (e.g., colestilan, colestimide, colesevalam hydrochloride, colestipol, cholestyramine, and dialkylaminoalkyl derivatives of a cross-linked dextran), (iii) inhibitors of cholesterol absorption, (e.g., ezetimibe), and (iv) acyl CoA:cholesterol acyltransferase inhibitors, (e.g., avasimibe);

(11) HDL-raising drugs, (e.g., niacin and nicotinic acid receptor agonists, and extended-release versions thereof; MK-524A, which is a combination of niacin extended-release and the DP-1 antagonist MK-524);

(12) antiobesity compounds;

(13) agents intended for use in inflammatory conditions, such as aspirin, non-steroidal anti-inflammatory drugs or NSAIDs, glucocorticoids, and selective cyclooxygenase-2 or COX-2 inhibitors;

(14) antihypertensive agents, such as ACE inhibitors (e.g., lisinopril, enalapril, ramipril, captopril, quinapril, and tandolapril), A-II receptor blockers (e.g., losartan, candesartan, irbesartan, olmesartan medoxomil, valsartan, telmisartan, and eprosartan), renin inhibitors (e.g., aliskiren), beta blockers, and calcium channel blockers;

(15) glucokinase activators (GKAs) (e.g., AZD6370);

(16) inhibitors of 11β-hydroxysteroid dehydrogenase type 1, (e.g., such as those disclosed in U.S. Pat. No. 6,730,690, and LY-2523199);

(17) CETP inhibitors (e.g., anacetrapib, and torcetrapib);

(18) inhibitors of fructose 1,6-bisphosphatase, (e.g., such as those disclosed in U.S. Pat. Nos. 6,054,587; 6,110,903; 6,284,748; 6,399,782; and 6,489,476);

(19) inhibitors of acetyl CoA carboxylase-1 or 2 (ACCT or ACC2);

(20) AMP-activated Protein Kinase (AMPK) activators;

(21) other agonists of the G-protein-coupled receptors: (i) GPR-109, (ii) GPR-119 (e.g., MBX2982 and PSN821), and (iii) GPR-40 (e.g., TAK875, 5-[4-[[(1R)-4-[6-(3-hydroxy-3-methylbutoxy)-2-methylpyridine-3-yl]-2,3-dihydro-1H-indene-1-yl]oxy]phenyl]isothiazole-3-ol 1-oxide, 5-(4-((3-(2,6-dimethyl-4-(3-(methylsulfonyl)propoxy)phenyl)phenyl)methoxy)phenyl)iso, 5-(4-((3-(2-methyl-6-(3-hydroxypropoxy)pyridine-3-yl)-2-methylphenyl)methoxy)phenyl)isothiazole-3-ol 1-oxide, and 5-[4-[[3-[4-(3-aminopropoxy)-2,6-dimethylphenyl]phenyl]methoxy]phenyl]isothiazole-3-ol 1-oxide);

(22) SSTR3 antagonists (e.g., such as those disclosed in WO 2009/001836);

(23) neuromedin U receptor agonists (e.g., such as those disclosed in WO 2009/042053, including, but not limited to, neuromedin S (NMS));

(24) SCD inhibitors;

(25) GPR-105 antagonists (e.g., such as those disclosed in WO 2009/000087);

(26) SGLT inhibitors (e.g., ASP1941, SGLT-3, empagliflozin, dapagliflozin, canagliflozin, BI-10773, PF-04971729, remogloflozin, TS-071, tofogliflozin, ipragliflozin, and LX-4211);

(27) inhibitors of acyl coenzyme A:diacylglycerol acyltransferase 1 and 2 (DGAT-1 and DGAT-2);

(28) inhibitors of fatty acid synthase;

(29) inhibitors of acyl coenzyme A:monoacylglycerol acyltransferase 1 and 2 (MGAT-1 and MGAT-2);

(30) agonists of the TGR5 receptor (also known as GPBAR1, BG37, GPCR19, GPR131, and M-BAR);

(31) ileal bile acid transporter inhibitors;

(32) PACAP, PACAP mimetics, and PACAP receptor 3 agonists;

(33) PPAR agonists;

(34) protein tyrosine phosphatase-1B (PTP-1B) inhibitors;

(35) IL-1b antibodies, (e.g., XOMA052 and canakinumab); and

(36) bromocriptine mesylate and rapid-release formulations thereof.

Of particular interest are metformin hydrochloride, pioglitazone, rosiglitazone, simvastatin, atorvastatin, or a sulfonylurea.

Antiobesity compounds that can be combined with compounds as disclosed herein include topiramate; zonisamide; naltrexone; phentermine; bupropion; the combination of bupropion and naltrexone; the combination of bupropion and zonisamide; the combination of topiramate and phentermine; fenfluramine; dexfenfluramine; sibutramine; lipase inhibitors, such as orlistat and cetilistat; melanocortin receptor agonists, in particular, melanocortin-4 receptor agonists; CCK-1 agonists; melanin-concentrating hormone (MCH) receptor antagonists; neuropeptide $Y_1$ or $Y_5$ antagonists (such as MK-0557); CB1 receptor inverse agonists and antagonists (such as rimonabant and taranabant); $\beta_3$ adrenergic receptor agonists; ghrelin antagonists; bombesin receptor agonists (such as bombesin receptor subtype-3 agonists); and 5-hydroxytryptamine-2c (5-HT2c) agonists, such as lorcaserin. For a review of anti-obesity compounds that can be combined with compounds of the present invention, see Chaki et al., "Recent advances in feeding suppressing agents: potential therapeutic strategy for the treatment of obesity," Expert Opin. Ther. Patents, 11: 1677-1692 (2001); Spanswick and Lee, "Emerging antiobesity drugs," Expert Opin. Emerging Drugs, 8: 217-237 (2003); Fernandez-Lopez, et al., "Pharmacological Approaches for the Treatment of Obesity," Drugs, 62: 915-944 (2002); and Gadde, et al., "Combination pharmaceutical therapies for obesity," Exp. Opin. Pharmacother., 10: 921-925 (2009).

In another aspect of the invention, a pharmaceutical composition is disclosed which comprises one or more of the following agents:

(a) a compound as disclosed herein, e.g. a one or co-agonists as disclosed herein wherein each co-agonist may independently be a peptide comprising the amino acid sequence of SEQ ID NO:20 with the proviso that the peptide does not have the amino acid sequence of SEQ ID NO:21;

(b) one or more compounds selected from the group consisting of:

(1) other dipeptidyl peptidase-IV (DPP-4) inhibitors;

(2) insulin sensitizers, including (i) PPARγ agonists, such as the glitazones (e.g. AMG 131, MBX2044, mitoglitazone, lobeglitazone, IDR-105, pioglitazone, rosiglitazone, and balaglitazone) and other PPAR ligands, including (1) PPARα/γ dual agonists, such as ZYH1, YYH2, chiglitazar, GFT505, muraglitazar, aleglitazar, sodelglitazar, and naveglitazar, (2) PPARa agonists, such as fenofibric acid derivatives (e.g., gemfibrozil, clofibrate, ciprofibrate, fenofibrate and bezafibrate), (3) selective PPARγ modulators (SPPARγM's), and (4) PPARγ partial agonists; (ii) biguanides, such as metformin and its pharmaceutically acceptable salts, in particular, metformin hydrochloride, and extended-release formulations thereof, such as Glumetza®, Fortamet®, and GlucophageXR®; (iii) protein tyrosine phosphatase-1B (PTP-1B) inhibitors, such as ISI-113715, and TTP814;

(3) sulfonylurea and non-sulfonylurea insulin secretagogues, (e.g., tolbutamide, glyburide, glipizide, glimepiride, mitiglinide, and meglitinides, such as nateglinide and repaglinide);

(4) α-glucosidase inhibitors (e.g., acarbose, voglibose and miglitol);

(5) glucagon receptor antagonists;

(6) LDL cholesterol lowering agents such as (i) HMG-CoA reductase inhibitors (e.g., lovastatin, simvastatin, pravastatin, cerivastatin, fluvastatin, atorvastatin, pitavastatin, and rosuvastatin), (ii) bile acid sequestering agents (e.g., colestilan, cholestyramine, colestimide, colesevelam hydrochloride, colestipol, and dialkylaminoalkyl derivatives of a cross-linked dextran), (iii) inhibitors of cholesterol absorption, (e.g., ezetimibe), and (iv) acyl CoA: cholesterol acyltransferase inhibitors (e.g., avasimibe);

(7) HDL-raising drugs, such as niacin or a salt thereof and extended-release versions thereof; MK-524A, which is a combination of niacin extended-release and the DP-1 antagonist MK-524; and nicotinic acid receptor agonists;

(8) antiobesity compounds;

(9) agents intended for use in inflammatory conditions, such as aspirin, non-steroidal anti-inflammatory drugs (NSAIDs), glucocorticoids, and selective cyclooxygenase-2 (COX-2) inhibitors;

(10) antihypertensive agents, such as ACE inhibitors (e.g., enalapril, lisinopril, ramipril, captopril, quinapril, and tandolapril), A-II receptor blockers (e.g., losartan, candesartan, irbesartan, olmesartan medoxomil, valsartan, telmisartan, and eprosartan), renin inhibitors (e.g., aliskiren), beta blockers (e.g., calcium channel blockers);

(11) glucokinase activators (GKAs) (e.g., AZD6370);
(12) inhibitors of 11β-hydroxysteroid dehydrogenase type 1 (e.g., such as those disclosed in U.S. Pat. No. 6,730,690; WO 03/104207; and WO 04/058741);
(13) inhibitors of cholesteryl ester transfer protein (CETP), (e.g., torcetrapib and MK-0859);
(14) inhibitors of fructose 1,6-bisphosphatase (e.g., such as those disclosed in U.S. Pat. Nos. 6,054,587; 6,110,903; 6,284,748; 6,399,782; and 6,489,476);
(15) inhibitors of acetyl CoA carboxylase-1 or 2 (ACCT or ACC2);
(16) AMP-activated Protein Kinase (AMPK) activators;
(17) agonists of the G-protein-coupled receptors: (i) GPR-109, (ii) GPR-119 (e.g., MBX2982, and PSN821), and (iii) GPR-40 (e.g., TAK875, 5-[4-[[(1R)-4-[6-(3-hydroxy-3-methylbutoxy)-2-methylpyridine-3-yl]-2,3-dihydro-1H-indene-1-yl]oxy]phenyl]isothiazole-3-ol 1-oxide, 5-(4-((3-(2,6-dimethyl-4-(3-(methylsulfonyl)propoxy)phenyl)phenyl)methoxy)phenyl)iso, 5-(4-((3-(2-methyl-6-(3-hydroxypropoxy)pyridine-3-yl)-2-methylphenyl)methoxy)phenyl)isothiazole-3-ol 1-oxide, and 5-[4-[[3-[4-(3-aminopropoxy)-2,6-dimethylphenyl]phenyl]methoxy]phenyl]isothiazole-3-ol 1-oxide);
(18) SSTR3 antagonists (e.g., such as those disclosed in WO 2009/011836);
(19) neuromedin U receptor agonists (e.g., such as those disclosed in WO2009/042053, including, but not limited to, neuromedin S (NMS));
(20) inhibitors of stearoyl-coenzyme A delta-9 desaturase (SCD);
(21) GPR-105 antagonists (e.g., such as those disclosed in WO 2009/000087);
(22) inhibitors of glucose uptake, such as sodium-glucose transporter (SGLT) inhibitors and its various isoforms, such as SGLT-1; SGLT-2 (e.g., ASP1941, TS071, BI10773, tofogliflozin, LX4211, canagliflozin, dapagliflozin and remogliflozin; and SGLT-3);
(23) inhibitors of acyl coenzyme A:diacylglycerol acyltransferase 1 and 2 (DGAT-1 and DGAT-2);
(24) inhibitors of fatty acid synthase;
(25) inhibitors of acyl coenzyme A:monoacylglycerol acyltransferase 1 and 2 (MGAT-1 and MGAT-2);
(26) agonists of the TGR5 receptor (also known as GPBAR1, BG37, GPCR19, GPR131, and M-BAR);
(28) bromocriptine mesylate and rapid-release formulations thereof, and
(29) IL-1b antibodies (e.g., XOMA052, and canakinumab); and
(c) a pharmaceutically acceptable carrier.

When a co-agonist peptide of the present invention is used contemporaneously with one or more other drugs, peptides, or proteins, a pharmaceutical composition containing such other drugs, peptides, or proteins in addition to the co-agonist peptide of the present invention may be provided. Accordingly, the pharmaceutical compositions of the present invention include those that also contain one or more other active ingredients, in addition to a co-agonist peptide of the present invention.

Methods of administrating the pharmacological compositions comprising the one or more co-agonist peptides disclosed herein to an individual include, but are not limited to, intradermal, intramuscular, intraperitoneal, intravenous, subcutaneous, intranasal, epidural, and oral routes. The compositions can be administered by any convenient route, for example by infusion or bolus injection, by absorption through epithelial or mucocutaneous linings (for example, oral mucosa, rectal and intestinal mucosa, and the like), ocular, and the like and can be administered together with other biologically-active agents. Administration can be systemic or local. In addition, it may be advantageous to administer the composition into the central nervous system by any suitable route, including intraventricular and intrathecal injection. Intraventricular injection may be facilitated by an intraventricular catheter attached to a reservoir (for example, an Ommaya reservoir). Pulmonary administration may also be employed by use of an inhaler or nebulizer, and formulation with an aerosolizing agent. It may also be desirable to administer the one or more co-agonist peptides disclosed herein locally to the area in need of treatment; this may be achieved by, for example, and not by way of limitation, local infusion during surgery, topical application, by injection, by means of a catheter, by means of a suppository, or by means of an implant.

Various delivery systems are known and can be used to administer the co-agonist peptides disclosed herein including, but not limited to, encapsulation in liposomes, microparticles, microcapsules; minicells; polymers; capsules; tablets; and the like. In one embodiment, the co-agonist peptides disclosed herein may be delivered in a vesicle, in particular a liposome. In a liposome, the co-agonist peptides disclosed herein are combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,837,028 and 4,737,323. In yet another embodiment, the co-agonist peptides disclosed herein can be delivered in a controlled release system including, but not limited to: a delivery pump (See, for example, Saudek, et al., New Engl. J. Med. 321: 574 (1989) and a semi-permeable polymeric material (See, for example, Howard, et al., J. Neurosurg. 71: 105 (1989)). Additionally, the controlled release system can be placed in proximity of the therapeutic target (for example, the brain), thus requiring only a fraction of the systemic dose. See, for example, Goodson, In: *Medical Applications of Controlled Release*, 1984. (CRC Press, Bocca Raton, Fla.).

The amount of the compositions comprising one or more of the co-agonist peptides disclosed herein which will be effective in the treatment of a particular disorder or condition will depend on the nature of the disorder or condition, and may be determined by standard clinical techniques by those of average skill within the art. In addition, in vitro assays may optionally be employed to help identify optimal dosage ranges. The precise dose to be employed in the formulation will also depend on the route of administration, and the overall seriousness of the disease or disorder, and should be decided according to the judgment of the practitioner and each patient's circumstances. Ultimately, the attending physician will decide the amount of the composition with which to treat each individual patient. Initially, the attending physician will administer low doses of the composition and observe the patient's response. Larger doses of the composition may be administered until the optimal therapeutic effect is obtained for the patient, and at that point the dosage is not increased further. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases. However, suitable dosage ranges for intravenous administration of the compositions comprising the one or more co-agonist peptides disclosed herein are generally about 5-500 micrograms GO of active compound per kilogram (Kg) body weight. Suitable dosage ranges for intranasal administration are generally about 0.01 pg/kg body weight to 1 mg/kg body weight. Effective doses may be extrapolated from dose-response curves derived from in vitro or animal model test systems. Suppositories generally contain active ingredient in the range of 0.5% to 10% by weight; oral formulations preferably contain 10% to 95% active ingredient. Ultimately the attending physician will decide on the appropriate duration of therapy using compositions comprising the one or more co-agonist peptides disclosed herein of the present invention. Dosage will also vary according to the age, weight and response of the individual patient.

Further provided is a pharmaceutical pack or kit, comprising one or more containers filled with one or more of the ingredients of the pharmaceutical compositions and co-agonist peptides disclosed herein. Optionally associated with such container(s) may be a notice in the form prescribed by a governmental agency regulating the manufacture, use or sale of pharmaceuticals or biological products, which notice reflects approval by the agency of manufacture, use or sale for human administration.

Thus, the present invention further provides a pharmaceutical composition comprising (i) a peptide consisting of the amino acid sequence of native human glucagon having the amino acid sequence shown in SEQ ID NO:1 but in which the L-serine at position 2 is replaced with a D-serine; the tyrosine at position 10 is replaced with (i) L-lysine conjugated to a palmitoyl group by either a gamma-glutamic acid (γE) spacer or a gamma-glutamic acid-gamma-glutamic acid dipeptide (γEγE) spacer or (ii) para-aminomethyl phenylalanine conjugated to a palmitoyl group by either a gamma-glutamic acid (γE) spacer or a gamma-glutamic acid-gamma-glutamic acid dipeptide (γEγE) spacer; and up to six additional amino acid substitutions; wherein the peptide is an co-agonist of the glucagon receptor and the GLP-1 receptor and has a ratio of $EC_{50}$ at the glucagon receptor to $EC_{50}$ at the GLP-1 receptor of about 0.88 to about 1.25, about 0.90 to about 1.25, about 0.90 to about 1.10, about 0.90 to about 1.00, or about 1.0±0.12, and wherein the peptide optionally includes a protecting group that, if present, is joined to the C-terminal carboxy group of the peptide, and (ii) a pharmaceutically acceptable carrier; with the proviso that the peptide does not have the amino acid sequence of SEQ ID NO:21.

In particular aspects, the serine at position 16 is replaced with L-alanine, the arginine at position 18 is replaced with L-alanine, the methionine at position 27 is replaced with L-leucine, the asparagine at position 28 is replaced with L-aspartic acid, or combinations thereof.

The present invention further provides a method for treating a patient for obesity metabolic disease comprising administering the patient an effective amount of the peptide of any one of the aforementioned peptides to treat the metabolic disease in the patient.

The present invention further provides method for treating a patient for obesity metabolic disease comprising administering the patient an effective amount of the composition of the aforementioned compositions to treat the metabolic disease in the patient.

In particular aspects, the metabolic disease is diabetes, non-alcoholic fatty liver disease (NAFLD), non-alcoholic steatohepatitis (NASH), or obesity.

In particular aspects, the diabetes is Type I diabetes, Type II diabetes, or gestational diabetes.

In particular aspects, the patient has more than one metabolic disease, for example, diabetes and NASH, NAFLD, or obesity; obesity and NASH or NAFLD; diabetes, NASH, and obesity; diabetes, NAFLD, and obesity; or diabetes and obesity.

The present invention further provides for the use of any one of the aforementioned peptides for manufacture of a medicament for the treatment of obesity metabolic disease.

The present invention further provides for the use of any one of the aforementioned compositions for manufacture of a medicament for the treatment of obesity metabolic disease.

In particular aspects, the metabolic disease is diabetes, non-alcoholic fatty liver disease (NAFLD), non-alcoholic steatohepatitis (NASH), or obesity.

In particular aspects, the diabetes is Type I diabetes, Type II diabetes, or gestational diabetes.

In particular aspects, the medicament is for treatment of more than one metabolic disease, for example, diabetes and NASH, NAFLD, or obesity; obesity and NASH or NAFLD; diabetes, NASH, and obesity; diabetes, NAFLD, and obesity; or diabetes and obesity.

In particular aspects of the compounds disclosed herein the C-terminal protecting group may be an amide or ester. For example, the carboxylic acid of the C-terminal amino acid is replaced with a charge-neutral group, such as an amide or ester.

Further provided is method for treating a metabolic disease in a patient or individual comprising: administering to the patient or individual an effective amount of any one of the aforementioned compositions comprising a co-agonist peptide and administering to the patient or individual an effective amount of a composition comprising an insulin or insulin analog to treat the metabolic disease in the patient or individual.

In particular aspects, the composition comprising the co-agonist peptide is administered at a time prior to the time the composition comprising the insulin or insulin analog is administered. In another aspect, the composition comprising the insulin or insulin analog is administered at a time prior to the time the composition comprising the co-agonist peptide is administered. In a further still aspect, the composition comprising the co-agonist peptide is administered at the same time as the composition comprising the insulin or insulin analog is administered.

In particular aspects, the insulin analog is insulin detemir, insulin glargine, insulin levemir, insulin glulisine, or insulin lispro.

In particular aspects, the metabolic disease is diabetes, non-alcoholic fatty liver disease (NAFLD), non-alcoholic steatohepatitis (NASH), or obesity.

In particular aspects, the diabetes is Type I diabetes, Type II diabetes, or gestational diabetes.

In particular aspects, the patient has more than one metabolic disease, for example, diabetes and NASH, NAFLD, or obesity; obesity and NASH or NAFLD; diabetes, NASH, and obesity; diabetes, NAFLD, and obesity; or diabetes and obesity.

The present invention further provides a composition comprising any one of the aforementioned peptides; an insulin or insulin analog; and, a pharmaceutically acceptable carrier.

The present invention further provides for the use of a composition comprising any one of the aforementioned peptides; an insulin or insulin analog; and, a pharmaceutically acceptable carrier for the treatment of a metabolic disease.

In particular aspects, the metabolic disease is diabetes, non-alcoholic fatty liver disease (NAFLD), non-alcoholic steatohepatitis (NASH), or obesity. In further aspects, the diabetes is Type I diabetes, Type II diabetes, or gestational diabetes.

The present invention further provides for the use of a composition comprising any one of the aforementioned peptides; an insulin or insulin analog; and, a pharmaceutically acceptable carrier for the manufacture of a medicament for the treatment of a metabolic disease.

In particular aspects, the metabolic disease is diabetes, non-alcoholic fatty liver disease (NAFLD), non-alcoholic steatohepatitis (NASH), or obesity. In further aspects, the diabetes is Type I diabetes, Type II diabetes, or gestational diabetes.

The following examples are intended to promote a further understanding of the present invention.

Example 1

Procedure for the synthesis of Co-agonist Peptide 1: His$^1$-D-Ser$^2$-Gln-Gly-Thr-Phe-Thr-Ser-Asp-Lys$^{10}$(γGlu-C$_{16}$)-Ser-Lys-Tyr-Leu-Asp-Ala-Arg-Ala-Ala-Gln-Asp-Phe$^{22}$-Val$^{23}$-Gln-Trp-Leu-Leu-Asp-Thr-CONH$_2$ (SEQ ID NO:6) was as follows.

The peptide was synthesized on a Rink-amide PEG-PS resin, Champion (Biosearch Technologies (150 µmol, loading 0.28 mmol/g) on a Symphony Protein Technologies Inc apparatus.

All the amino acids were dissolved at a 0.3 M concentration in a solution of 0.3M HOBt (Hydroxybenzotriazole) in DMF. The acylation reactions were performed for 1 hour with 5-fold excess of activated amino acid over the resin free amino groups. The amino acids were activated with equimolar amounts of HATU (O-(7-azabenzotriazol-1-yl)-N,N,N', N'-tetramethyluronium hexafluorophosphate) and a 2-fold molar excess of DIEA (diisopropylethylammine) solution 2M in NMP.

Double acylation reactions of 45 minutes were performed from His$^1$ to Trp$^{25}$. The crude peptide (130 mg in 3 ml of DMSO) was purified by reverse-phase HPLC using preparative Waters Delta-Pak™ C-4 cartridges (40×200 mm, 15 µm, 300 Å) and using as eluents (A) 0.1% TFA in water and (B) 0.1% TFA in acetonitrile. The following gradient of eluent B was used: 30% B to 30% B over 5 min, 60% B to 60% B over 20 min-80% B, flow rate 80 mL/min, wavelength 214 nm. Yield 21%, 95% pure.

The final peptide was characterized on an Acquity UPLC Waters Chromatograph, with BEH300 C4 Acquity Waters 2.1×100 mm, 1.7 µm, at 45° C., using H2O, 0.1% TFA (A) and CH3CN, 0.1% TFA (B) as solvents and also characterized by electrospray mass spectrometry on a Acquity SQ Detector (Mw found: 3695.60 Da; Mw expected: 3696.12 Da).

Example 2

Procedure for the synthesis of Co-agonist Peptide 2: His$^1$-D-Ser$^2$-Gln-Gly-Thr-Phe-Thr-Ser-Asp-Lys$^{10}$(γGlu-C$_{16}$)-Ser-Lys-Tyr-Leu-Asp-Val-Arg-Ala-Ala-Gln-Asp-Phe$^{22}$-Val$^{23}$-Gln-Trp-Leu-Leu-Asp-Thr-CONH$_2$ (SEQ ID NO:7) was as follows.

The peptide was synthesized as previously reported for SEQ ID NO: 6/Example 1

The crude peptide (130 mg in 3 ml of DMSO) was purified by reverse-phase HPLC using preparative Waters Delta-Pak™ C-4 cartridges (40×200 mm, 15 µm, 300 Å) and using as eluents (A) 0.1% TFA in water and (B) 0.1% TFA in acetonitrile. The following gradient of eluent B was used: 30% B to 30% B over 5 min, 50% B to 50% B over 20 min-80% B, flow rate 80 mL/min, wavelength 214 nm. Yield 16%, 95% pure.

The final peptide was characterized on an Acquity UPLC Waters Chromatograph, with BEH300 C4 Acquity Waters 2.1×100 mm, 1.7 µm, at 45° C., using H2O, 0.1% TFA (A) and CH3CN, 0.1% TFA (B) as solvents and also characterized by electrospray mass spectrometry on a Acquity SQ Detector (Mw found: 3723.70 Da; Mw expected: 3724.18 Da).

Example 3

Procedure for the synthesis of Co-agonist Peptide 3: His$^1$-D-Ser$^2$-Gln-Gly-Thr-Phe-Thr-Ser-Asp-Lys$^{10}$(γGlu-γGlu-C$_{16}$)-Ser-Lys-Tyr-Leu-Asp-Val-Arg-Ala-Ala-Gln-Asp-Phe$^{22}$-Val$^{23}$-Gln-Trp-Leu-Leu-Asp-Thr-CONH$_2$ (SEQ ID NO:8) was as follows.

The peptide was synthesized as previously reported for Co-agonist Peptide 1. The crude peptide (130 mg in 3 ml of DMSO) was purified by reverse-phase HPLC using preparative Waters Delta-Pak™ C-4 cartridges (40×200 mm, 15 µm, 300 Å) and using as eluents (A) 0.1% TFA in water and (B) 0.1% TFA in acetonitrile. The following gradient of eluent B was used: 30% B to 30% B over 5 min, 30% B to 60% B over 20 min-80% B, flow rate 80 mL/min, wavelength 214 nm. Yield 20%, >90% pure.

The final peptide was characterized on an Acquity UPLC Waters Chromatograph, with BEH300 C4 Acquity Waters 2.1×100 mm, 1.7 µm, at 45° C., using H2O, 0.1% TFA (A) and CH3CN, 0.1% TFA (B) as solvents and the following gradient: 35% to 65% B in 4 min, flow 0.4 mL/min. The peptide was characterized by electrospray mass spectrometry on an Acquity SQ Detector (Mw found: 3852.80 Da; Mw expected: 3853.29 Da).

Example 4

Procedure for the synthesis of Co-agonist Peptide 4: His$^1$-Aib$^2$-Val-Gly-Thr-Phe-Thr-Ser-Asp-Lys$^{10}$(γGlu-γGlu-C$_{16}$)-Ser-Lys-Tyr-Leu-Asp$^{15}$-Aib$^{16}$-Arg-Ala-Ala-Gln-Asp-Phe$^{22}$-Val$^{23}$-Gln-Trp$^{25}$-Leu-Nle-Asp-Thr-CONH$_2$ (SEQ ID NO:9) was as follows.

The peptide was synthesized by standard Solid-phase Peptide Synthesis (SPPS) using Fmoc/t-Bu chemistry. The assembly was performed on a Rink-amide PEG-PS resin, Champion (Biosearch Technologies, 0.28 mmol/g) on a Symphony (Protein Technologies) peptide synthesizer.

All the amino acids were dissolved at a 0.3 M concentration in a solution of 0.3M HOBt (Hydroxybenzotriazole) in DMF. The acylation reactions were performed for 45 min with 5-fold excess of activated amino acid over the resin free amino groups. The amino acids were activated with equimolar amounts of HATU (O-(7-azabenzotriazol-1-yl)-N,N,N', N'-tetramethyluronium hexafluorophosphate) and a 2-fold molar excess of DIEA (diisopropylethylammine) solution 2M in NMP. Double acylation reactions were performed from His¹ to Trp²⁵. During peptide assembly on solid phase, the side chain protecting groups were: tert-butyl for Asp, γGlu, Ser, Thr and Tyr; trityl for Gln and His; tert-butoxycarbonyl for Lys, Trp; and 2,2,4,6,7-pentamethyldihydrobenzofuran-5-sulfonyl for Arg. The Lys at position 10 was introduced as Dde-Lys(Fmoc)-OH so to accomplish side chain derivatization just after assembly of Lys¹⁰ after Fmoc deprotection of the ε-amino group. The Dde-Lys¹⁰ side chain was derivatized with the linker and fatty acid by manual coupling of two Fmoc-Glu-OtBu residues and palmitic acid activated with DIPC and HOAt. The Dde protecting group was removed by treatment with a solution of 2% hydrazine in DMF and the sequence assembly was continued to incorporate residues 1-9. The dry peptide-resin was treated for 2 hr at room temperature with 88% TFA, 5% phenol, 2% triisopropylsilane and 5% water to afford protecting groups deprotection and cleavage from resin. The solution was filtered to remove the resin and the crude peptide solution was precipitated in cold methyl tert-butyl ether (approximately 4 mL peptide solution for 50 mL methyl tert-butyl ether). The peptide pellet was resuspended/washed/centrifuged in cold methyl tertbutyl ether for 2 times. The peptide pellet was dried under vacuum and then dissolved in water/acetonitrile and then lyophilized.

The crude peptide (130 mg in 3 ml of DMSO) was purified by reverse-phase HPLC using preparative Waters Delta-Pak™ C-4 cartridges (40×200 mm, 15 µm, 300 Å) and using as eluents (A) 0.1% TFA in water and (B) 0.1% TFA in acetonitrile. The following gradient of eluent B was used: 30% B to 30% B over 5 min, 30% B to 50% B over 20 min-80% B, flow rate 80 mL/min, wavelength 214 nm. Yield 20%, >90% pure.

The final peptide was characterized on an Acquity UPLC Waters Chromatograph, with BEH300 C4 Acquity Waters 2.1×100 mm, 1.7 µm, at 45° C., using H2O, 0.1% TFA (A) and CH3CN, 0.1% TFA (B) as solvents and the following gradient: 35% to 35% over 1 min, 35 over 65% B in 4 min, flow 0.4 mL/min. The peptide was characterized by electrospray mass spectrometry on a Acquity SQ Detector (Mw found: Da 3807.9; Mw expected: Da 3808.29).

Example 5

Procedure for the synthesis of Co-agonist Peptide 5: His¹-D-Ser²-Gln-Gly-Thr-Phe-Thr-Ser-Asp-Lys¹⁰(γGlu-γGlu-C₁₆)-Ser-Lys-Tyr-Leu-Asp-Ala-Arg-Ala-Ala-Gln-Asp-Phe²²-Val²³-Gln-Trp-Leu-Leu-Asp-Thr-CONH₂ (SEQ ID NO:10) was as follows.

The peptide was synthesized by standard Solid-phase Peptide Synthesis (SPPS) using Fmoc/t-Bu chemistry. The assembly was performed on a Rink-amide PS resin (150 µmol, loading 0.47 mmol/g) on an APEX 396 peptide synthesizer.

All the amino acids were dissolved at a 0.5 M concentration in a solution of 0.5M HOBt (Hydroxybenzotriazole) in DMF. The acylation reactions were performed for 45 min with 5-fold excess of activated amino acid over the resin free amino groups. The amino acids were activated with equimolar amounts of HATU (O-(7-azabenzotriazol-1-yl)-N,N,N', N'-tetramethyluronium hexafluorophosphate) and a 2-fold molar excess of DIEA (diisopropylethylammine) solution 2M in NMP.

Double acylation reactions were performed on His¹, D-Ser², Phe²², Val²³. During peptide assembly on solid phase, the side chain protecting groups were: tert-butyl for Asp, Ser, D-Ser, Thr and Tyr; trityl for Gln and His; tert-butoxy-carbonyl for Lys, Trp; and 2,2,4,6,7-pentamethyldihydrobenzofuran-5-sulfonyl for Arg. The Lys at position 10 was protected by the orthogonal Alloc(allyloxycarbonyl) protecting group.

The N-terminal residue was acylated as Boc-His(Trt)-OH. At the end of the peptide assembly on solid phase, the Alloc protecting group was removed from Lys¹⁰ and side chain derivatization was performed by manual coupling of Fmoc-Glu-OtBu residues and palmitic acid activated with DIPC and HOAt. The dry peptide-resin was treated for 2 hr at room temperature with 88% TFA, 5% phenol, 2% triisopropylsilane and 5% water to afford protecting groups deprotection and cleavage from resin. The solution was filtered to remove the resin and the crude peptide solution was precipitated in cold methyl tert-butyl ether (approximately 4 mL peptide solution for 50 mL methyl tert-butyl ether). The peptide pellet was resuspended/washed/centrifuged in cold methyl tertbutyl ether for 2 times. The peptide pellet was dried under vacuum and then dissolved in water/acetonitrile and then lyophilized.

The crude peptide (130 mg in 3 ml of DMSO) was purified by reverse-phase HPLC using preparative Waters Delta-Pak™ C-4 cartridges (40×200 mm, 15 µm, 300 Å) and using as eluents (A) 0.1% TFA in water and (B) 0.1% TFA in acetonitrile. The following gradient of eluent B was used: 35% B to 35% B over 5 min, 35% B to 55% B over 20 min-80% B, flow rate 80 mL/min, wavelength 214 nm. Yield 30%, 95% pure.

The final peptide was characterized on an Acquity UPLC Waters Chromatograph, with BEH300 C4 Acquity Waters 2.1×100 mm, 1.7 µm, at 45° C., using H2O, 0.1% TFA (A) and CH3CN, 0.1% TFA (B) as solvents and by electrospray mass spectrometry on a Acquity SQ Detector. (Mw found: 3824.4 Da; Mw expected: 3825.24 Da).

Example 6

Comparator Co-agonist Peptide 6: His¹-D-Ser²-Gln-Gly-Thr-Phe-Thr-Ser-Asp-Lys¹⁰(γGlu-γGlu-C₁₆)-Ser-Lys-Tyr-Leu-Asp-Glu-Arg-Ala-Ala-Gln-Asp-Phe²²-Val²³-Gln-Trp-Leu-Leu-Asp-Thr-CONH₂ (SEQ ID NO:11) has the same amino acid sequence as SEQ ID NO:66 in U.S. Published Application No. 20120288511 or SEQ ID NO:19 in U.S. Published Application No. 20140221283 with the exception that in SEQ ID NO:66 and SEQ ID NO:19 the Lys¹⁰ is conjugated to γGlu-C₁₆. U.S. Published Application Nos. 20120288511 and 20140221283 are incorporated herein in their entirety and Co-agonist Peptide 6 was synthesized essentially as described therein.

Example 7

Procedure for the synthesis of Co-agonist Peptide 7: Ac-His¹-Ala²-Gln-Gly-Thr-Phe-Thr-Ser-Asp-Lys¹⁰(γGlu-γGlu-C₁₆)-Ser-Lys-Tyr-Leu-Asp¹⁵-Glu¹⁶-Arg-Ala-Ala-Gln-Asp-Phe²²-Val²³-Gln-Trp²⁵-Leu-Leu-Asp-Thr-CONH₂ (SEQ ID NO:12) was as follows.

The peptide was synthesized as previously reported for Co-agonist Peptide 1 on a Rink-amide PEG-AM resin, (Chemimpex, 0.47 mmol/g). The N-terminal residue was acylated with Acetic anhydride at the end of the peptide assembly on solid phase.

The crude peptide (130 mg in 3 ml of DMSO) was purified by reverse-phase HPLC using preparative Waters Delta-Pak™ C-4 cartridges (40×200 mm, 15 µm, 300 Å) and using as eluents (A) 0.1% TFA in water and (B) 0.1% TFA in acetonitrile. The following gradient of eluent B was used:

25% B to 25% B over 5 min, 25% B to 55% B over 20 min-80% B, flow rate 80 mL/min, wavelength 214 nm. Yield 27%, >90% pure.

The final peptide was characterized on an Acquity UPLC Waters Chromatograph, with BEH300 C4 Acquity Waters 2.1×100 mm, 1.7 µm, at 45° C., using $H_2O$, 0.1% TFA (A) and CH3CN, 0.1% TFA (B) as solvents and the following gradient: 30% to 30% over 1 min, 30 over 70% B in 4 min, flow 0.4 mL/min. The peptide was characterized by electrospray mass spectrometry on a Acquity SQ Detector (Mw found: 3909.31 Da; Mw expected: 3907.8 Da).

Example 8

Procedure for the synthesis of Co-agonist Peptide 8: $His^1$-D-$Ser^2$-Gln-Gly-Thr-Phe-Thr-Ser-Asp-$Lys^{10}$(γGlu-γGlu-$C_{16}$)-Ser-Lys-Tyr-Leu-$Glu^{15}$-$Ala^{16}$-Arg-Ala-Ala-Gln-Asp-$Phe^{22}$-$Val^{23}$-Gln-$Trp^{25}$-Leu-Leu-Asp-Thr-$CONH_2$ (SEQ ID NO:13) was as follows.

The peptide was synthesized by standard Solid-phase Peptide Synthesis (SPPS) using Fmoc/t-Bu chemistry. The assembly was performed on a Rink-amide PEG-AM resin, (Chemimpex, 0.47 mmol/g) or on Rink-amide PEG-PS resin, Champion (Biosearch Technologies, 0.28 mmol/g) on an Overture peptide synthesizer. The acylations were performed using HATU/DIPEA as activators and 45 minutes reaction time. Double acylation reactions were performed on all the sequence. The Lys at position 10 was protected by the orthogonal Alloc(allyloxycarbonyl) protecting group. The N-terminal residue was protected as Boc. At the end of the peptide assembly on solid phase, the Alloc protecting group was removed from $Lys^{10}$ and side chain derivatization was performed by manual coupling of Fmoc-Glu-OtBu residues and palmitic acid activated with DIPC and HOAt. The dry peptide-resin was treated for 2 hr at room temperature with 88% TFA, 5% phenol, 2% triisopropylsilane and 5% water to afford protecting groups deprotection and cleavage from resin. The solution was filtered to remove the resin and the crude peptide solution was precipitated in cold methyl tert-butyl ether (approximately 4 mL peptide solution for 50 mL methyl tert-butyl ether). The peptide pellet was resuspended/washed/centrifuged in cold methyl tertbutyl ether for 2 times. The peptide pellet was dried under vacuum and then dissolved in water/acetonitrile and then lyophilized.

The crude peptides (130 mg in 3 ml of DMSO) were purified by reverse-phase HPLC using preparative Waters Delta-Pak™ C-4 cartridges (40×200 mm, 15 µm, 300 Å) and using as eluents (A) 0.1% TFA in water and (B) 0.1% TFA in acetonitrile. The following gradient of eluent B was used: 35% B to 35% B over 5 min, 35% B to 55% B over 20 min-80% B, flow rate 80 mL/min, wavelength 214 nm Yield 20%, >90% pure. The final peptide was characterized on an Acquity UPLC Waters Chromatograph, with BEH300 C4 Acquity Waters 2.1×100 mm, 1.7 µm, at 45° C., using $H_2O$, 0.1% TFA (A) and CH3CN, 0.1% TFA (B) as solvent. The peptide was characterized by electrospray mass spectrometry on a Acquity SQ Detector (Mw found: 3839.10 Da; Mw expected: 3839.26 Da).

Example 9

Procedure for the synthesis of Co-agonist Peptide 9: $His^1$-D-$Ser^2$-Val-Gly-Thr-$pFF^6$-Thr-Ser-Asp-$Lys^{10}$(γGlu-γGlu-$C_{16}$)-Ser-Lys-Tyr-Leu-$Asp^{15}$-$Glu^{16}$-Arg-Ala-Ala-Gln-Asp-$Phe^{22}$-$Val^{23}$-Gln-$Trp^{25}$-Leu-Leu-Asp-Thr-$CONH_2$ (SEQ ID NO:14) was as follows The peptide was synthesized as previously reported for Co-agonist Peptide 4. Double acylation reactions were performed on $His^1$, D-$Ser^2$, $Val^3$, $Gly^4$, $Thr^5$, $Thr^7$, $Phe^{22}$, $Val^{23}$. Fmoc-p-fluoro-phenylalanine-COOH (Fmoc-pFF-OH) was assembled by manual coupling activated with DIPC and HOAt.

The crude peptide (130 mg in 3 ml of DMSO) was purified by reverse-phase HPLC using preparative Waters Delta-Pak™ C-4 cartridges (40×200 mm, 15 µm, 300 Å) and using as eluents (A) 0.1% TFA in water and (B) 0.1% TFA in acetonitrile. The following gradient of eluent B was used: 30% B to 30% B over 5 min, 30% B to 50% B over 20 min-80% B, flow rate 80 mL/min, wavelength 214 nm. The yield was 10%, and the purity above 90%. The final peptide was characterized on an Acquity UPLC Waters Chromatograph, with BEH300 C4 Acquity Waters 2.1×100 mm, 1.7 µm, at 45° C., using $H_2O$, 0.1% TFA (A) and CH3CN, 0.1% TFA (B) as solvent. The peptide was characterized by electrospray mass spectrometry on a Acquity SQ Detector (Mw found: 3900.80 Da; Mw expected: 3901.26 Da).

Example 10

Procedure for the synthesis of Co-agonist Peptide 10: $His^1$-D-$Ser^2$-Gln-Gly-Thr-Phe-Thr-Ser-Asp-$Lys^{10}$(γGlu-γGlu-$C_{16}$)-Ser-Lys-Tyr-Leu-$Asp^{15}$-$Glu^{16}$-Arg-Ala-Ala-Gln-Asp-$Phe^{22}$-$Val^{23}$-Gln-$Trp^{25}$-Leu-$Met_2$(O)-Asp-Thr-$CONH_2$ (SEQ ID NO:15) was as follows.

The peptide was synthesized as previously reported for Co-agonist Peptide 4. Double acylation reactions were performed on $His^1$, D-$Ser^2$, $Gln^3$, $Gly^4$, $Thr^5$, $Phe^6$, $Thr^7$, $Phe^{22}$, $Val^{23}$. Fmoc-Methionine-sulphone-COOH was assembled by manual coupling activated with DIPC and HOAt. The crude peptide (130 mg in 3 ml of DMSO) was purified by reverse-phase HPLC using preparative Waters Delta-Pak™ C-4 cartridges (40×200 mm, 15 µm, 300 Å) and using as eluents (A) 0.1% TFA in water and (B) 0.1% TFA in acetonitrile. The following gradient of eluent B was used: 30% B to 30% B over 5 min, 30% B to 50% B over 20 min-80% B, flow rate 80 mL/min, wavelength 214 nm. The yield was 15%, and the purity was >90% pure. The final peptide was characterized on an Acquity UPLC Waters Chromatograph, with BEH300 C4 Acquity Waters 2.1×100 mm, 1.7 µm, at 45° C., using $H_2O$, 0.1% TFA (A) and CH3CN, 0.1% TFA (B) as solvent. The peptide was characterized by electrospray mass spectrometry on a Acquity SQ Detector (Mw found: 3932.70 Da; Mw expected: 3933.31 Da).

Example 11

Procedure for the synthesis of Co-agonist Peptide 11: $His^1$-D-$Ser^2$-Gln-Gly-Thr-Phe-Thr-Ser-Asp-$Lys^{10}$(γGlu-γGlu-$C_{16}$)-Ser-Leu-Tyr-Leu-Asp-$Glu^{16}$-Arg-$Ala^{18}$-Ala-Gln-Asp-$Phe^{22}$-$Val^{23}$-Gln-$Trp^{25}$-Leu-Leu-Asp-Thr-$NH_2$ (SEQ ID NO:16) was as follows.

The synthesis started with assembly of linear peptide sequence on solid support, followed by branching Lysine at position 10 with a three-residue sequence of γGlutamic acid-γGlutamic acid-palmitic acid. The completed peptidyl resin was then cleaved in TFA solution. Following RP-HPLC purification, 15 mg of the title compound was afforded from 0.15 mmol of resin.

We used standard solid phase Fmoc/t-Bu chemistry on a CEM Liberty peptide synthesizer (CEM Corp. Matthews, N.C.). The first amino acid Threonine was loaded as Fmoc-Thr (tBu) on MBHA polystyrene resin (0.21 mmol/g in loading, from Midwest Biotech. IN, lot # S16130). A pseudoproline dipeptide Fmoc-PheThr (φMe,φMe) was applied at positions 6 and 7. Position 10 Lysine side chain was protected by ivDde group [1-(4, 4-dimethyl-2, 6-dioxo-cyclohex-1-ylidene) isovaleryl]. Other standard side chain protecting groups were as follows: trityl group for Glutamine; tert-butoxy-carbonyl group for Tryptophan and Histidine; tert-butyl group for Glutamic acid, γ-Glutamic acid, Aspartic acid, Serine and D-Serine, Threonine, and Tyrosine; pbf group (2,2,4,6,7-pentametyldihydrobenzofuran-5-sulfonyl) for Arginine.

Acylation was performed with 5-6 equivalents of amino acids over resin free amino groups. Single-couple was applied in all positions, except for positions $Arg^{17}$, $Ala^{19}$, and $Thr^{29}$, where double-couple was applied. Fmoc-amino acids were activated with an equimolar amount of HATU [2-(1H-9-Azabenzotriazole-1-yl)-1,1,3,3-tetramethyl-aminum hexafluorophosphate] in the presence of 2 equimolar amount of DIEA (N, N-diisopropylethylamine). Fmoc deprotection was carried in 20% piperidine in DMF. Removal of ivDde on Lysine 10 was accomplished manually in 5% of hydrazine DMF solution, 1 minute each for 2 times. Palmitic acid was coupled manually to the sequence in the presence of 10 equimolar amount of DIPC (N, N'-Diisopropylcarbodiimide) and HOAt (1-Hydroxy-7-azabenzotriazole) for 45 min.

The completed resin was cleaved by TFA solution (88% TFA/5% phenol/2% triisopropylsilane/5% water) for 3 hours. During cleavage, we filtered the resin and replenished the TFA solution every hour. We then combined TFA solutions and condensed them on a rotary evaporator. To precipitate peptides, 50 ml of ice-cold diethyl ether was added to TFA residual. The precipitated peptide was pelleted by centrifugation, and the pellets were then washed twice with ice-cold diethyl ether to remove organic scavengers. The final pellets were dried, re-suspended in 30% acetic acid in water, and freeze-dried. Dried peptide crude was re-dissolved in water/acetonitrile. Then the peptide crude was freeze-dried for the second time to remove the impurity attributed by incomplete decarboxylation of Tryptophan residue.

The crude peptide was purified by reverse phase HPLC using a Phenomenex Jupiter C4 column (250×21.2 mm, 10μ, 300 A, catalog #00G-4168-P0-AX) with a water/acetonitrile gradient in the presence of 0.1% trifluoroacetic acid. The purified peptide was characterized by LCMS. The monoisotopic mass determined for the purified peptide was 3868.98 Da (the sequence-predicted mass is 3868.3 Da).

LC-MS was obtained on a UPLC-MS system (Waters ACQUITY); Column: Waters BEH 130 C18 Acquity 1.0×50 mm, 1.7 um; Gradient: 10-99% B linear gradient over 1.6 min, back to 1% B in 0.4 min. A/B buffer system (A=0.1% TFA in water; B=0.1% TFA in acetonitrile); Flow rate: 0.3 ml/min; Temperature: 50 C; UV wavelength: 215 nm; Injection volume: 0.5 ul; Mass scan: 500-1500 m/z, 0.2 sec; Voltages: Capilary (Kv)-3.25; Con (V)-27; Extract (V)-3; RF Lens (V)-0.3; Gas flow (L/hr): Desolvation-597; Cone-30; Temperature (C): Source temp-100; Desolvation temp-350.

Example 12

Procedure for the synthesis of Co-agonist Peptide 12: $His^1$-D-$Ser^2$-Gln-Gly-Thr-Phe-Thr-Ser-Asp-$pAF^{10}$(γGlu-γGlu-$C_{16}$)-Ser-Lys-Tyr-Leu-$Asp^{15}$-$Ala^{16}$-Arg-Ala-Ala-Gln-$Asp$-$Phe^{22}$-$Val^{23}$-Gln-$Trp^{25}$-Leu-Leu-Asp-Thr-$CONH_2$ (SEQ ID NO:17), wherein pAF is para-aminomthyl phenylalanine was as follows.

The peptide was synthesized as previously reported for Co-agonist Peptide 4. Double acylation reactions were performed on $His^1$, D-$Ser^2$, $Val^3$, $Gly^4$, $Thr^5$, $Phe^6$, $Thr^7$, $Phe^{22}$, $Val^{23}$. In position 10 Fmoc-para-aminomethyl phenylalanine-COOH orthogonally protected with Dde (see Example 15) was assembled by manual coupling activated with DIPC and HOAt. At the end of the assembly the Dde protecting group was removed by treatment with a solution of 2% hydrazine in DMF and side chain derivatization was accomplished with the linker and fatty acid by manual coupling of two Fmoc-Glu-OtBu residues and palmitic acid activated with DIPC and HOAt.

The crude peptide (130 mg in 3 ml of DMSO) was purified by reverse-phase HPLC using preparative Waters Delta-Pak™ C-4 cartridges (40×200 mm, 15 μm, 300 Å) and using as eluents (A) 0.1% TFA in water and (B) 0.1% TFA in acetonitrile. The following gradient of eluent B was used: 30% B to 30% B over 5 min, 30% B to 55% B over 20 min-80% B, flow rate 80 mL/min, wavelength 214 nm. Yield 10%, >90% pure.

The final peptide was characterized on an Acquity UPLC Waters Chromatograph, with BEH300 C4 Acquity Waters 2.1×100 mm, 1.7 μm, at 45° C., using H2O, 0.1% TFA (A) and CH3CN, 0.1% TFA (B) as solvents and the following gradient: 35 over 55% B in 4 min, flow 0.4 mL/min. The peptide was characterized by electrospray mass spectrometry on a Acquity SQ Detector (Mw found: 3873.10 Da; Mw expected: 3873.28 Da)

Example 13

Procedure for the synthesis of Co-agonist Peptide 13: $His^1$-amino-1cyclobutane$^2$-Gln-Gly-Thr-Phe-Thr-Ser-Asp-$Lys^{10}$(γGlu-γGlu-$C_{16}$)-Ser-Lys-Tyr-Leu-$Asp^{15}$-$Glu^{16}$-Arg-Ala-Ala-Gln-Asp-$Phe^{22}$-$Val^{23}$-Gln-$Trp^{25}$-Leu-Leu-Asp-Thr-$CONH_2$ (SEQ ID NO:18) was as follows.

The peptide was synthesized as previously reported for SEQ ID NO:9/Example 4. Double acylation reactions were performed on $His^1$, D-$Ser^2$, $Gln^3$, $Gly^4$, $Thr^5$, $Phe^6$, $Thr^7$, $Phe^{22}$, $Val^{23}$. Fmoc-amino-1-cyclobutane carboxylic acid was assembled by manual coupling activated with DIPC and HOAt.

The crude peptide (130 mg in 3 ml of DMSO) was purified by reverse-phase HPLC using preparative Waters Delta-Pak™ C-4 cartridges (40×200 mm, 15 μm, 300 Å) and using as eluents (A) 0.1% TFA in water and (B) 0.1% TFA in acetonitrile. The following gradient of eluent B was used: 35% B to 35% B over 5 min, 35% B to 50% B over 20 min-80% B, flow rate 80 mL/min, wavelength 214 nm. The final peptide was characterized on an Acquity UPLC Waters Chromatograph, with BEH300 C4 Acquity Waters 2.1×100 mm, 1.7 μm, at 45° C., using H2O, 0.1% TFA (A) and CH3CN, 0.1% TFA (B) as solvents The yield was 18%, and the purity >90%. The peptide was characterized by electrospray mass spectrometry on a Acquity SQ Detector (Mw found: 3893.40 Da; Mw expected: 3893.31 Da).

Example 14

Procedure for the synthesis of Co-agonist Peptide 14: $His^1$-D-Ser-Gln-Gly-Thr-tβP-Thr-Ser-Asp-$Lys^{10}$(γGlu-γGlu-$C_{16}$)-Ser-Lys-Tyr-Leu-$Asp^{15}$-$Glu^{16}$-Arg-Ala-Ala-Gln- Asp-Phe²²-Val²³-Gln-Trp²⁵-Leu-Leu-Asp-Thr-CONH₂ (SEQ ID NO:19), wherein tβP=threo-β-Phenylserine, was as follows.

tβP = threo-β-Phenylserine was prepared from (2R, 3S)/(2S, 3R)-Racemic Fmoc-β-hydroxy-phenylalanine:

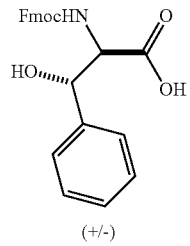

(+/-)

The peptide was synthesized as previously reported for Co-agonist Peptide 4. Double acylation reactions were performed on His¹, D-Ser², Gln³, Gly⁴, Thr⁵, Phe⁶, Thr⁷, Phe²², Val²³. tβP was assembled by manual coupling activated with DIPC and HOAt.

The crude peptide (130 mg in 3 ml of DMSO) in which two isomers were present, due to the racemic tβP used in the synthesis, was purified by reverse-phase HPLC using preparative Waters Delta-Pak™ C-4 cartridges (40×200 mm, 15 μm, 300 Å) and using as eluents (A) 0.1% TFA in water and (B) 0.1% TFA in acetonitrile. The following gradient of eluent B was used: 35% B to 35% B over 5 min, 35% B to 45% B over 20 min-80% B, flow rate 80 mL/min, wavelength 214 nm. The two isomers were separated in the preparative run with different elution times. The most hydrophilic isomer having the shorter retention time t=12.45 was identified with no. L-005472682 on an Acquity UPLC Waters Chromatograph, with BEH300 C18 Acquity Waters 2.1×100 mm, 1.7 μm, at 45° C., using H2O, 0.1% TFA (A) and CH3CN, 0.1% TFA (B) as solvents and the following gradient: 20 over 60% B in 20 min, flow 0.4 mL/min. The product was also characterized by electrospray mass spectrometry on a Acquity SQ Detector Yield 12%, >90% pure (Mw found: 3899.3 Da; Mw expected: 3899.27 Da).

Example 15

Synthesis of Fmoc-4-(Dde-aminomethyl)-phenylalanine was as follows.

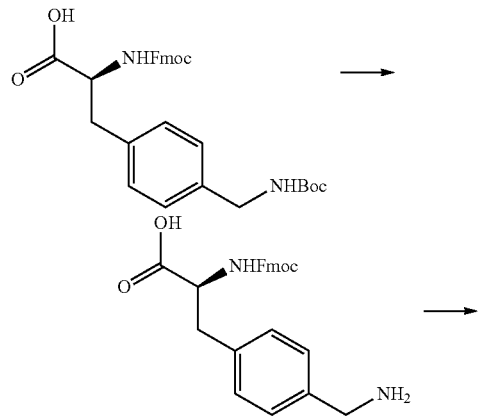

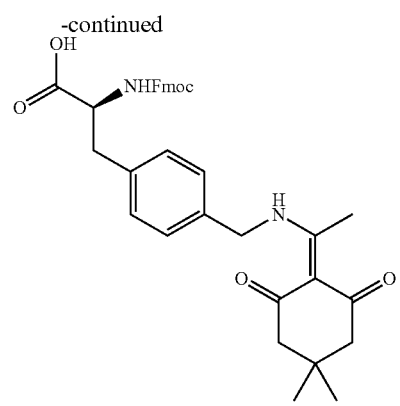

Fmoc-4-(Boc-aminomethyl)-phenylalanine was stirred in DCM/TFA 2/1 for 1 hour. The solvents were removed under reduced pressure and the residue was treated with diethyl ether to obtain a white solid. The crude material obtained was dissolved in EtOH (19 mM), DIPEA (5 eq) and Dimedone (1.1 eq) were added to the reaction mixture. After 3 hours at 60° C. the solution was acidified with TFA to PH 4. The solvents were removed under reduced pressure and the residue was treated with AcOEt and washed with HCl 1N. The organic phase was washed with brine and dried over Na₂SO4. The solvents were removed under reduced pressure and the final product was obtained as yellow solid.

The final compound was characterized on an Acquity UPLC Waters Chromatograph, with BEH300 C18 Acquity Waters 2.1×100 mm, 1.7 μm, at 45° C., using H₂O, 0.1% TFA (A) and CH₃CN, 0.1% TFA (B) as solvents and the following gradient: 10% to 10% B in 1 min, 10% B over 90% B in 4 min, flow 0.4 mL/min. The protected amino acid was characterized by electrospray mass spectrometry on a Acquity SQ Detector (Mw found: 581.5 Da; Mw expected: 580.67 Da).

Example 16

The cAMP protocol was as follows.

Peptides were dissolved in 100% DMSO and serially diluted to generate 11 point titrations. The peptide solutions were then transferred into 384-well assay plates (150 nL/well). Assay ready frozen cells expressing human GLP-1R or human GCGR were suspended in growth media consisting of DMEM/F12 medium (GIBCO), 10% FBS (GIBCO), 1x P/S (GIBCO), 800 μg/mL Geneticin (GIBCO), and 300 μg/mL Hygromycin (Invitrogen). Cells were then diluted in assay buffer consisting of PBS (GIBCO), 7.5% BSA (Perkin Elmer), 100 μM RO 20-1724 (Sigma), and 20% human serum (MP Biomedical). The cell suspensions (15 μL) were then added to the assay plates containing the peptide solutions (30,000 cells/well for human GCGR; 20,000 cells/well for GLP1R). The cells were incubated for 1 hour at room temperature in the dark. Production of cAMP was determined using HitHunter™ cAMPXS kits (DiscoverX). ED buffer (20 μL) was then added to each well and the plates were incubated for 1 hour at room temperature in the dark. Subsequently, EA buffer (20 μL) was added to each well, and the plates were incubated for 1-18 hours at room temperature in the dark. Luminescence was measured using an EnVision Multilabel plate reader (Perkin Elmer). EC₅₀ values were calculated using ADA data analyzer software. The results are shown in Table 2

TABLE 2

| SEQ ID NO: | Peptide | GCGR EC50 (nM) human | GLPR1 EC50 (nM) human | hGCGR/ hGLP1R (hTone) |
|---|---|---|---|---|
| 6 | HsQGTFTSDK(γEC$_{16}$)SKYLDARAAQDFVQWLLDT-NH$_2$ | 0.042 | 0.048 | 0.88 |
| 7 | HsQGTFTSDK(γEγEC$_{16}$)SKYLDVRRAQDFVQWLLDT-NH$_2$ | 0.041 | 0.160 | 0.30 |
| 8 | HsQGTFTSDK(γEγEC$_{16}$)SKYLDVRAAQDFVQWLLDT-NH$_2$ | 0.080 | 0.130 | 0.60 |
| 9 | HUVGTFTSDK(γEγEC$_{16}$)SKYLDURAAQDFVQWLλDT-NH$_2$ | 0.890 | 0.100 | 8.98 |
| 10 | HsQGTFTSDK(γEγEC$_{16}$)SKYLDARAAQDFVQWLLDT-NH$_2$ | 0.030 | 0.033 | 0.90 |
| 11 | HsQGTFTSDK(γEγEC$_{16}$)SKYLDERAAQDFVQWLLDT-NH$_2$ | 0.009 | 0.007 | 1.30 |
| 12 | AcHAQGTFTSDK(γEγEC$_{16}$)SKYLDERAAQDFVQWLLDT-NH$_2$ | 0.070 | 0.070 | 1.00 |
| 13 | HsQGTFTSDK(γEγEC$_{16}$)SKYLEARAAQDFVQWLLDT-NH$_2$ | 0.020 | 0.020 | 0.90 |
| 14 | HsQGTpFFTSDK(γEγEC$_{16}$)SKYLDERAAQDFVQWLLDT-NH$_2$ | 0.050 | 0.060 | 0.93 |
| 15 | HsQGTFTSDK(γEγEC16)SKYLDERAAQDFVQWL2DT-NH$_2$ | 0.020 | 0.020 | 1.10 |
| 16 | HsQGTFTSDK(γEγEC16)SLYLDERAAQDFVQWLLDT-NH$_2$ | 0.060 | 0.060 | 0.91 |
| 17 | HsQGTFTSDpAF(γEγEC16)SKYLDARAAQDFVQWLLDT-NH$_2$ | 0.050 | 0.050 | 0.98 |
| 18 | H‡QGTFTSDK(γEγEC16)SKYLDERAAQDFVQWLLDT-NH$_2$ | 0.060 | 0.050 | 1.25 |
| 19 | HsQGtβPTSDK(γEγEC16)SKYLDERAAQDFVQWLLDT-NH$_2$ | 1.040 | 1.020 | 1.02 | s = D-serine;
U = α-aminoisobutyric acid (Aib);
λ = norleucine (Nle);
pA = para-aminomethyl phenylalanine;
2 = methionine sulfone;
‡ = 1-amino-1-cyclobutane carboxylic acid;
tβP = threo-β-Phenylserine;
Ac = acetyl;
pFF = p-fluorophenylalanine Example 17

Diet induced obesity (DIO) mice have long been used as surrogates for humans in the study of the efficacy of anti-obesity compounds. The results obtained from such mice in the study of obesity compounds are translatable to humans (See for example, Nilsson et al. Acta Pharmacologia Sinica 33: 173-181 (2012), which is incorporated herein by reference in its entirety). Thus, DIO mice are useful surrogates for humans for the testing the efficacy of compounds intended to treat obesity.

For the studies in Examples 18, 19, 20, and 21, diet induced obesity (DIO) mice (strain C57Bl6/NTac; 20 weeks on a high fat diet, about 47 g) were divided into groups of eight mice per group and the initial average body weight, food intake and basal glucose of each group were matched before peptide administration. Each group of mice was subcutaneously injected daily with a dose of Co-agonist Peptide or vehicle control for 7 to 10 days. The peptides tested in this study were Co-agonist Peptides 1, 2, 3, 4, 5, and 6 (SEQ ID NOs: 6, 7, 8, 9, 10, and 11, respectively) at the doses that varied from 3 nmol/kg to 25 nmol/kg. Body weight, food intake and basal glucose were measured periodically during treatment. All peptides have comparable pharmacokinetic properties and similar plasma protein binding.

Example 18

The in vivo effects of certain peptides of the invention were tested in diet-induced obese (DIO) mice (strain C57Bl6/NTac) that were maintained on a high fat diet for 20 weeks and had an initial body weight of about 47 grams. Mice were administered a vehicle control or a dose of a peptide daily for nine days. The peptides in this study included peptides of SEQ ID NOs: 6, 7, 8, 9, 10 and 11 administered at a dose of 9 nmol/kg. The peptide of SEQ ID NO: 9 was administered at doses of 9 and 25 nmol/kg. Cumulative body weight change (grams) was measured each day of the study except on day 3. Results are shown in FIG. 1 and are expressed as mean±SEM. Each of the peptides tested in this study demonstrated a significant ($p<0.05$ vs vehicle, 2way ANOVA) weight loss over the course of the study compared to the vehicle treated groups of mice. On day 9 of the study, mice that were administered 9 nmol/kg of the peptide of SEQ ID NOs: 7 and 9 exhibited an approximate weight loss of 3 grams, while a dose of 25 nmol/kg of the peptide of SEQ ID NO: 9 led to a body weight loss of 10.5 grams. Mice that were administered 9 nmol/kg of the peptide of SEQ ID NOs: 8 and 6 exhibited weight loss of 8 and 10.5 grams, respectively. Mice that were administered 9 nmol/kg of the peptide of SEQ ID NOs: 10 and 11 exhibited approximately 13 grams of weight loss, respectively.

Example 19

Figure 2:
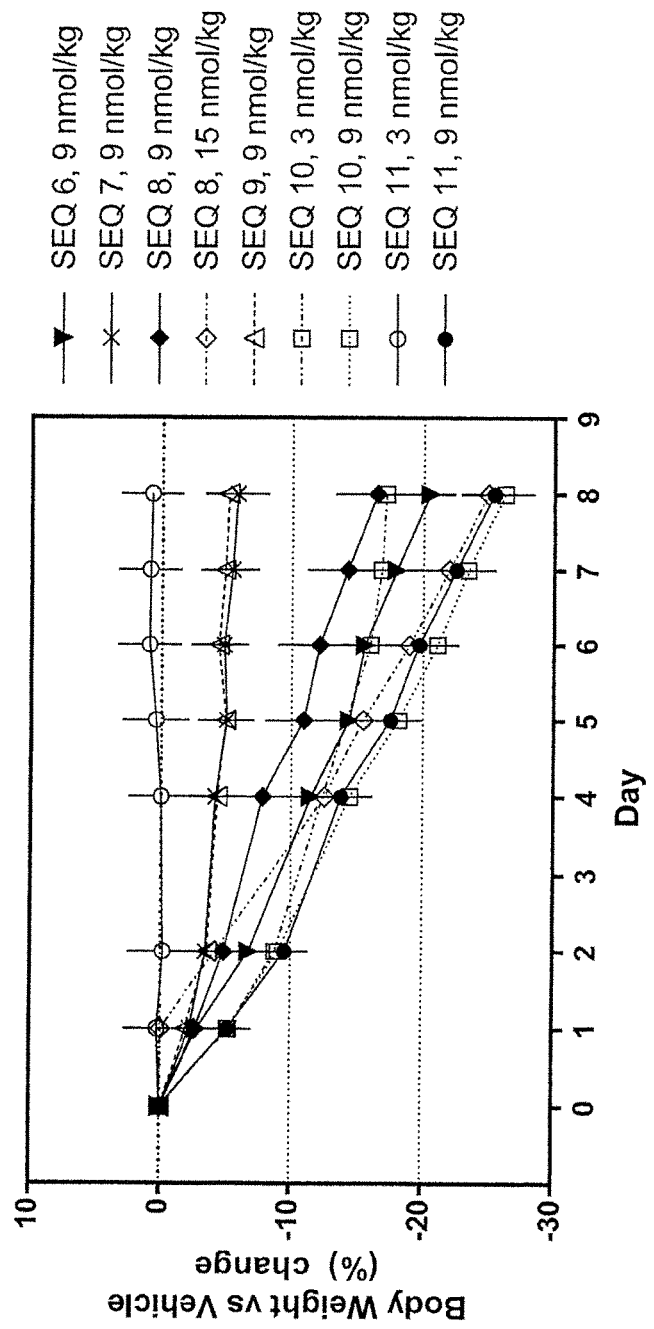
FIG. 2 represents a graph of the cumulative body weight change (%) relative to a vehicle treated control group of DIO mice treated with a daily dose of a peptide of SEQ ID NO: 6 to 11, as detailed in Example 19.

In a second study in DIO mice (strain C57Bl6/NTac) the doses of each peptide were varied—each of the peptides of SEQ ID NOs: 6 to 11 was administered at a dose 9 nmol/kg. In addition, the peptide of SEQ ID NO: 8 was administered at 15 nmol/kg, while the peptide of SEQ ID NOs: 10 and 11 were administered at 3 nmol/kg. Body weight was measured daily for eight days and body weight change is expressed as percent relative to vehicle (FIG. 2). Mice administered a dose of 9 nmol/kg the peptide of SEQ ID NOs: 7 or 9 exhibited approximately 5% weight loss compared to mice administered with a dose of 9 nmol/kg the peptide of SEQ ID NOs: 6 or 8, who exhibited weight loss of approximately 20% or 17% respectively. Mice administered with a dose of 15 nmol/kg the peptide of SEQ ID NO: 8 exhibited weight loss of approximately 25%. Mice administered with a dose 3 nmol/kg the peptide of SEQ ID NO: 10 exhibited weight loss of approximately 17%, while mice administered with a dose of 3 nmol/kg of the peptide of SEQ ID NO: 11, exhibited no weight loss efficacy.

Example 20

Figure 3:
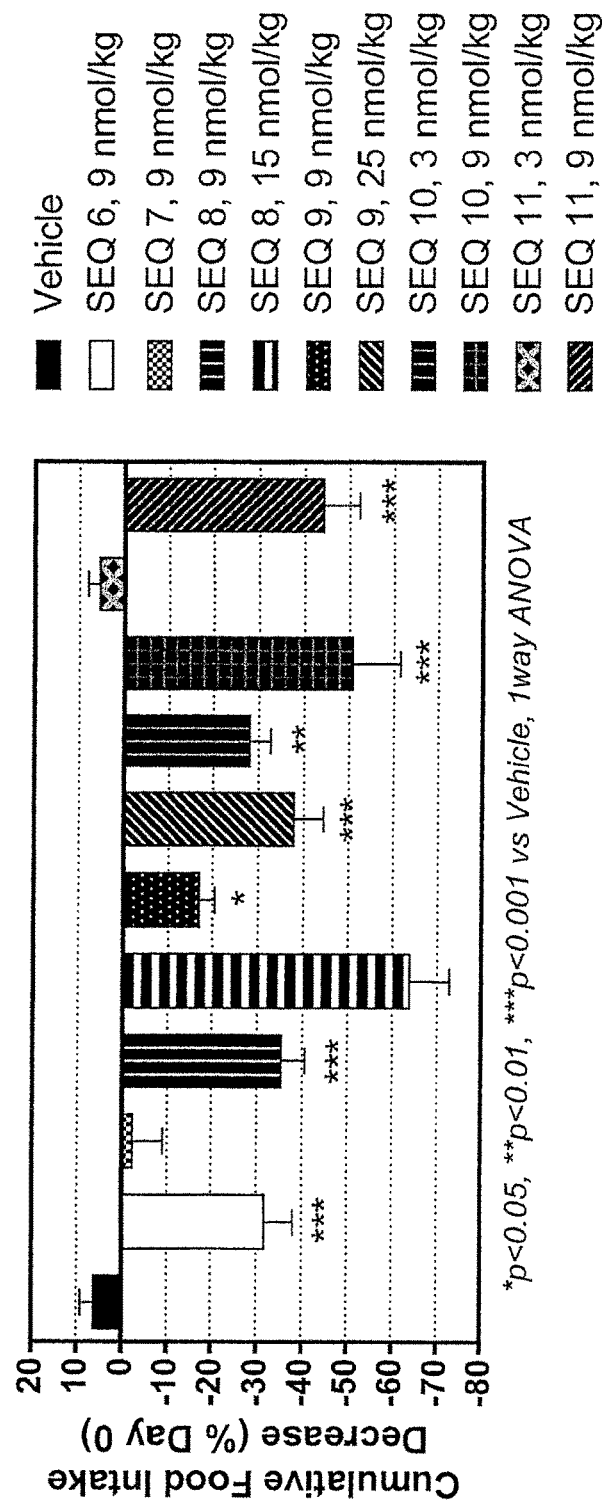
FIG. 3 represents a graph of the cumulative change in food intake (expressed as a percent change of food intake relative to Day 0) of DIO mice treated with a vehicle control or with a dose of a peptide of SEQ ID NO: 6 to 11, as detailed in Example 20.

As shown in FIG. 3, DIO mice (strain C57Bl6/NTac) that were administered with 9 nmol/kg of the peptides of SEQ ID NOs: 6 to 11, with exception of peptides of SEQ ID NOs: 7, exhibited a significant reduction in cumulative food intake after 8 days of dosing (*$p<0.05$, $p<0.01$ *$p<0.001$ vs Vehicle, 1way ANOVA, Dunn's multiple comparisons).

Mice that were administered with 3 nmol/kg of the peptide of SEQ ID NO: 10 exhibited also a significant suppression of food intake, while mice that were administered with 3 nmol/kg of the peptide of SEQ ID NO: 11 exhibited no change in food intake.

Example 21

Figure 4:
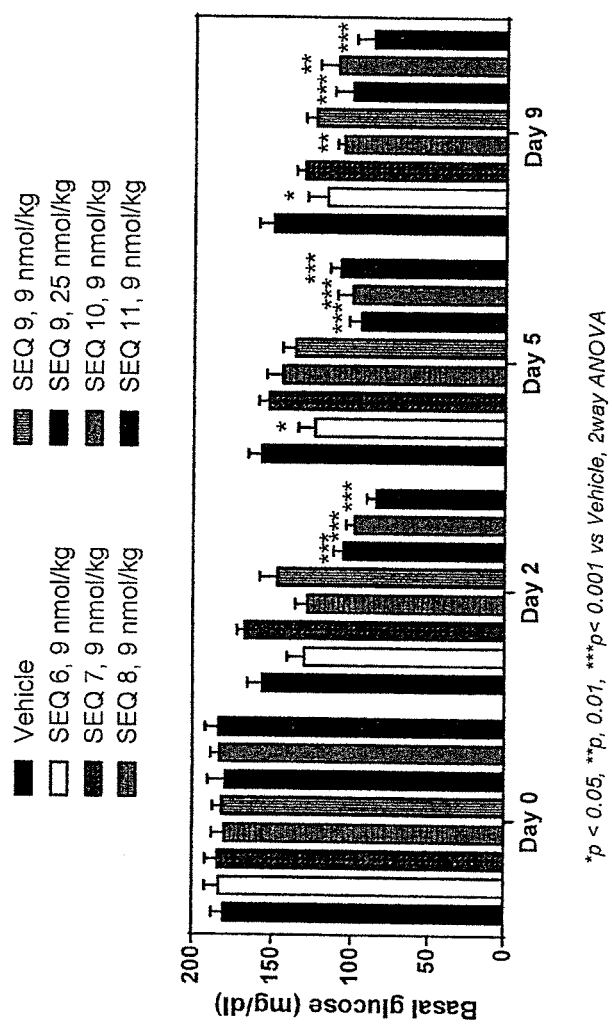
FIG. 4 represents a graph of the basal glucose (mg/dL) of DIO mice treated with a vehicle control or with a dose of a peptide of SEQ ID NO: 6 to 11, as detailed in Example 21.

In addition to cumulative body weight change, ambient glucose levels of the DIO mice (strain C57Bl6/NTac) were measured periodically throughout the study. As shown in FIG. 4, mice that were administered with the peptide of SEQ ID NO: 9 at a dose 25 nmol/kg demonstrated a significant decrease in ambient glucose by the second day of dosing compared to vehicle treated control mice (−75 mg/dL, ***p<0.001 vs Vehicle, 2way ANOVA, Dunnett's multiple comparisons). Mice that were administered with 9 nmol/kg of the peptides of SEQ ID NOs: 10 and 11 demonstrated a similar decrease in ambient glucose. Mice that were dosed with 9 nmol/kg of the peptide of SEQ ID NO: 6 demonstrated a significant decrease in ambient glucose by day 7 of dosing (−60 mg/dL, *p<0.05 vs Vehicle). Mice that were dosed with 9 nmol/kg of the peptides of SEQ ID NOs: 8 demonstrated a significant decrease in ambient glucose by day 9 (−72 mg/dL, **p<0.01 vs Vehicle, 2way ANOVA). Mice that were dosed with 9 nmol/kg of the peptides of SEQ ID NOs: 7 or 9 did not exhibit significant changes in ambient glucose after 9 days of dosing.

Table of Sequences

| SEQ ID NO: | Name | Sequence |
|---|---|---|
| 1 | Glucagon (Homo sapiens) | HSQGTFTSDYSKYLDSRRAQDFVQWLMNT |
| 2 | GLP-1 (7-36) (Homo sapiens) | HAEGTFTSDVSSYLEGQAAKEFIAWLVKGR |
| 3 | Oxyntomodulin (Homo sapiens) | HSQGTFTSDYSKYLDSRRAQDFVQWLMNTKRNRNNIA |
| 4 | Exendin-4 (Heloderma suspectum) | HGEGTFTSDLSKQMEEEAVRLFIEWLKNGGPSSGAPPPS |
| 5 | GLP-2 (Homo sapiens) | HADGSFSDEMNTILDNLAARDFINWLIQTKITD |
| 6 | Co-agonist Peptide 1<br>X2- D-Ser<br>K10- conjugated to γEC16<br>C-Ter- amide | HXQGTFTSDKSKYLDARAAQDFVQWLLDT |
| 7 | Co-agonist Peptide 2<br>X2- D-Ser<br>K10-conjugated to γEγEC16<br>C-Ter- amide | HXQGTFTSDKSKYLDVRRAQDFVQWLLDT |
| 8 | Co-agonist Peptide 3<br>X2- D-Ser<br>K10- conjugated to γEγEC16<br>C-Ter- amide | HXQGTFTSDKSKYLDVRAAQDFVQWLLDT |
| 9 | Co-agonist Peptide 4<br>X2- α-aminoisobutyric acid (Aib)<br>K10- conjugated to γEγEC16<br>X16- Aib<br>X27- L-norleucine (Nle)<br>C-Ter- amide | HXVGTFTSDKSKYLDXRAAQDFVQWLXDT |
| 10 | Co-agonist Peptide 5<br>X2- D-Ser<br>K10- conjugated to γEγEC16<br>C-Ter- amide | HXQGTFTSDKSKYLDARAAQDFVQWLLDT |
| 11 | Co-agonist Peptide 6<br>X2- D-Ser<br>K10- conjugated to γEγEC16<br>C-Ter- amide | HXQGTFTSDKSKYLDERAAQDFVQWLLDT |
| 12 | Co-agonist Peptide 7<br>N-Ter- acetyl<br>K10- conjugated to γEγEC16<br>C-Ter- optional amide | AcHAQGTFTSDKSKYLDERAAQDFVQWLLDT |
| 13 | Co-agonist Peptide 8<br>X2- D-Ser<br>K10- conjugated to γEγEC16<br>C-Ter- optional amide | HXQGTFTSDKSKYLEARAAQDFVQWLLDT |

| SEQ ID NO: | Name | Sequence |
|---|---|---|
| 14 | Co-agonist Peptide 9<br>X2- D-Ser<br>X6- p-fluoro phenylalanine (pFF)<br>K10- conjugated to γEγEC16<br>C-Ter- optional amide | HXQGTXTSDKSKYLDERAAQDFVQWLLDT |
| 15 | Co-agonist Peptide 10<br>X2- D-Ser<br>K10- conjugated to γEγEC16<br>X27- methionine sulfone<br>C-Ter- optional amide | HXQGTFTSDKSKYLDERAAQDFVQWLXDT |
| 16 | Co-agonist Peptide 11<br>X2- D-Ser<br>K10- conjugated to γEγEC16<br>C-Ter- optional amide | HXQGTFTSDKSLYLDERAAQDFVQWLLDT |
| 17 | Co-agonist Peptide 12<br>X2- D-Ser<br>X10- para-aminomethyl phenylalanine (pAF) conjugated to γEγEC16<br>C-Ter- optional amide | HXQGTFTSDXSKYLDARAAQDFVQWLLDT |
| 18 | Co-agonist Peptide 13<br>X2- 1-amino-1-cyclobutane carboxylic acid<br>K10- conjugated to γEγEC16<br>C-Ter- optional amide | HXQGTFTSDKSKYLDERAAQDFVQWLLDT |
| 19 | Co-agonist Peptide 14<br>X2- D-Ser<br>X6- threo-β-Phenylserine (tβP)<br>K10- conjugated to γEγEC16<br>C-Ter- optional amide | HXQGTXTSDKSKYLDERAAQDFVQWLLDT |
| 20 | Co-agonist Peptide 15<br>X2- D-Ser, L-Ala, aib, or 1-amino-cyclobutane carboxylic acid<br>X6- L-Phe, p-fluoro phenylalanine (pFF) or threo-β-phenylserine<br>X10- K conjugated to γEC16, K conjugated to γEγEC16, or pAF conjugated to γEγEC16<br>X12- L-Lys or L-Leu<br>X15- L-Glu or L-Leu or L-Asp<br>X16- aib, L-Ala, L-Glu, or L-Val<br>X18- L-Ala or L-Arg<br>X27- L-Leu, methionine sulfone, or L-Nle<br>C-Ter- optional amide | HXQGTXTSDX$_1$SXYLXXRXAQDFVQWLXDT |
| 21 | X is D-Ser<br>K conjugated to γEC16 or γEγEC16<br>C-terminal amidation | HXQGTFTSDKSKYLDERAAQDFVQWLLDT-NH$_2$ |

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

What is claimed:

1. A peptide, wherein the peptide has the amino acid sequence of SEQ ID NO: 7, 8, 10, 13, or 17, or a pharmaceutically acceptable salt thereof.

2. The peptide of claim 1, wherein the pharmaceutically acceptable salt is the sodium salt.

3. A composition comprising the peptide of claim 1, or a pharmaceutically acceptable salt thereof, and a pharmaceutically acceptable carrier.

4. The composition of claim 3, wherein the composition further comprises an insulin or insulin analog.

5. The composition of claim 4, wherein the insulin analog comprises insulin detemir, insulin glargine, insulin levemir, insulin glulisine, or insulin lispro.

6. A peptide, wherein the peptide has the amino acid sequence of SEQ ID NO: 7, or a pharmaceutically acceptable salt thereof.

7. A peptide, wherein the peptide has the amino acid sequence of SEQ ID NO: 8, or a pharmaceutically acceptable salt thereof.

8. A peptide, wherein the peptide has the amino acid sequence of SEQ ID NO: 10, or a pharmaceutically acceptable salt thereof.

9. A peptide, wherein the peptide has the amino acid sequence of SEQ ID NO: 13, or a pharmaceutically acceptable salt thereof.

10. A peptide, wherein the peptide has the amino acid sequence of SEQ ID NO: 17, or a pharmaceutically acceptable salt thereof.

11. A peptide comprising the structure
HsQGTFTSDK(γEγEC$_{16}$)SKYLDARAAQD-FVQWLLDT-NH$_2$ (SEQ ID NO:10)
wherein "s" is D-serine, the lysine at position 10 is conjugated via its epsilon amino group to a C$_{16}$ fatty acid via a gamma-glutamic acid-gamma-glutamic acid dipeptide (γEγE) spacer, and the peptide, or a pharmaceutically acceptable salt thereof, has a C-terminal amine.

12. The peptide of claim 11, wherein the pharmaceutically acceptable salt is the sodium salt.

13. A composition comprising the peptide of claim 11, or a pharmaceutically acceptable salt thereof, and a pharmaceutically acceptable carrier.

14. The composition of claim 13, wherein the composition further comprises an insulin or insulin analog.

15. The composition of claim 14, wherein the insulin analog comprises insulin detemir, insulin glargine, insulin levemir, insulin glulisine, or insulin lispro.

16. A composition comprising a peptide, or a pharmaceutically acceptable salt thereof, having an amino acid sequence as set forth in SEQ ID NO: 7, 8, 10, 13, or 17, and a pharmaceutically acceptable carrier.

17. The composition of claim 16, wherein the composition further comprises an insulin or insulin analog.

18. The composition of claim 17, wherein the insulin analog comprises insulin detemir, insulin glargine, insulin levemir, insulin glulisine, or insulin lispro.

19. The peptide of claim 16, wherein the pharmaceutically acceptable salt is the sodium salt.

20. A method for treating a patient or individual for a metabolic disease comprising administering to the patient or individual an effective amount of the composition of claim 16 to treat the metabolic disease in the patient or individual, wherein the metabolic disease comprises diabetes, or obesity.

21. The method of claim 20, wherein the diabetes comprises Type I diabetes, Type II diabetes, or gestational diabetes.

22. A method for treating a metabolic disease in a patient or individual comprising:
administering to the patient or individual (i) an effective amount of a composition comprising a peptide, or a pharmaceutically acceptable salt thereof, having an amino acid sequence as set forth in SEQ ID NO: 7, 8, 10, 13, or 17, and a pharmaceutically acceptable carrier, and administering to the patient or individual an effective amount of a composition comprising an insulin or insulin analog and a pharmaceutically acceptable carrier or (ii) an effective amount of a composition comprising a peptide, or a pharmaceutically acceptable salt thereof, having an amino acid sequence as set forth in SEQ ID NO: 7, 8, 10, 13, or 17, an insulin or insulin analog, and a pharmaceutically acceptable carrier,
wherein the composition treats the metabolic disease, wherein the metabolic disease comprises diabetes, or obesity.

23. The method of claim 22, wherein the method in step (i) comprises
(a) administering the composition comprising the peptide at a time prior to administering the composition comprising the insulin or insulin analog;
(b) administering the composition comprising the insulin or insulin analog at a time prior to administering the composition comprising the peptide; or
(c) administering the composition comprising the peptide and the composition comprising the insulin or insulin analog at the same time.

24. The method of claim 22, wherein the insulin analog comprises insulin detemir, insulin glargine, insulin levemir, insulin glulisine, or insulin lispro.

25. The method of claim 22, wherein the diabetes comprises Type I diabetes, Type II diabetes, or gestational diabetes.

26. The method of claim 22, wherein the pharmaceutically acceptable salt is the sodium salt.

27. A method for treating a patient or individual for having a metabolic disease, comprising administering to the patient or individual an effective amount of the peptide of claim 1, or a pharmaceutically acceptable salt thereof, to treat the metabolic disease in the patient or individual, wherein the metabolic disease comprises diabetes, or obesity.

28. The method of claim 27, wherein the diabetes comprises Type I diabetes, Type II diabetes, or gestational diabetes.

29. The method of claim 27, wherein the metabolic disease is diabetes.

30. The method of claim 27, wherein the metabolic disease is obesity.

* * * * *